US012806393B2

(12) United States Patent
Marelli et al.

(10) Patent No.: US 12,806,393 B2
(45) Date of Patent: Nov. 24, 2026

(54) FABRICATION OF POLYMERIC MICRONEEDLES WITH HOLLOW AND POROUS TIPS VIA A SIMPLE MICROMOLDING PROCESS ASSISTED BY IONIC SALTS

(71) Applicant: Massachusetts Institute of Technology, Cambridge, MA (US)

(72) Inventors: Benedetto Marelli, Cambridge, MA (US); Doyoon Kim, Cambridge, MA (US); Hui Sun, Cambridge, MA (US); Yunteng Cao, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 97 days.

(21) Appl. No.: 18/846,145

(22) PCT Filed: Mar. 10, 2023

(86) PCT No.: PCT/US2023/064110

§ 371 (c)(1),
(2) Date: Sep. 11, 2024

(87) PCT Pub. No.: WO2024/073153

PCT Pub. Date: Apr. 4, 2024

(65) Prior Publication Data

US 2025/0195856 A1 Jun. 19, 2025

Related U.S. Application Data

(60) Provisional application No. 63/481,633, filed on Jan. 26, 2023, provisional application No. 63/319,499, filed on Mar. 14, 2022.

(51) Int. Cl.
*A61M 37/00* (2006.01)

(52) U.S. Cl.
CPC .................. *A61M 37/0015* (2013.01); *A61M 2037/0046* (2013.01); *A61M 2037/0053* (2013.01); *A61M 2205/02* (2013.01)

(58) Field of Classification Search
CPC .......... A61M 37/0015; A61M 37/0023; A61M 37/003; A61M 37/0038; A61M 37/0046; A61M 37/0053; A61M 37/0061
See application file for complete search history.

(56) References Cited

U.S. PATENT DOCUMENTS

2013/0338632 A1* 12/2013 Kaplan ................ A61K 9/0021
604/173

FOREIGN PATENT DOCUMENTS

CN 106362223 A * 2/2017 ............. A61L 31/16
CN 110917176 B * 3/2021 ........ A61M 37/0015

* cited by examiner

*Primary Examiner* — Yung-Sheng M Tsui
(74) *Attorney, Agent, or Firm* — McDonnell Boehnen Hulbert & Berghoff LLP

(57) ABSTRACT

What is disclosed herein is a composition comprising a mixture of a soluble polymer in a solvent and an immiscible highly-soluble molecule in the same solvent, wherein the immiscible highly-soluble molecule substitutes inorganic ions, wherein the solubility of the immiscible highly-soluble molecule is more than 50 times higher than the solubility of the soluble polymer in the solvent, and wherein the soluble polymer can be cross linked to become insoluble during a material fabrication process. Also disclosed is a method of making the composition, a microneedle comprising the composition, methods for making a silk protein nanostructure array, and silk protein nanostructure arrays.

19 Claims, 25 Drawing Sheets

Specification includes a Sequence Listing.

| | Thickness (µm) | I.D (µm) |
|---|---|---|
| Section 1 | 40.2 ± 3.5 | 154.7 ± 5.7 |
| Section 2 | 29.9 ± 2.3 | 323.8 ± 7.4 |
| Section 3 | 88.5 ± 8.0 | 619.9 ± 6.0 |

FABRICATION OF POLYMERIC MICRONEEDLES WITH HOLLOW AND POROUS TIPS VIA A SIMPLE MICROMOLDING PROCESS ASSISTED BY IONIC SALTS

CROSS REFERENCE

This application is a U.S. national phase of International Application No. PCT/US23/64110, filed on Mar. 10, 2023, which claims priority to U.S. Provisional Patent Application Ser. Nos. 63/319,499 filed Mar. 14, 2022 and 63/481,633 filed Jan. 26, 2023, each incorporated by reference herein in their entirety.

STATEMENT REGARDING FEDERALLY SPONSORED RESEARCH OR DEVELOPMENT

This invention was made with government support under grant number N00014-21-1-2402 awarded by Office of Naval Research, grant number N000141912317 awarded by the Office of Naval Research, and grant number CMMI-1752172 awarded by the National Science Foundation. The government has certain rights in this invention.

SEQUENCE LISTING STATEMENT

A computer readable form of the Sequence Listing is filed with this application by electronic submission and is incorporated into this application by reference in its entirety. The Sequence Listing is contained in the file created on Sep. 16, 2024 having the file name "22-2197-WO-US.xml" and is 24,375 bytes in size.

BACKGROUND

Hierarchical structures in nature, such as nacre and bone, mainly consist of biopolymer matrices and biomineral inclusions that nucleate from ionic precursors. Inspired by the living structures, researchers have developed biomimetic strategies to utilize biological templates to control the nucleation, growth, and crystallization of inorganic crystals in nanoscale. However, the understanding of salt cations, as mineral precursors, interacting with biopolymers is limited to uncontrollable and disordered "salting out" processes. Therefore, little information is available about utilizing salt cations and their transformation into a mineral phase to direct the assembly of biopolymers to form predetermined nano- and micro-structures.

Tubular structures at the nanoscale possess significant advantages in a broad range of areas, such as catalysis, sensing, microencapsulation, selective mass transport, filtration and drug delivery, to name a few. While the fields of carbon nanotubes and nanotubes made of several non-carbon materials (e.g., metals, oxides, semiconductors) have been progressing rapidly, polymeric nanotubes are much less advanced.

SUMMARY

This Summary introduces a selection of concepts in simplified form that are described further below in the Detailed Description. This Summary neither identifies key or essential features, nor limits the scope, of the claimed subject matter.

One aspect of the disclosure herein is a composition comprising a mixture of a soluble polymer in a solvent and an immiscible highly-soluble molecule in the same solvent, wherein the immiscible highly-soluble molecule substitutes inorganic ions, wherein the solubility of the immiscible highly-soluble molecule is more than 50 times higher than the solubility of the soluble polymer in the solvent, and wherein the soluble polymer can be cross linked to become insoluble during a material fabrication process.

In one embodiment of the composition disclosed herein, the solvent is an organic solvent selected from the group consisting of formic acid (FA), hexafluoroisopropanol (HFIP), and trichloroacetic acid/chloroform. In another embodiment, the solvent is water.

In one embodiment of the composition disclosed herein, the highly-soluble molecule is a polymer selected from the group consisting of polyglycolide (PGA), polylactic acid (PLA), poly(lactic-co-glycolic acid (PLGA), polyamide, polyacrylonitrile, polyacetal, polyester, and polyketone.

In one embodiment of the composition disclosed herein, the soluble polymer is selected from the group consisting of metacrilated silk, metacrilated collagen, tropoelastin, elastin, keratin, alginate, chitosan, chitin, cellulose and derivates, polyvinyl alcohol, chitosan with 1% acetic acid, and pectin. In one embodiment, the soluble polymer is silk fibroin.

In one embodiment of the composition disclosed herein, the immiscible highly-soluble molecule is an ionic salt.

In one embodiment of the composition disclosed herein, the composition comprises silk fibroin (SF) and an ionic salt mixed in water. In one embodiment, the SF is selected from the group consisting of larger silk fibroin ($SF_L$), smaller silk fibroin ($SF_S$), and a mixture thereof. In one embodiment, the SF is 5 wt %. In one embodiment, the ionic salt is selected from the group consisting of NaCl and $CuSO_4$. In one embodiment, the ionic salt is 5 wt %.

In one embodiment of the composition disclosed herein, the weight ratio of immiscible highly soluble molecule: soluble polymer is from 1:100 to 10:100.

In one embodiment of the composition disclosed herein, the immiscible highly-soluble molecule is selected from the group consisting of a highly hydrophilic carbohydrate and a short peptide with less than five residues, or a short peptide which optionally can comprise more than five residues when the entire sequence consists of hydrophobic amino acids. In one embodiment, the hydrophobic amino acids are selected from the group consisting of W, L, I, F, M, V, and Y. In one embodiment, the highly hydrophilic carbohydrate is trehalose.

In one embodiment of the composition disclosed herein, the material fabrication process is selected from the group consisting of x-linking via UV, light, heat, and chemicals.

One aspect of the disclosure herein is a microneedle comprising the composition disclosed herein, wherein the microneedle comprises a hollow base and a penetrating tip.

In one embodiment of the microneedle disclosed herein, the microneedle and the tip are hollow, wherein the microneedle comprises one open channel from base to tip. In one embodiment, the microneedle comprises a hollow base and a porous tip. In one embodiment, the penetrating tip length is suitable for penetration of the microneedle to the xylem or phloem of a plant. In one embodiment, the penetrating tip diameter is capable of penetrating the xylem or phloem of a plant without disrupting the flow of material in the xylem or phloem. In one embodiment, the penetrating, porous tip is capable of sampling fluid in the xylem or phloem of a plant.

In one embodiment, the microneedle disclosed herein comprises at least one active agent selected from the group consisting of proteins, peptides, antigens, immunogens, vaccines, antibodies, or portions thereof, antibody-like molecules, enzymes, nucleic acids, siRNA, shRNA, aptamers, viruses, bacteria, small molecules, cells, hormones, antibiotics, therapeutic agents, diagnostic agents, and any combinations thereof.

One aspect of the disclosure herein is a phase front assembly method for manufacturing a hollow microneedle with a penetrating tip comprising: (a) mixing a soluble polymer in a solvent and an immiscible highly-soluble molecule in the same solvent, wherein the immiscible highly-soluble molecule substitutes inorganic ions, wherein the solubility of the immiscible highly-soluble molecule is more than 50 times higher than the solubility of the soluble polymer in the medium, and wherein the soluble polymer can be cross linked to become insoluble during the phase front assembly method; (b) placing droplets of the mixture in a negative polydimethylsiloxane (PDMS) mold, and (c) air drying the droplets to evaporate solvent from the mixture, resulting in homogenous nucleation and crystallization in the shape of hollow microneedles, thereby forming hollow microneedles.

In one embodiment of the method disclosed herein, the air drying occurs at room temperature and humidity. In one embodiment of the method disclosed herein, the imaging is performed under a microscope or by using a camera. In one embodiment the droplets are 5 μL.

In one embodiment, the method disclosed herein further comprises imaging the evaporation process to monitor needle formation.

In one embodiment, the method disclosed herein further comprises centrifuging the PDMS molds filled with the mixture and placing under vacuum to remove air bubbles, and peeling microneedles off from the mold after air drying.

One aspect of the disclosure herein is a method for delivering a payload to a locus in plant tissue comprising (a) providing a hollow microneedle comprising the composition of claim 1; (b) loading the microneedle device with the payload; and (c) contacting the plant tissue with the microneedle device under conditions sufficient to allow the payload to enter the locus.

One aspect of the disclosure herein is a method of sampling sap from plant tissue to detect the presence of agents in the sap, the method comprising (a) providing a hollow microneedle with a porous tip comprising the composition of claim 1; (b) contacting the plant tissue with the microneedle device under conditions sufficient to allow sap to flow out of the plant tissue and into the hollow microneedle, and (c) collecting the sap for sampling in a collector attached to the hollow microneedle. In one embodiment of the method disclosed herein, the agents to be detected are selected from the group consisting of Cd and As. One embodiment is a microneedle made by the method disclosed herein.

Another aspect of the disclosure is a method for making a silk protein nanostructure array, comprising: (a) infiltrating a nanoporous template with a silk protein solution; (b) material assembly in nanopores of the nanoporous component to produce a silk protein nanostructure array; and (c) removing the nanoporous template in a dissolving solvent. In one embodiment, the nanoporous template comprises polycarbonate (PC), anodic aluminum oxide, and/or macroporous silicon. In another embodiment, the silk protein solution comprises silk fibroin, such as silk fibroin extracted from *Bombyx mori* cocoons. In some embodiments, the silk fibroin is present in the solution at 2% to 20%, or 2% to 10%, by weight. In one embodiment, the silk protein solution comprises a silk-water suspension, including but not limited to silk suspended in formic acid (FA). In another embodiment, the infiltrating comprises placing the nanoporous template on a reservoir of the silk protein solution. In one embodiment, the substrate comprises a glass slide, coverslip, or silicon wafer. In a further embodiment, the methods comprise air drying the PC after infiltrating it with the silk protein solution to template the silk protein in an array of nanostructures within the PC nanopores. In one embodiment, removing the nanoporous template comprises: (a) immersing the glass slide into dichloromethane (DCM) to dissolve the PC; and (b) air drying the glass slide coated with the silk protein nanostructure array. In another embodiment, the silk protein nanostructures comprise silk protein nanotubes, wherein the method further comprises crystalizing inorganics in the silk protein nanotubes. In one embodiment, the nanoporous template comprises PC and the substrate comprises PDMS or polystyrene. In one such embodiment, the method comprises air drying the PDMS or polystyrene after being coated with the silk protein solution and PC to template the silk protein into an array of nanotubular structures on the PDMS or polystyrene. In a further embodiment, the method comprises removing the nanoporous template in a dissolving solvent comprises: (a) peeling the array of silk nanotubular structures off the PDMS or polystyrene, and immersing the array in DCM to dissolve the PC; and (b) air drying the free-standing silk nanotubular structure array. In one embodiment, the silk protein solution comprises silk proteins, horseradish peroxidase (HRP) and hydrogen peroxide ($H_2O_2$). In one such embodiment, the nanoporous template comprises a PC membrane, wherein infiltrating the silk protein solution to the PC membrane is conducted at about 99% humidity, for a time sufficient for the silk solution to fill up the entire pore volume of the PC membrane and undergo sol-gel transition catalyzed by HRP in the presence of $H_2O_2$ within pores of the PC membrane to form silk gel-PC composites. In a further embodiment, removing the nanoporous template in a dissolving solvent comprises successive dehydration of the silk gel-PC composites in increasing concentrations of ethanol followed by drying and dissolving of the PC template in DCM to generate porous silk pillars. In one embodiment, the nanoporous template comprises PC, and wherein the silk fibers are dissolved in FA with about 2 wt % $CaCl_2$ to a final concentration of about 6 wt % silk to produce a silk/$CaCl_2$—PC composite nanopillars. In a further such embodiment, the method further comprises air drying of the silk/$CaCl_2$—PC composite followed by exposing the composite to (1) water vapor to induce silk nanopillar to silk nanotube conversion; or (2) vapor of a 80 v/v % EtOH/water solution to induce formation of mushroom-shaped silk nanopillars.

Another aspect of the disclosure provides silk nanostructure arrays as described herein. In one embodiment, the silk nanostructure array comprises aligned silk nanostructures across an area of at least one $cm^2$. In another embodiment, one or more of the silk nanostructures on the array have an aspect ratio of between about 5 to about 60, or wherein a majority or all of the silk nanostructures on the array have an aspect ratio of between about 5 to about 60. In various embodiments, the silk nanostructures comprise silk nanotubes and/or silk nanopillars. In another embodiment, the silk protein nanostructure array is at least 2 cm×2 cm in size. In a further embodiment the silk protein nanostructures comprise silk protein nanotubes, wherein the silk protein nanotubes comprise crystalized inorganics in the silk protein nanotubes. In one embodiment, the crystalized inorganics comprise hydroxyapatite and/or $CaCO_3$. In other embodiments, the silk nanostructures comprise silk fibroin, such as silk fibroin extracted from *Bombyx mori* cocoons.

The following Detailed Description references the accompanying drawings which form a part this application, and which show, by way of illustration, specific example implementations. Other implementations may be made without departing from the scope of the disclosure.

DETAILED DESCRIPTION

Figure 1:
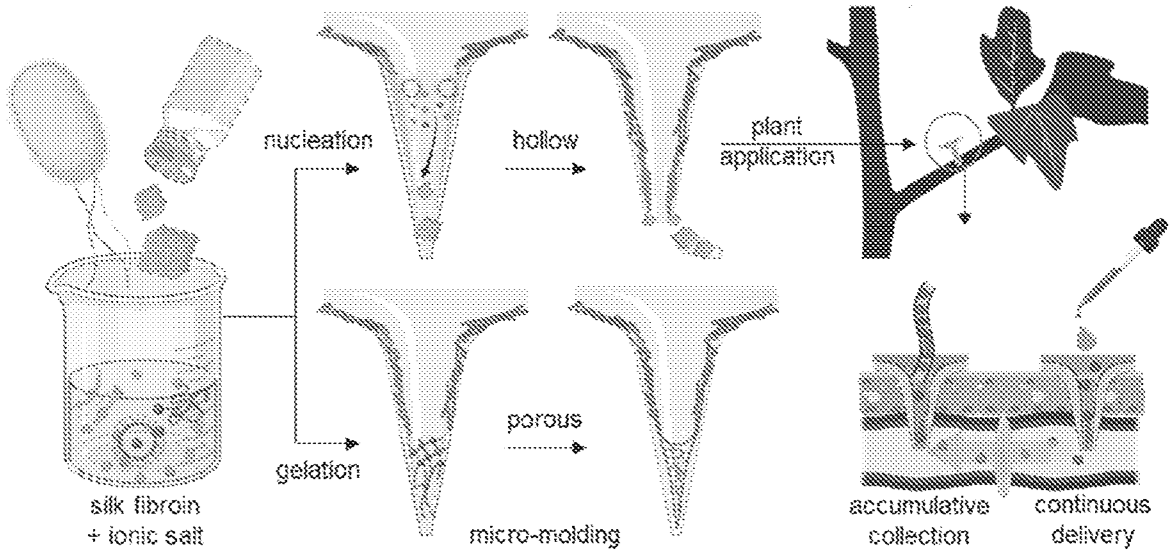
FIG. 1. Schematic illustration of hollow/porous microneedle fabrication and plant application.

Reference numbers in brackets "[ ]" herein refer to the corresponding literature listed in the attached Bibliography which forms a part of this Specification, and the literature is incorporated by reference herein.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

All embodiments of any aspect of the invention can be used in combination, unless the context clearly dictates otherwise. As used herein, "about" means +/−5% of the recited value.

In one aspect, the disclosure provides compositions comprising a mixture of a soluble polymer in a solvent and an immiscible highly-soluble molecule in the same solvent, wherein the immiscible highly-soluble molecule substitutes inorganic ions, wherein the solubility of the immiscible highly-soluble molecule is more than 50 times higher than the solubility of the soluble polymer in the solvent, and wherein the soluble polymer can be cross linked to become insoluble during a material fabrication process. Any suitable solvent may be used as appropriate for an intended use. In some embodiments, the solvent is an organic solvent selected from the group consisting of formic acid (FA), hexafluoroisopropanol (HFIP), and trichloroacetic acid/chloroform. Any suitable highly-soluble molecule may be used as appropriate for an intended use. In some embodiments, the highly-soluble molecule is a polymer selected from the group consisting of polyglycolide (PGA), polylactic acid (PLA), poly(lactic-co-glycolic acid (PLGA), polyamide, polyacrylonitrile, polyacetal, polyester, and polyketone.

In one embodiment, the solvent is water. In one further such embodiment, the soluble polymer is selected from the group consisting of metacrilated silk, metacrilated collagen, tropoelastin, elastin, keratin, alginate, chitosan, chitin, cellulose and derivates, polyvinyl alcohol, chitosan with 1% acetic acid, and pectin. In a specific embodiment, the soluble polymer is silk fibroin.

Any suitable immiscible highly-soluble molecule may be used as appropriate for an intended use. In one embodiment, the immiscible highly-soluble molecule is an ionic salt. In a further embodiment, the composition comprises silk fibroin (SF) and an ionic salt mixed in water. As used herein, the term "silk fibroin" refers to silk fibroin protein or fragment thereof, whether produced by silkworm, spider, or other insect, or otherwise generated (Lucas et al., Adv. Protein Chem., 13: 107-242 (1958)). Silk is naturally produced by various species, including, without limitation: *Antheraea mylitta; Antheraca pernyi; Antheraca yamamai; Galleria mellonella; Bombyx mori; Bombyx mardarina; Galleria mellonella; Nephila clavipes; Nephila senegalensis; Gasteracantha mammosa; Argiope aurantia; Arancus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*. (See U.S. Pat. No. 11,147,282) In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from Nepbila clavipes. In the alternative, in some embodiments, silk fibroins suitable for use in the invention are obtained from a solution containing a genetically engineered silk or recombinantly produced silk harvested from bacteria, yeast, mammalian cells, transgenic animals or transgenic plants. See, e.g., WO 97/08315 and U.S. Pat. No. 5,245,012, each of which is incorporated herein by reference in its entirety.

Silk fibroin is a hydrophobic structural protein having amphiphilic properties. Silk fibroin heavy chain are made of amorphous and crystalline fractions. Beta-sheets of fibroin proteins stack to form crystals, whereas other segments form amorphous domains. See 11,147,282, incorporated by reference herein in its entirety. The protein secondary as well as tertiary structures can be further controlled due to the polymorphism of the protein, permitting control over the protein physical and mechanical properties. The molecular weight of regenerated silk fibroin varies depending on the processing conditions, such as boiling time.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These “Ala-rich” and “Gly-rich” hydrophobic blocks are typically separated by segments of amino acids with bulky side-groups (e.g., hydrophilic spacers). See U.S. Pat. No. 11,147,282.

In some embodiments, core repeat sequences of the hydrophobic blocks of the silk fibroin are represented by the following amino acid sequences and/or formulae: $(GAGAGS)_{5-15}$ (SEQ ID NO: 1); $(GX)_{5-15}$ (X=V, I, A); GAAS (SEQ ID NO: 2); $GX_{1-4}$ GGX (SEQ ID NO: 3); GGGX (X=A, S, Y, R, D V, W, R, D) (SEQ ID NO: 4); GLGGLG (SEQ ID NO: 5); GXGGXG (X=L, I, V, P) (SEQ ID NO:6); GPX (X=L, Y, I); $(GP\ (GGX)_{1-4}\ Y)$ n (X=Y, V, S, A) (SEQ ID NO:7); GRGGAn (n is 1-10) (SEQ ID NO:8); GGXn (X=A, T, V, S; n is 1-10); $GAG(A)_{6-7}GGA$ (SEQ ID NO:9); and GGX GX GXX (X=Q, Y, L, A, S, R) (SEQ ID NO: 10).

In some embodiments, the silk fibroin contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments, the silk fibroin comprises at least one hydrophilic spacer sequence (“hydrophilic block”) that is about 4-50 amino acids in length. Non-limiting examples of the hydrophilic spacer sequences include peptides at least 75%, 80%, 85%, 90%, 91%, 92%, 93%, 94%, 95%, 96%, 97%, 98%, 99%, or 100% identical to (SEQ ID NO: 11)
TGSSGFGPYVNGGYSG;

(SEQ ID NO: 12)
YEYAWSSE;

(SEQ ID NO: 13)
SDFGTGS;

(SEQ ID NO: 14)
RRAGYDR;

(SEQ ID NO: 15)
EVIVIDDR;

(SEQ ID NO: 16)
TTIIEDLDITIDGADGPI;
and (SEQ ID NO: 17)
TISEELTI.

Silk fibroin proteins are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 18) contributes to beta-spiral formation (reviewed in Omenetto and Kaplan (2010) Science 329:528-531; see also WO 2011/130335 (PCT/US2011/032195), the contents of which are incorporated herein by reference.

In various embodiments, the silk fibroin has an average molecular weight of between about 5 kD and about 400 kD; about 5 kD and about 350 kD; about 5 kD and about 300 kD; about 5 kD and about 250 kD; about 5 kD and about 200 kD; about 5 kD and about 150 kD; about 5 kD and about 100 kD; about 50 kD and about 400 kD; about 50 kD and about 350 kD; about 50 kD and about 300 kD; about 50 kD and about 250 kD; about 50 kD and about 200 kD; about 50 kD and about 150 kD; about 50 kD and about 100 kD; about 100 kD and about 400 kD; about 100 kD and about 350 kD; about 100 kD and about 300 kD; about 100 kD and about 250 kD; about 100 kD and about 200 kD; or about 100 kD and about 150 kD.

In one embodiment, the SF is selected from the group consisting of larger silk fibroin ($SF_L$), smaller silk fibroin ($SF_S$), and a mixture thereof. As used herein, SF with average molecular weights of ~270 kDa are $SF_L$ and ~200 kDa are $SF_S$. In one embodiment, the SF is present in the composition at 5 wt %. In another embodiment, the ionic salt is selected from the group consisting of NaCl and $CuSO_4$. In a further embodiment, the ionic salt is present at 5 wt %. The weight ratio of immiscible highly soluble molecule:soluble polymer may be any as suitable for an intended purpose. In one embodiment, the weight ratio of immiscible highly soluble molecule:soluble polymer is from 1:100 to 10:100.

In another embodiment, the immiscible highly-soluble molecule is selected from the group consisting of a highly hydrophilic carbohydrate and a short peptide with less than five residues, or a short peptide which optionally can comprise more than five residues when the entire sequence consists of hydrophobic amino acids. In a further embodiment, the hydrophobic amino acids are selected from the group consisting of W, L, I, F, M, V, and Y. In one embodiment, the highly hydrophilic carbohydrate is trehalose.

The soluble polymer can be cross linked to become insoluble during any material fabrication process as suitable for an intended purpose. In one embodiment, the material fabrication process is selected from the group consisting of x-linking via UV, light, heat, and chemicals.

In another embodiment, the disclosure provides microneedles comprising the composition of any embodiment of combination of embodiments of this aspect, wherein the microneedle comprises a hollow base and a penetrating tip. In one embodiment, the microneedle and the tip are hollow, wherein the microneedle comprises one open channel from base to tip. In another embodiment, the microneedle comprises a hollow base and a porous tip.

The disclosure herein derives manipulated microneedle tips in solid, hollow, and porous structures by adding ionic salt in SF solutions (FIG. 1). The interaction between the self-assembling SF and ionic salt determined when and where the salt crystals form architecting microneedle's internal structure beyond simply replicating the master mold. The versatile design of microneedle structures is particularly beneficial to tissue-specific plant applications. Also disclosed herein is the superior delivery and collection capabilities of the microneedles of the disclosure applied to tomato petioles. An attachable collector integrated to a single hollow microneedle (HMN) effectively accumulated cadmium (Cd), enabling an early prediction of heavy metals bioaccumulation of existing at low concentrations in the environment. Thus, in some embodiments, the penetrating tip length is suitable for penetration of the microneedle to the xylem or phloem of a plant. In other embodiments, the penetrating tip diameter is capable of penetrating the xylem or phloem of a plant without disrupting the flow of material in the xylem or phloem. In some embodiments, the penetrating, porous tip is capable of sampling fluid in the xylem or phloem of a plant. In further embodiments, the microneedle can be used to deliver an active agent to, for example, plants. In non-limiting embodiments, the microneedle further comprises at least one active agent selected from the group consisting of vitamins, proteins, peptides, antigens, immunogens, vaccines, antibodies or portions thereof, antibody-like molecules, enzymes, nucleic acids, siRNA, shRNA, aptamers, viruses, bacteria, small molecules, cells, hormones, antibiotics, therapeutic agents, diagnostic agents, and any combinations thereof. The microneedles not only can be used to deliver metabolically-relevant cargo molecules to plants by adding their vasculature, but also enables their translocation in fruits. Between the plant and the fruit there is the pedicel that modulates passage of molecules and selects what molecules is transferred into the fruit. Little is known on how the pedicel works but the microneedles and method of the disclosure permit engineering this "gate" as eventually to, for example, regulates key elements such as fruit weight, color, taste, presence of nutritionally relevant molecules, etc. By way of non-limiting example, the inventors demonstrated that the hollow structure in the microneedles enabled the delivery of large quantity of payloads (exemplified by vitamins) that were restricted before.

In another aspect, the disclosure provides a phase front assembly method for manufacturing a hollow microneedle with a penetrating tip comprising: (a) mixing a soluble polymer in a solvent and an immiscible highly-soluble molecule in the same solvent, wherein the immiscible highly-soluble molecule substitutes inorganic ions, wherein the solubility of the immiscible highly-soluble molecule is more than 50 times higher than the solubility of the soluble polymer in the medium, and wherein the soluble polymer can be cross linked to become insoluble during the phase front assembly method; (b) placing droplets of the mixture in a negative polydimethylsiloxane (PDMS) mold, and (c) air drying the droplets to evaporate solvent from the mixture, resulting in homogenous nucleation and crystallization in the shape of hollow microneedles, thereby forming hollow microneedles. Herein disclosed is the simultaneous manipulation of polymer assembly, exemplified by silk fibroin (SF) assembly, and nucleation of salt crystals at their phase fronts to drive the formation of ordered nanoporous and hollow microstructures in micro-confinement. The phase front design methods of this aspect permit fabrication of new microneedles that bridge biotic/abiotic interfaces to promote sustainable food and agriculture systems. For example, the phase front assembly methods enable the formation of hollow microneedles disclosed herein, which in turn allows, for example, the delivery of large quantities of cargo molecules to plants by adding to their vasculature and also enables their translocation in fruits.

In one embodiment, the air drying occurs at room temperature and humidity. In a further embodiment, the method further comprises a step of imaging the evaporation process to monitor needle formation. Any suitable imaging may be used, including but not limited to microscopy or camera imaging. Any suitable size droplets of the mixture may be used. In one embodiment, the droplets are 5 μL in diameter.

In another embodiment, the method further comprises (d) centrifuging the PDMS molds filled with the mixture and placing under vacuum to remove air bubbles, and (e) peeling microneedles off from the mold after air drying. In another embodiment, the disclosure provides a microneedle produced by the method of any embodiment of the disclosure.

The disclosure further provides methods for delivering a payload to a locus in plant tissue comprising (a) providing a hollow microneedle comprising the composition of any embodiment disclosed herein; (b) loading the microneedle device with the payload; and (c) contacting the plant tissue with the microneedle device under conditions sufficient to allow the payload to enter the locus. The disclosure also provides methods of sampling sap from plant tissue to detect the presence of agents in the sap, the method comprising (a) providing a hollow microneedle with a porous tip comprising the composition of any embodiment disclosed herein; (b) contacting the plant tissue with the microneedle device under conditions sufficient to allow sap to flow out of the plant tissue and into the hollow microneedle, and (c) collecting the sap for sampling in a collector attached to the hollow microneedle. The method can be used, for example, to detect an agent in the sap, including but not limited to Cd and As.

In another aspect, the disclosure provides methods for making a silk protein nanostructure array, comprising: (a) infiltrating a nanoporous template with a silk protein solution; (b) material assembly in nanopores of the nanoporous component to produce a silk protein nanostructure array; and (c) removing the nanoporous template in a dissolving solvent. As described in the examples, the methods of the disclosure are rapidly scalable and robust for fabricating large, well-aligned 1D nanostructures made of silk proteins. Benefitting from the polymorphic nature of silk, precise control over the size, density, aspect ratio, morphology (nanotubes versus nanopillars) and polymorphs of silk nanostructures are achieved, which then allows for programmable modulation of the end materials' functions and properties (e.g., hydrophobicity, oleophilicity and gas permeability). The silk nanotube arrays fabricated present great utility as anti-fouling coatings against marine algae, in oil extraction from oil-water mixtures, and as a packaging material with improved gas barrier property.

The silk protein nanostructure array may comprise any silk protein nanostructures (i.e., having their smallest dimension in the nm to sub-micron scale) or combinations thereof as deemed appropriate for an intended use. In some embodiments, the nanostructures may comprise silk nanotubes (hollow). In other embodiments, the nanostructures may comprise silk nanopillars (solid).

Any nanoporous template may be used as appropriate for an intended purpose. In some embodiments, the nanoporous template comprises polycarbonate (PC), anodic aluminum oxide, and/or macroporous silicon. In one embodiment, the nanoporous template comprises PC.

Any silk protein may be present in the silk protein solution as suitable for an intended purpose. In one embodiment, the silk protein comprise silk fibroin, as described above. Any embodiments or combination of embodiments of silk fibroin disclosed above are equally applicable to this aspect.

In various embodiments, the silk fibroin has an average molecular weight of between about 5 kD and about 400 kD; about 5 kD and about 350 kD; about 5 kD and about 300 kD; about 5 kD and about 250 kD; about 5 kD and about 200 kD; about 5 kD and about 150 kD; about 5 kD and about 100 kD; about 50 kD and about 400 kD; about 50 kD and about 350 kD; about 50 kD and about 300 kD; about 50 kD and about 250 kD; about 50 kD and about 200 kD; about 50 kD and about 150 kD; about 50 kD and about 100 kD; about 100 kD and about 400 kD; about 100 kD and about 350 kD; about 100 kD and about 300 kD; about 100 kD and about 250 kD; about 100 kD and about 200 kD; or about 100 kD and about 150 kD.

In one embodiment, the silk protein solution comprises silk fibroin, such as silk fibroin extracted from *Bombyx mori* cocoons.

The silk protein, such as silk fibroin, may be present in any concentration in the silk protein solution as appropriate for an intended use. In one embodiment, the silk fibroin is present in the solution at 2% to 20% by weight. In other embodiments, the silk fibroin is present in the solution at 2% to 15% or 2% to 10% by weight.

The silk protein solutions may differ dependent on the desired silk protein nanostructure array to be produced. In one embodiment, the silk protein solution comprises a silk-water suspension.

In another embodiment, the silk protein solution comprises silk suspended in formic acid (FA). In one such embodiment, the silk protein solution comprises degummed silk fibers suspended in FA and $CaCl_2$). Degumming of silk fibers involves removal of sericin (a proteinaceous substance that covers the fiber) and random cleavage of peptide bonds of silk fibroin in a boiling alkaline solution (e.g., 0.02 M sodium carbonate). In another embodiment, the silk suspended in FA is obtained by lyophilizing a silk-water suspension and resuspending the lyophilized silk in FA.

Infiltrating the nanoporous template with the silk protein solution can be carried out in any way suitable for an intended use. In one embodiment, the infiltrating comprises placing the nanoporous template on a reservoir of the silk protein solution.

In another embodiment, the infiltrating comprises coating a solid substrate with a layer of silk protein solution and placing the nanoporous template on the layer of silk protein solution. Any solid substrate may be used in this embodiment as appropriate for an intended purpose. In one embodiment, the substrate comprises a glass slide, coverslip, or silicon wafer. In another embodiment, the nanoporous template comprises PC and the substrate comprises a glass slide.

The methods may comprise air drying the nanoporous template, such as PC, after infiltrating it with the silk protein solution to template the silk protein in an array of nanostructures within the nanoporous template.

In one embodiment, the nanoporous template comprises PC, and removing the nanoporous template comprises: (a) immersing the glass slide into dichloromethane (DCM) to dissolve the PC; and (b) air drying the glass slide coated with the silk protein nanostructure array.

In one embodiment, the silk protein solution comprises amorphous silk, wherein prior to immersing in DCM, the dried silk-PC composite is incubated in either pure water vapor or vapor from 80 v/v % EtOH/water for a time sufficient to induce conformational change of silk from amorphous to type II β-turns and/or antiparallel β-pleated sheets.

In another embodiment, the silk protein nanostructures comprise silk protein nanotubes, wherein the method further comprises crystalizing inorganics in the silk protein nanotubes. Any inorganics may be crystalized in the silk protein nanotube as appropriate for an intended purpose. In one embodiment, the inorganics comprise hydroxyapatite and/or $CaCO_3$ in different crystalline phases. As described in the examples, crystallization can be pursued in the nanotube pores generating silk-CaCO3 composite with the possibility to control the phase composition of CaCO3 crystals (i.e. calcite and vaterite), as silk is able to interact with amorphous calcium carbonate and template its crystallization In another embodiment, the nanoporous template comprises PC and the substrate comprises PDMS or polystyrene. In this embodiment, the method may further comprise air drying the PDMS or polystyrene after being coated with the silk protein solution and PC to template the silk protein into an array of nanotubular structures on the PDMS or polystyrene. In a further embodiment, removing the nanoporous template in a dissolving solvent comprises: (a) peeling the array of silk nanotubular structures off the PDMS or polystyrene, and immersing the array in DCM to dissolve the PC; and (b) air drying the free-standing silk nanotubular structure array.

In another embodiment, the silk protein solution comprises silk proteins, horseradish peroxidase (HRP) and hydrogen peroxide ($H_2O_2$). This embodiment may be used, for example, in generating silk protein nanopillars. In this embodiment, the HRP and $H_2O_2$ may be present at any suitable concentration for catalyzing a sol-gel transition of the silk protein solution. In one embodiment, the HRP is present in the silk protein solution at a concentration of about 10 U/ml, and the hydrogen peroxide is present in the silk protein solution at a concentration of about 1.65 mM. In a further embodiment, the nanoporous template comprises a PC membrane, wherein infiltrating the silk protein solution to the PC membrane is conducted at about 99% humidity, for a time sufficient for the silk solution to fill up the entire pore volume of the PC membrane and undergo sol-gel transition catalyzed by HRP in the presence of $H_2O_2$ within pores of the PC membrane to form silk gel-PC composites. In one embodiment, removing the nanoporous template in a dissolving solvent comprises successive dehydration of the silk gel-PC composites in increasing concentrations of ethanol followed by drying and dissolving of the PC template in DCM to generate porous silk nanopillars. In another embodiment, increasing concentrations of ethanol comprise 50%, 75%, 90% and 98% ethanol for about 30 minutes each, and the drying comprises critical point drying.

In one embodiment, the silk protein solution comprises silk suspended in formic acid (FA) and the nanoporous template comprises PC. In one such embodiment, the silk fibers are dissolved in FA with about 2 wt % $CaCl_2$ to a final concentration of about 6 wt % silk to produce silk/$CaCl_2$—PC composite nanopillars. In another embodiment, the method further comprises air drying of the silk/$CaCl_2$—PC composite followed by exposing the composite to (1) water vapor to induce silk nanopillar to silk nanotube conversion; or (2) vapor of an 80 v/v % EtOH/water solution to induce formation of mushroom-shaped silk nanopillars. In a further embodiment, removing the nanoporous template in a dissolving solvent comprises dissolving the PC template in DCM.

The resulting silk protein nanostructure array may be any size or dimension as suitable for an intended use. The methods of the disclosure are rapidly scalable and robust for fabricating large, well-aligned 1D nanostructures. The size may thus be any custom size, such as 20×20 $cm^2$. In one embodiment, the silk protein nanostructure array is at least 1 cm×1 cm in size.

The nanoporous template may have pore sizes of any suitable size as appropriate for an intended use. In one embodiment, the nanoporous template has pore sizes ranging from about 10 nm to about 2 μm in diameter. The nanoporous template may have any thickness as appropriate for an intended use. In one embodiment, the nanoporous template has a thickness of about 6 μm to about 10 μm. In some embodiments, the silk protein nanostructures in the silk protein nanostructure array have an aspect ratio (defined by nanostructure length divided by nanostructure diameter) of about 5 to about 60.

In another aspect, the disclosure provides silk nanostructure arrays prepared by the method of any embodiment or combination of embodiments herein. In another aspect, the disclosure provides silk nanostructure arrays as described herein. The silk nanostructure arrays may comprise any embodiment or combination of embodiments or characteristics disclosed herein. In one embodiment, the array comprises aligned silk nanostructures across an area of at least one $cm^2$. In one such embodiment, the array comprises aligned silk nanostructures within ±30° from the vertical across an area of at least one $cm^2$. In another embodiment, one or more of the silk nanostructures on the array have an aspect ratio of between about 5 to about 60. In another embodiment, a majority (more than 50%) of the silk nanostructures on the array have an aspect ratio of between about 5 to about 60. In various further embodiments, 60%, 70%, 80%, 90% or more of the silk nanostructures on the array have an aspect ratio of between about 5 to about 60.

The array may comprise any type of silk nanostructure, or combinations of different types of silk nanostructures. In one embodiment, wherein the silk nanostructures comprise silk nanotubes. In another embodiment, the silk nanostructures comprise silk nanopillars. In a further embodiment, the silk nanostructures comprise silk nanotubes and silk nanopillars.

The arrays may be any size, as described herein. In some embodiments, the silk protein nanostructure array may be at least 2 cm×2 cm in size. In other embodiments, the silk protein nanostructure array may be at least 5 cm×5 cm; 10 cm×10 cm, or 20×20 cm in size.

In a further embodiment, the silk protein nanostructures may comprise silk protein nanotubes, wherein the silk protein nanotubes comprise crystalized inorganics in the silk protein nanotubes. In one embodiment, the crystalized inorganics comprise hydroxyapatite and/or $CaCO_3$. In another embodiment, crystalized $CaCO_3$ is present in different crystalline phases (calcite and vaterite).

The silk nanostructures in the array may comprise silk of any embodiment, including those disclosed herein. In one embodiment, the silk nanostructures comprise silk fibroin, such as silk fibroin extracted from *Bombyx mori* cocoons.

Example 1

Preparation of Silk Fibroin Solution.

The regenerated silk fibroin was extracted from *Bombyx mori* silkworm cocoons following an established protocol [25]. Cocoons (available in Jeollanam-do, South Korea) were cut into small pieces (~2×2 $cm^2$) and boiled in 0.02 M sodium carbonate for ten min ($SF_L$) and 30 min ($SF_S$) to remove the sericin. The obtained degummed silk fibers were then washed with ultrapure water, dried overnight, and dissolved in 9.3 M lithium bromide for 4 h at 60° C. The dissolved silk fibroins were dialyzed against ultrapure water in a dialysis cassette (molecular weight cut-off: 3500 Da) for two days with frequent replacements. The resulting silk fibroin solutions were then centrifuged to remove impurities. The final silk fibroin solution was diluted with water to 5 wt %, and then stored at 4° C. before use. Size distribution of $SF_L$ and $SF_S$ were determined by sodium dodecyl sulfate-polyacrylamide gel electrophoresis (SDS-PAGE, Bio-Rad Laboratories) [22].

Fabrication and monitoring of silk films and needles. Silk fibroin solutions (5 wt %, $SF_L$ and $SF_S$) ratio were mixed with ionic salts (5 wt %, NaCl and $CuSO_4$) at varying ratios. Then, 5 μL droplets of each mixture were placed on flat PMDS (SYLGARDIM 184, Dow-Corning Corp.) surface and air dried at room temperature and humidity. Changes in droplet sizes and contact angles were monitored using a portable USB digital microscope (Jiusion). NaCl was chosen as a representative salt with high water solubility enabling the monitoring its crystallization behavior at a wide range of concentration. $CuSO_4$ is also investigated as a highly soluble salt and its blue color allows us to monitor its phase separation more easily under microscope. The completed dried droplets were imaged under optical microscope (Nikon ECLIPSE™ TE2000-E).

The macroscale needles were prepared by casting the mixture of 5% $SF_S$ and 5% ionic $CuSO_4$ solutions in a negative PDMS mold (0.6 cm base diameter and 0.9 cm long). The needle formation process was imaged every 30 minutes by a digital single-lens reflex camera (Canon EOS 5 MARK IV) with a macro lens (EF 100 mm f/2.8). The microneedle arrays were fabricated by casting the mixture of 2.0-3.6 mL silk fibroins (5 wt %, $SF_S$ and $SF_L$) with varying volume of ionic salt solutions (5 wt %, NaCl and $CuSO_4$) in negative PDMS molds (10×10 microneedles, 600 μm base diameter, 1,600 μm long, and 2 mm spacing between needles). The molds filled with the mixed solutions were centrifuged (4,000 rcf, 5 min) and placed under vacuum for 30 minutes to remove air bubbles entrapped between the molds and the solutions. The arrays were peeled off from the mold after air dry and cut into small pieces with desired number of microneedles for further experiments or characterization. As a post-treatment, microneedles were soaked in 80% ethanol for one day for silk crystallization. If needed, the crystallized silk microneedles were washed with deionized water or 0.1 mM hydrochloric acid for another day to remove NaCl and $CuSO_4$ crystals precipitated in the microneedles.

Characterization of Microneedles.

The optical images of individual silk microneedles and were obtained with a microscope (Nikon ECLIPSE™ TE2000-E). The microneedles were sputter coated with gold for 10 nm for collecting SEM images (Zeiss MERLIN™ High-resolution SEM and JEOL JSM-6010LA), Line profiles of Cu/N weight ratios along the microneedles were collected by SEM/EDS (Zeiss MERLIN™ High-resolution SEM).

The porous microneedles were evaluated by a confocal Raman spectroscope system established in the Physical Optics and Electronics Group at MIT. Raman spectra along the microneedle from the tip end to the base at 100 μm were collected at a range of Raman shift (200-1900 $cm^{-1}$) by using a 785 nm laser (4 mW power, integrating signals from 60 seconds×2 scans). The collected spectra were post-treated for the background subtraction, cosmic ray removal, and Savitzky-Golay filtering (order 2, frame length 11).

A hollow microneedle was scanned by the 3D X-ray micro-computed tomography system (ZEISS VERSA™ 520 micro-CT System) with the following parameters: source setting 80 kV and 7 W, source filter air, camera binning 1, and exposure time 5 seconds. The objective was 4× and the pixel size was around 1.5487 μm. 2401 projections were taken while the sample rotated 360°.

Residual Cu contents in the microneedles were analyzed by using an inductively coupled plasma-optical emission spectrometer (Agilent 5100 DVD). Samples were prepared by digesting three microneedles in 500 μL NaOH (3 N, 60°

C.) for 5 h. The digested solutions were added to 4.5 mL nitric acid (5%) and filtered through 0.2 μL cellulose acetate syringe filter.

Mechanical Testing of Microneedles.

The tip breaking forces of the microneedles were evaluated by the static compression strength test by a DYNAMIC MECHANICAL ANALYSIS (TA instruments Q850) at a loading speed of 1 mm $min^{-1}$.

Analyses of Secondary Silk Protein Structures.

Fourier-transform infrared spectroscopy (FTIR, Perkin Elmer SPECTRUM 65) was used to evaluate the effects of $CuSO_4$ addition and post treatments silk materials on the secondary protein structure. For the evaluation, silk films were prepared with 400 μL $SF_S$ (5%) and 0-40 μL $CuSO_4$ (5%) solutions in PMDS mold with rectangular wells (1×1×0.3 $cm^{-3}$) that mimicked silk curing environment in the microneedle molds. FTIR spectra were collected at a wavelength range of 4,000 to 650 $cm^{-1}$, with a resolution of 4 $cm^{-1}$ and an accumulation of 64 scans. The relative fractions of β-sheet and random coil were determined by Fourier self-deconvolution of the amide I band (1705-1595 $cm^{-1}$) and Gaussian curve-fitting of the deconvoluted spectra.

Sampling and Delivery Experiments.

Tomato (*Solanum lycopersicum*) plant was chosen as a working model in this study because of their well-known vascular structure and importance in agriculture. They were grown in pots for 4-6 weeks from seeds with regular water and fertilizer feeding at a room temperature with 12 h photoperiod per day. Microneedles were injected into petioles of plants in pots, at approximately 10 cm above the root, for delivery and sampling of fluorescein (from sodium salt, Mw 376.27 g $mol^{-1}$, $pK_a$ ~6.4, Sigma), used as a model biomolecule. The petioles with a dimeter around 2-2.5 mm were selected as injection spots so the microneedles can reach both xylem phloem located at the depths around 700 and 850 μm respectively [22]. For the delivery, a 2.5 μL droplet of 0.2% sodium fluorescein was placed on the backside of the microneedle that facings up, so the droplet can be absorbed into the microneedle or directly inside the petiole (in the case of hollow needle) with the gravitation force. A piece of tissue paper (0.3 cm×0.5 cm) was rolled and inserted into the well of the sampling microneedle from the backside as a collector of fluorescein delivered from another microneedle used as an injector.

Micro-Tom, a dwarf cultivar of tomato (*Solanum lycopersicum* L.) was used as the model to deliver Vitamin $B_{12}$. They were grown in pots from seeds a plant room under long day (16 h light/8 h dark) at 80 μmol $m^{-2}$ $s^{-1}$, 70-90% relative humidity, day and night temperatures of 26° C. and 20° C., respectively. Plants were used for experiments when the growing fruits were around 1-3 g. Hollow microneedles were injected on stem, pedicel, and sepal. 1 mM Vitamin $B_{12}$ solution (~20 ul) was added continuously through the microneedle over 2 hours. The fruits were collected after 24 h of application and homogenized. 80% methanol was used to extract Vitamin B12 from the homogenized fruits at a volume weight ratio of 3:1. The mixture was sonicated for 30 minutes in an Ultrasonic Bath Sonicator, incubated for 24 hours at 4° C., and centrifuged at 20,000×g for 30 minutes. The supernatant was collected for LC/MS using an Agilent 6545 mass spectrometer coupled to an Agilent Infinity 1260 LC system with a ZORBAX Eclipse Plus™ C18 column (2.1×150 mm, 3.5 μm), Solvent A was 0.1% formic acid in water and solvent B was acetonitrile with 0.1% (v/v) Formic acid. The gradient conditions were 0% B (0-1.5 min), 0-40% B (1.5-10 min), 40-60% B (10-13 min), 60-99% B (13-14.5 min), 99-0% B (14.5-16 min) with constant flow 300 μl/min. Stoptime was 15 minutes and Posttime was 3 minutes. Acquisition parameters were set as Temperature 25° C., Source Dual AJS ESI, positive ion polarity, mode MS (Seg), mass range 100-3000 m/z, acquisition rate 2 spectra/s, and injection volume 5 μl. Vitamin B12 was calculated at 678.29. 678.79, and 679.29 m/z using the standard curve $y=2.02\times10^6\times$ (adjusted $R^2=0.99987$).

For the sampling of Cd and As, tomato plants (4-6 weeks) were transferred to 100 mL plant media (Hoagland's No. 2 Basal Salt Mixture) containing cadmium nitrate tetrahydrate (1 or 10 mg Cd $L^{-1}$, Sigma-Aldrich) or sodium arsenite (1 mg As $L^{-1}$, Spectrum Chemical) one day before the microneedle injection. The injected microneedle was digested in 500 μL NaOH (3 N, 60° C.) for 5 h, then transferred to 2 mL nitric acid (5%). The tissue paper collector attached to the microneedle was transferred to 1 mL nitric acid (5%) and heated at 60° C. for 5 h. After heating, additional 1.5 mL nitric acid (5%) were added for dilution. Bioaccumulated Cd and As in the plant leaves after sampling experiments were extracted in concentrated nitric acid and hydrogen peroxide by the microwave digestion system (Milestone ULTRAWAVE™). Solutions extracting Cd and As from the microneedle, tissue paper, and leaves were filtered through 0.2 μL cellulose acetate syringe filters and analyzed by a inductively coupled plasma-mass spectrometer (ICP-MS, Agilent 7900).

Results and Discussion

Salt Crystallization During Silk Film Formation.

Figure 2:
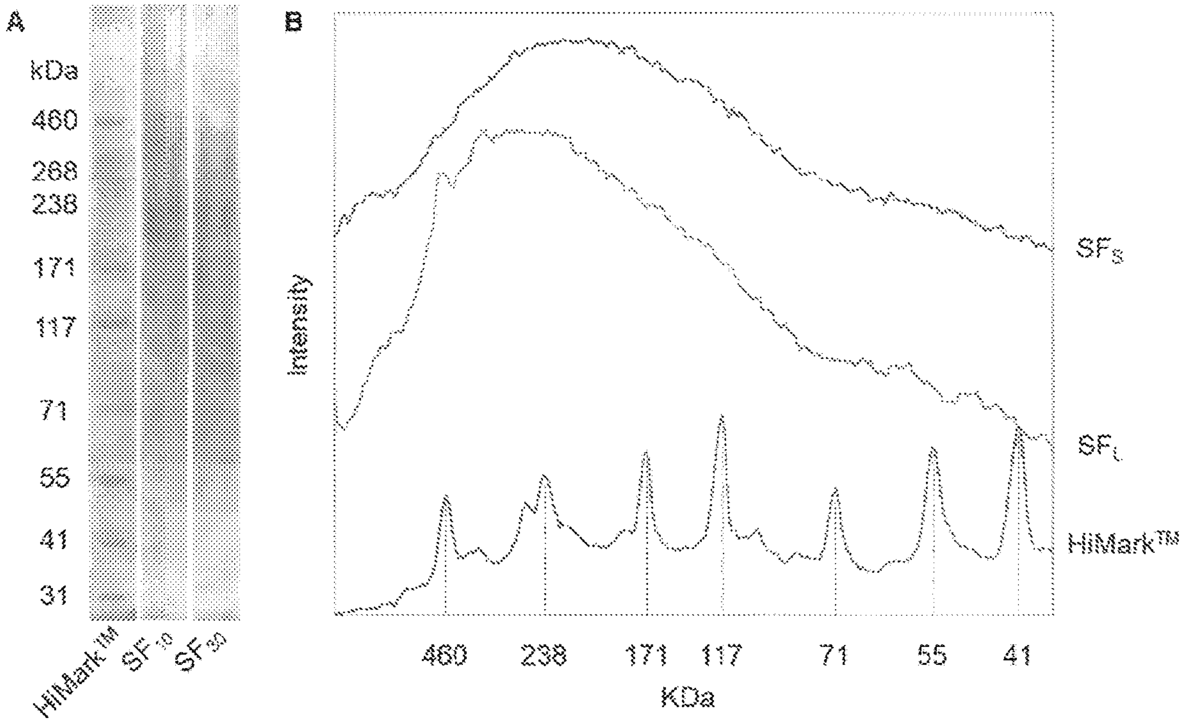
FIG. 2. Sodium dodecyl sulfate-polyacrylamide gel electrophoresis (SDS-PAGE) of pre-stained protein standard (HIMARK™), larger silk fibroin ($SF_L$), and smaller silk fibroin ($SF_S$). (A) Photo images after gel electrophoresis mobility test. (B) Color intensity plots converted from gel images using IMAGEJ.
Figure 3:
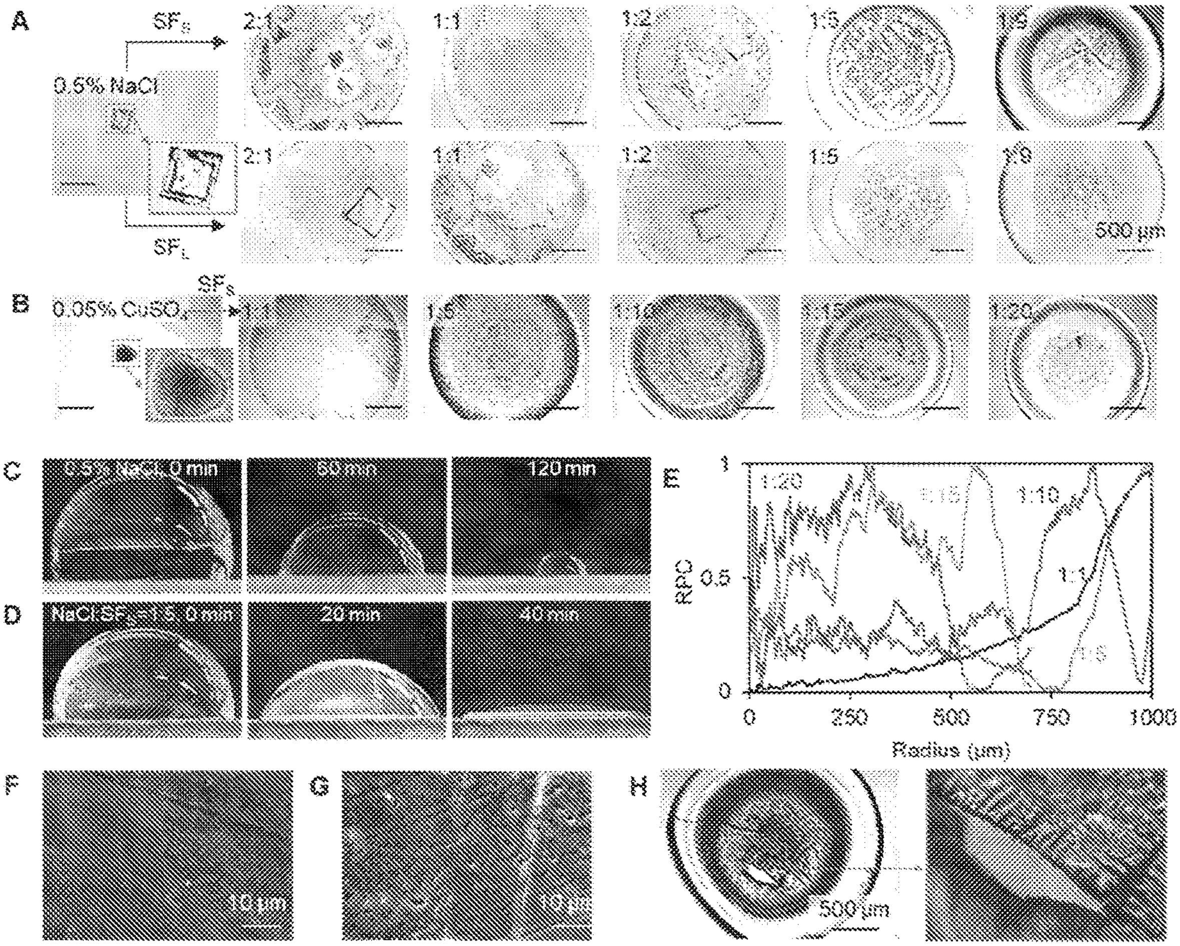
FIG. 3. Crystallization of NaCl and $CuSO_4$ from silk fibroin solutions on flat PDMS surfaces. (A-B) Optical microscope images of 5 μL droplets after evaporation. Initial solutions contained 0.5% w/v NaCl (A) and 0.05% w/v $CuSO_4$ (B) with $SF_S$ and $SF_L$. The ratios are weights of salts to silk fibroins. Scale bars are 500 μm. $CuSO_4$ with $SF_L$ was not tested because of an immediate gelation. (C-D) Side view monitoring of the evaporation of NaCl solution (0.5%, 5 μL) without (C) and with $SF_S$ (NaCl:$SF_S$=1:5, D) on PDMS. (E) The relative particle concentration (RPC) of $CuSO_4$ in images of FIG. 2B along the radial direction. ImageJ (ver 1.53e) was used to calculate the average grey values of pixels at the same distance from the center of the water droplet. The darkest average value was assigned to 1. (F-G) Scanning electron microscope images of the edge area (F) and center area (G) of the silk film prepared from a 5 μL droplet containing 0.1% NaCl and 6% $SF_S$ (NaCl:$SF_S$=1:60) after immersing in 80% ethanol for a day. (H) Optical microscope images of the silk film prepared from a 5 μL droplet containing 0.5% NaCl and 5% $SF_S$ (NaCl:$SF_S$=1:60) after 80% ethanol treatment for a day. The zoomed in image shows a weak interface between the outer ring (silk dominant phase) and the center film (NaCl dominant phase). Scale bar is 500 μm.

We first observed the crystallization of ionic sodium chloride (NaCl) and copper sulfate ($CuSO_4$) by evaporating water droplets containing SF extracted from *Bombyx mori* cocoons. SF solutions with two average molecular weights of ~270 kDa (larger SF, $SF_L$) and ~200 kDa (smaller SF, $SF_S$) were used for comparison (FIG. 2) [25]. Without silk, only a single NaCl or $CuSO_4$ particle formed on the polydimethylsiloxane (PDMS) surface after evaporation (FIG. 3A-B). Due to a high surface energy between the salt solution and the hydrophobic PDMS surface, the contact angle of the droplet (>83° C.) was mostly constant during the evaporation (FIG. 3C). Considering the water solubility of NaCl (36 g in 100 g at 25° C.) 26, homogeneous nucleation would occur after >98% water evaporated from the initial 0.5% solution unless impurities or surface roughness induced heterogeneous nucleation[27]. The reduced droplet volume and high surface tension are favorable conditions for homogeneous nucleation and growth of the cube-like NaCl crystal (hexoctahedral halite, FIG. 3A) or an aggregate particle of elongated $CuSO_4$ crystals (prismatic gypsum, FIG. 3B).

SF reduced the surface energy between the droplet and the PDMS surface, pinning the contact line during evaporation. The contact line kept drawing the solution from the droplet via capillary flow, accumulating the fibroins at the pinned contact line (known as the coffee-stain effect, FIG. 3D) [28,29]. At lower SF concentrations, salt crystals mainly formed near the contact lines (e.g., NaCl:$SF_S$=2:1 and $CuSO_4$:$SF_S$=1:1, FIG. 3A-B) because hydrophilic intermolecular spacers of silk, rich in carboxylic acids that attract ionic precursors to salt crystal [30], serve as a substrate for heterogeneous nucleation with reduced energy barrier [27]. A slight increase in fibroin concentration (e.g., NaCl:$SF_S$=1:1) formed more particles with a smaller size as described by classical nucleation theory-smaller critical nucleus size with reduced energy barrier [31].

The salt formation patterns changed significantly when the initial fibroins concentration increased sufficiently to form a self-standing film (>1%). At these high concentrations, silk fibroins self-assemble into micelles that hydrophobic chains surround hydrophilic intermolecular spacers [32], repelling ionic precursors from the silk-accumulating contact line and forcing the particle formation close to the center of the film (e.g., NaCl:$SF_L$=1:9 and $CuSO_4$:$SF_S$=1:20). The self-standing films became insoluble by increasing the β-sheet structure via ethanol-treatment [33], allowing selective removal of NaCl crystals and generating porous structures (FIG. 3F-G). Increasing NaCl concentration separated weakly bound two phases in the film; a silk-dominant outer ring and a central area with high NaCl inclusion (FIG. 3H), providing a hint for fabricating hollow microneedles.

Structural Manipulation of Microneedles Via Salt Crystallization.

Figure 4:
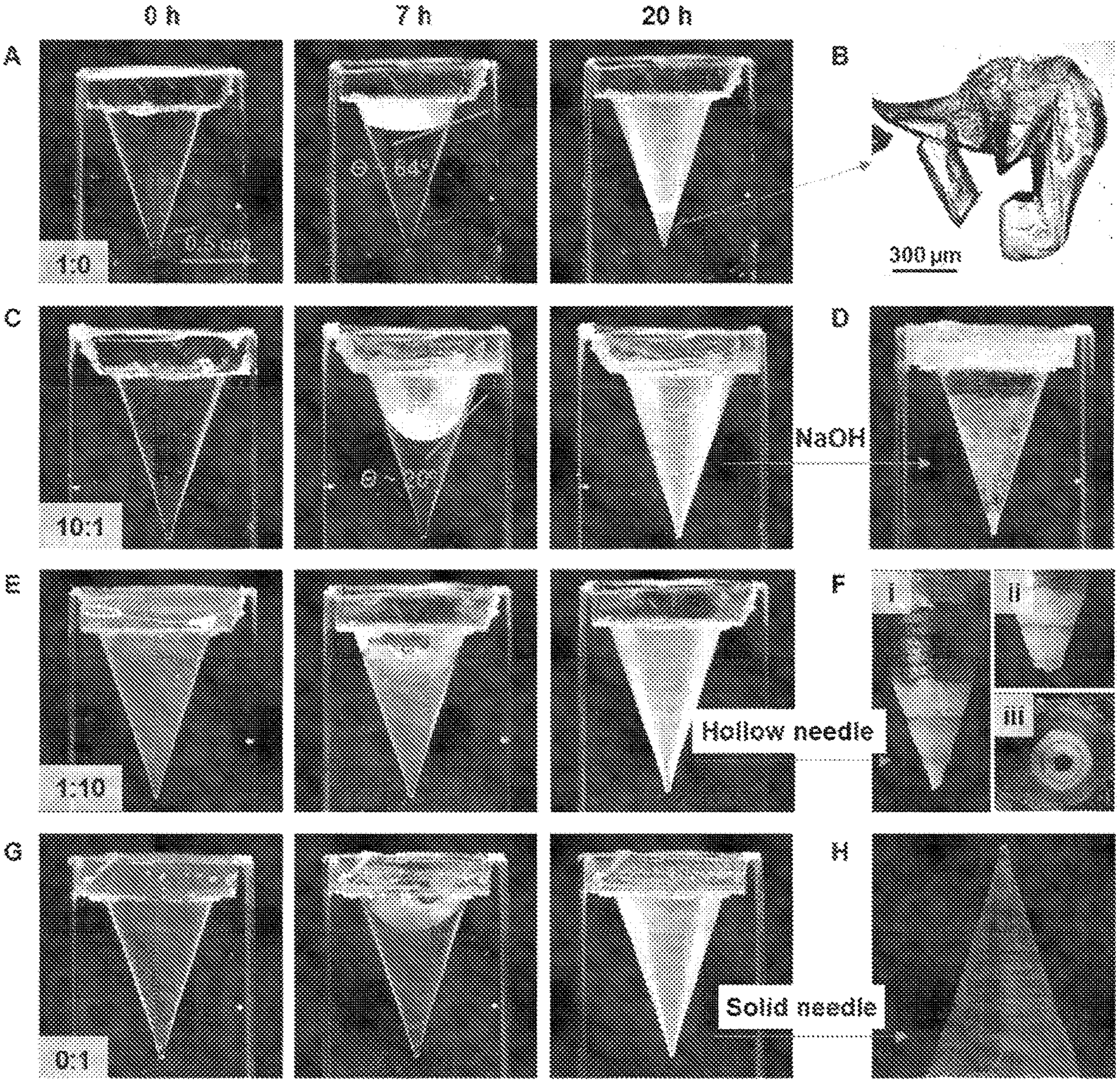
FIG. 4. Crystallization of $CuSO_4$ in silk fibroin solutions during needle formation in a macro PDMS mold (0.6 cm base diameter×0.9 cm long). Photographs of 0.5% $CuSO_4$ solutions evaporating in the mold at 0, 7, and 20 h with $CuSO_4$ to $SF_S$ ratios at 1:0 (A), 10:1 (C), 1:10 (E), and 0:1 (G). (B) Optical microscope of the $CuSO_4$ precipitates from the solution without silk ($CuSO_4$:$SF_S$=1:0). (D) Addition of 0.1 N NaOH to visually Cu distribution by forming copper hydroxide after evaporation of the solution with low silk fibroin concentration ($CuSO_4$:$SF_S$=10:1). (F) At high silk fibroin ($CuSO_4$:$SF_S$=1:10), $CuSO_4$ precipitated heavily at the tip (i) that is easily separated from the column region to form hollow microneedle structure (ii, iii). (H) Solid microneedle with mechanical integrity formed by pure silk solution. 0.005% phenol red is added to solutions with high fibroin concentrations ($CuSO_4$:$SF_S$=1:10 and 0:1).

Using time-lapse photography, we monitored the salt crystallization and silk assembly in a PDMS mold, replicating a macroscale needle (FIG. 4). Hydrated $CuSO_4$ crystals with a clear blue color precipitated at the bottom tip of the mold without SF (FIG. 4A-B). Adding a low amount of SF ($CuSO_4$:$SF_S$=10:1) inhibited the blue particle precipitation (FIG. 4C). Instead, the mold wall was covered uniformly with white residues, presumed to be aggregates of silk fibroins bound with ionic Cu and sulfate species (or invisible $CuSO_4$ particles). Adding 0.1 N NaOH into the dried mold formed blue $Cu(OH)_2$ crystals, confirming that Cu precursors distributed uniformly along the mold wall (FIG. 4D). As shown in the film formation process (FIG. 3C-D), silk fibroins decreased the surface energy, lowering the contact angle from ~64° to ~20° at 7 h (FIG. 4A,C), and induced capillary flow that attached SF with Cu ions to the wall. At a high fibroin concentration ($CuSO_4$:$SF_S$=1:10, FIG. 4E), fibroins assembled into a film covering the entire mold wall, forming a cone-like needle with an empty well inside. Cu and sulfate ions, repelled by micelles forming the silk film, were concentrated in the solution remained in the tip region, leading to a clear separation of the silk-dominant transparent column and the Cu-heavy opaque tip (FIG. 4Fi). The significant $CuSO_4$ inclusion disrupted film integrity; thus, the brittle tip was easily tom off by a slight mechanical force (squeezed with a tweezer), forming a hollow needle structure (FIG. 4Fii-iii). The silk-only solution formed a similar cone-like needle without phase separation or brittle tip formation (FIG. 4G-H).

Figure 5:
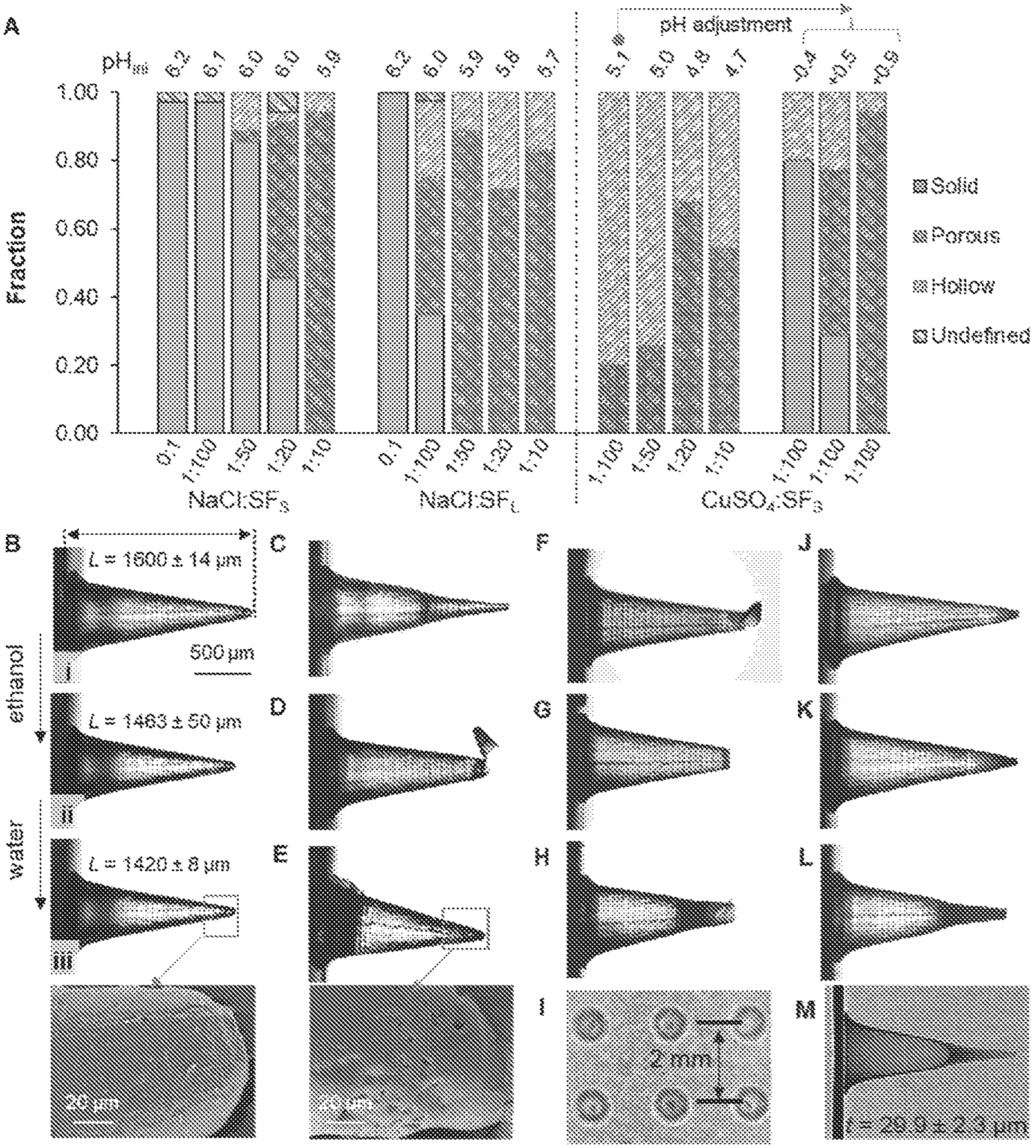
FIG. 5. Microneedle fabrication using $SF_S$ and $SF_L$ with addition of ionic NaCl and $CuSO_4$. (A) Fractions of microneedle types prepared in an array. More than 30 individual needles were observed under microscope to categorize them into solid, hollow, and porous tip structures. (B-E) Representative optical microscope images of microneedles made of $SF_S$ and NaCl. (B) Solid needles (NaCl:$SF_S$=0:1) before (i) and after ethanol treatment (ii), and additional dissolution in water with a zoomed in SEM image (iii). ImageJ (ver 1.53e) was used to analyze the lengths (L) of microneedles from optical images (Mean±SD, N=10). (C) Solid microneedle with a narrow tip (NaCl:$SF_S$=1:50). (D) Hollow microneedle (NaCl:$SF_S$=1:100). (E) Porous microneedle NaCl:$SF_S$=1:50) after ethanol treatment and water dissolution for a day. (F-H) Optical microscope images of hollow microneedle made of $SF_S$ and $CuSO_4$ at $SF_S$:$CuSO_4$=1:100 (F), 1:50 (G), and 1:20 (H). (I) Stereo microscope image (top view) of the hollow microneedle ($SF_S$:$CuSO_4$=1:100). (J-L) Optical microscope images of hollow microneedles made of $SF_S$ and $CuSO_4$ at $SF_S$:$CuSO_4$=1:100 (J), 1:50 (K), and 1:20 (L). (M) Micro computed tomography image of a porous needle ($SF_S$:$CuSO_4$=1:20).

We applied these phenomena to fabricate hollow microneedle arrays using a small PDMS mold (10×10 needles, 600 μm base diameter and 1.6 mm long) with varying concentrations of NaCl and $CuSO_4$ (FIG. 5A). Without any salt, both $SF_S$ and $SF_L$ solutions fabricated an array with cone-like microneedles with empty wells inside, replicating the exact shape and size of the mold (FIG. 5B). This type of microneedle without any opening (solid microneedle, SMN) transports target molecules from or to plant tissues mainly via swelling and diffusion [34]. Crystallizing SMN with ethanol to enhance the stability in wet tissues resulted in ~8.6% reduction in length (FIG. 5B). SMN was the dominant type with $SF_S$ up to 2% NaCl addition (NaCl:$SF_S$=1:50). Tips became narrower with NaCl addition (FIG. 5C), possibly because the concentrated ions could lead silk fibroins to aggregate each other (known as a sticky reptation concept [35]) rather than adhere to the mold wall. At high NaCl concentrations (NaCl:$SF_S$=1:20 and 1:10), a few hollow microneedles (HMN, FIG. 5D) and more porous microneedles (PMN, FIG. 5E) were fabricated. NaCl crystals (<10 μm) sporadically formed at the PMN tip, and their dissolution during ethanol treatment was the main mechanism of the pore generation. With $SF_L$, more fractions of HMN and PMN were appeared in an array at lower NaCl concentration. Because $SF_S$ with a longer chain length have stronger tendency aggregate each other (i.e., larger salt-out effect), thus ionic precursors could be condensed in a liquid phase that promotes nucleation of NaCl crystals and their precipitation at the tip.

Figure 6:
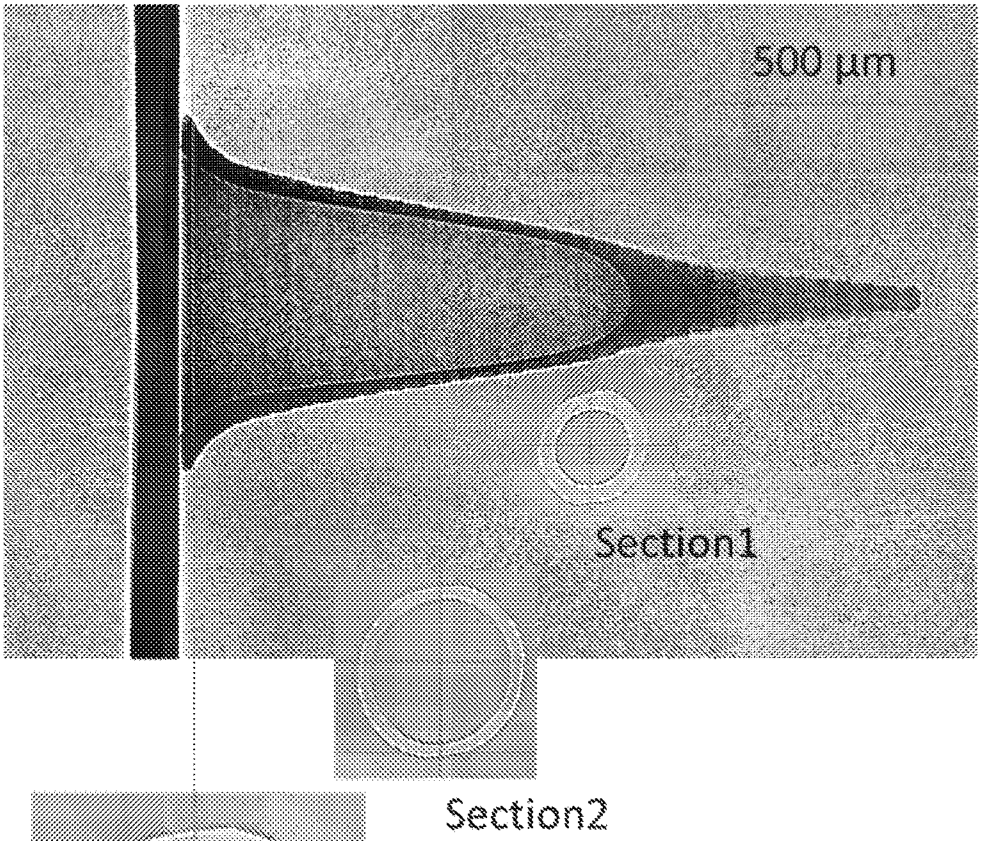
FIG. 6. Measurement of wall thickness of a porous microneedle ($CuSO_4$:$SF_S$=1:20) from the micro computed X-ray tomography image.
Figure 6:
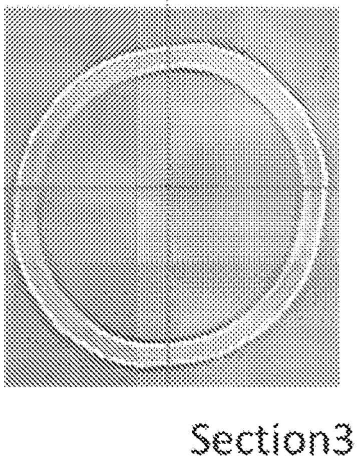
Figure 7:
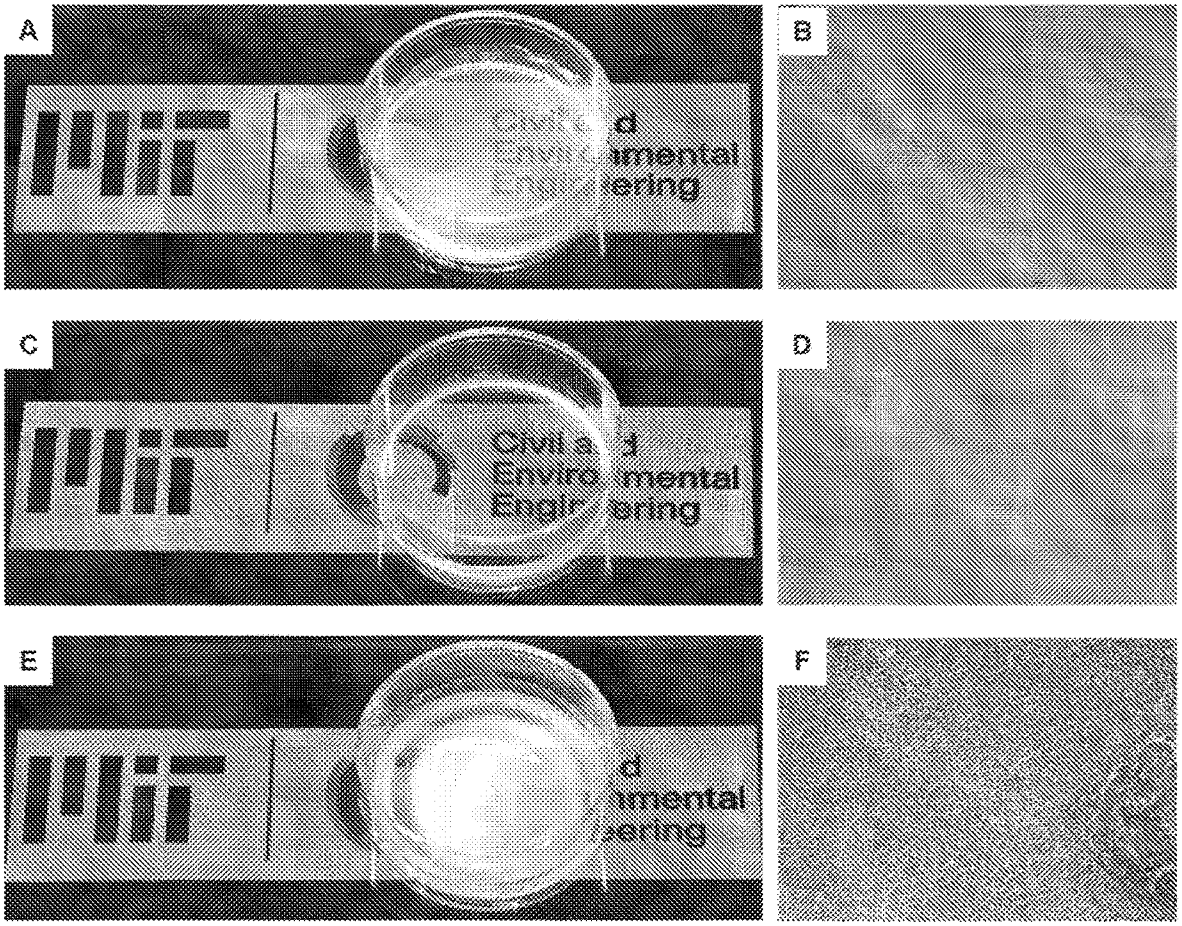
FIG. 7. Photo (A,C,E) and optical microscope (B,D,F) images of films prepared with $SF_S$ with varying weight ratio of ionic $CuSO_4$ in petri-dishes. $CuSO_4$:$SF_S$=0:1 (A,B), 1:10 (C,D), and 1:5 (E,F).

At all ratios, $CuSO_4$ addition resulted in either hollow (FIG. 5F-I) or porous (FIG. 5J-M) structures and Cu-heavy tip regions of both needle types became larger with more $CuSO_4$ addition. The HMN tips were removed or partially detached from the column when being peeled off from the mold while the PMN tips were intact. HMN was the dominant type (>74%) at low $CuSO_4$ concentrations ($CuSO_4$:$SF_S$=1:100 and 1:50). Compared to NaCl, $CuSO_4$ has lower water solubility, inducing nucleation at an earlier time point of evaporation when solution is less viscous. This condition is favorable for $CuSO_4$ nuclei, which are heavier than NaCl nuclei, to precipitate down at the tip. At higher $CuSO_4$ concentrations ($CuSO_4$:$SF_S$=1:20 and 1:10), PMN with narrow tips became dominant. Micro computed X-ray tomography image of a PMN ($CuSO_4$:$SF_{30}$=1:20) shows the middle column part is empty inside with a wall thickness ~30 μm (FIG. 5M and FIG. 6). The opaque narrow porous tip indicates that the concentrated $CuSO_4$ gelled the silk solution at the tips by sticky reptation, inhibiting the formation of HMN due to the limited diffusion of Cu and sulfate ions needed for the growth of $CuSO_4$ crystals. In the case of film formation, gelation, transiting films from transparent to opaque, occurred when at $CuSO_4$:$SF_S$=1:5 (FIG. 7). The gelation might also be affected by the decrease pH by Cu ions that complex with hydroxides as shown in the preventing hollow microneedle formation at $CuSO_4$:$SF_S$=1:100 by artificial decrease in the initial solution pH (FIG. 5A). HMN could not be fabricated more uniformly by intentionally increasing the solution pH, probably because the NaOH injection might locally spike pH, promoting heterogenous $CuSO_4$ nucleation at silk fibroins.

Cu Distribution Along the Microneedle.

Figure 8:
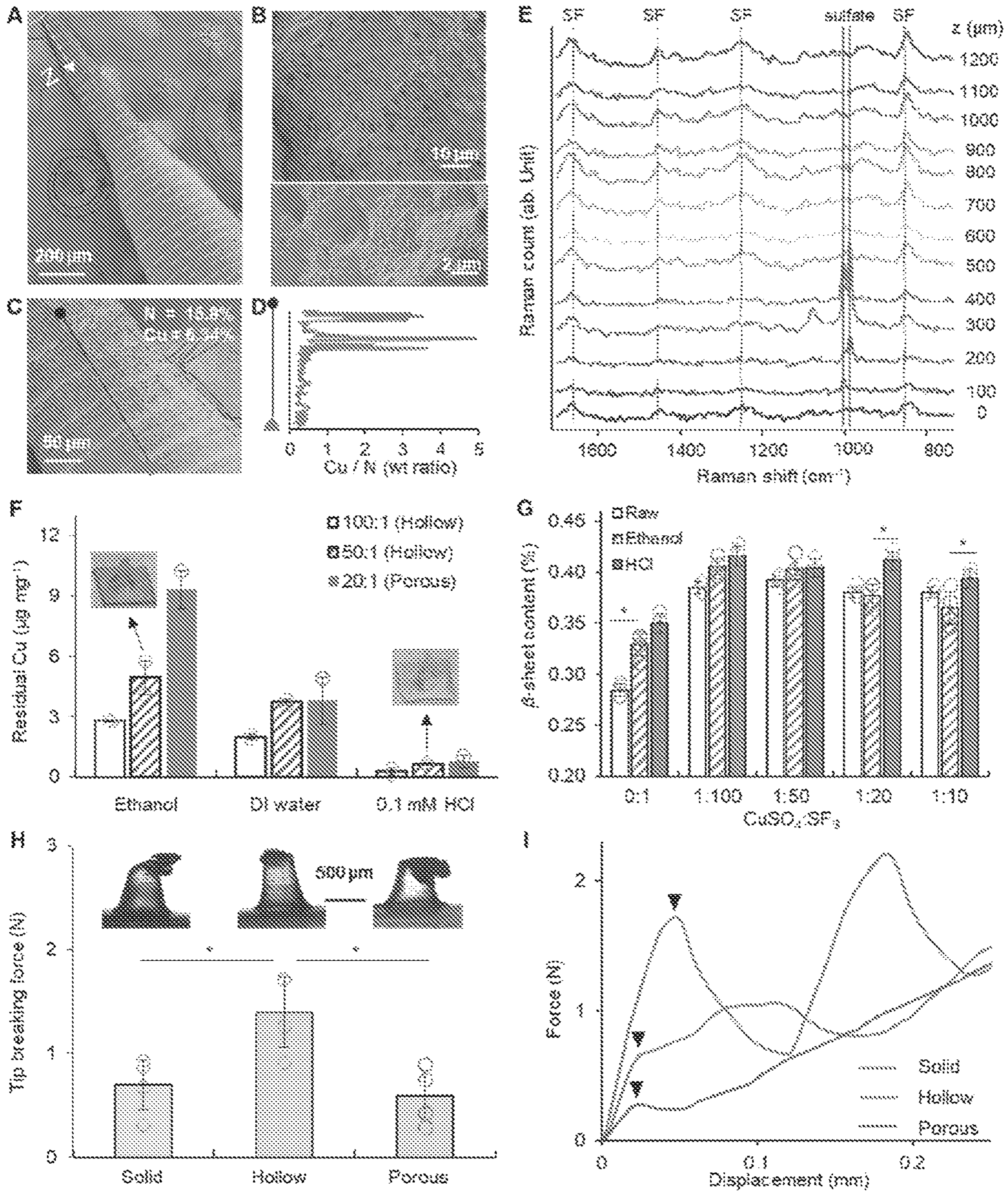
FIG. 8. Characterization of solid, hollow, and porous microneedles with $CuSO_4$. (A-C) SEM images of a porous microneedle ($CuSO_4$:$SF_S$=1:20). (D) A profile of Cu/N weight ratio by SEM-EDX along the line shown in FIG. 5C. (E) Raman spectra collected along z-direction of the porous needle shown in A. Bands corresponds to sulfate minerals and silk fibroins are indicated with solid and dotted lines. (F) Residual Cu concentrations in ethanol-treated hollow ($CuSO_4$:$SF_S$=1:100 and 1:50) and porous microneedles ($CuSO_4$:$SF_S$=1:20) after soaking in deionized water or 0.1 mM hydrochloric acid. Inset images are the hollow microneedle before (left) and after (right) acid wash. (N=2, independent experiments) (G) FTIR analyses for B-sheet contents of $SF_S$ films with $CuSO_4$ prepared in PDMS molds mimicking a microneedle molding environment. Comparison of $SF_S$ films prepared on flat surfaces is in FIG. 11B,C. * symbol is marked when a statistically significance ($p<0.05$) was observed by a treatment (i.e., raw vs. ethanol or ethanol vs. raw) of the film at the same ratio. (N=4 from independent experiments). (H) Initial breaking forces of solid ($CuSO_4$:$SF_S$=0:1), hollow ($CuSO_4$:$SF_S$=1:50), and porous ($CuSO_4$:$SF_S$=1:20) microneedles. Inset optical microscope images are microneedles after mechanical testing. (I) Displacement-force curves from the mechanical testing of three microneedle types with indications of initial breaking points with the black arrows. Bar graphs with error bars in F-G represent means and standard deviations. Red circles are individual data points. One- or two-way ANOVA with the Tukey HSD post-hoc tests were conducted for the statistical comparison.
Figure 9:
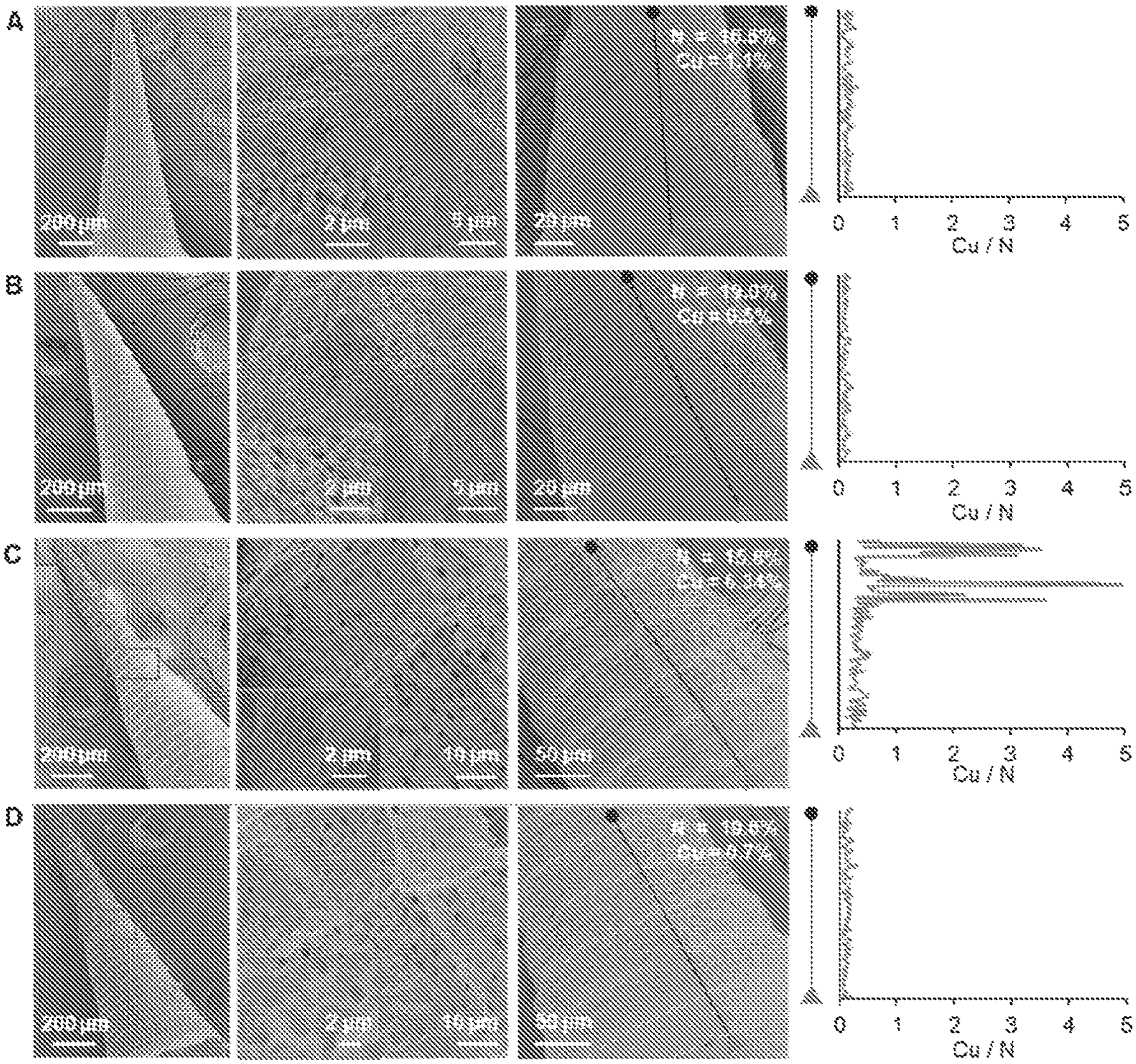
FIG. 9. SEM images of porous microneedles and EDX line profiles of Cu/N weight ratio near the interfaces between porous tips and smooth column regions. (A) Raw porous microneedle with low Cu ($CuSO_4$:$SF_S$=1:100) (B) Porous microneedle with low Cu ($CuSO_4$:$SF_S$=1:100) after ethanol treatment and 0.1 mM hydrochloric acid washing. (C) Raw porous microneedle with high Cu ($CuSO_4$:$SF_S$=1:20). (D) Porous microneedle with high Cu ($CuSO_4$:$SF_S$=1:20) after ethanol treatment and 0.1 mM hydrochloric acid washing.

Considering the consistency in the fabrication, we chose three types of microneedles made of $CuSO_4$ for further evaluating their properties for plant applications: SMN ($CuSO_4$:$SF_S$=0:1), HMN ($CuSO_4$:$SF_S$=1:100 and 1:50) and PMN ($CuSO_4$:$SF_S$=1:20). Scanning electron microscopy/energy dispersive X-ray spectrometry (SEM/EDS) analysis of the porous microneedle ($CuSO_4$:$SF_S$=1:20) shows the clear interface between the Cu-heavy porous tip and Cu-low smooth column regions (indicated as * and *, FIG. 8A-D) at ~600-700 μm above the tip end. Sub-micron $CuSO_4$ crystals were randomly scattered on the tip surface (FIG. 8B), resulting in several spikes in the Cu/N weight ratio profile (FIG. 8C-D). In the Raman spectra obtained along the microneedle outer surface from the tip to the middle column (denoted as z-direction, FIG. 8E), bands corresponding to peak positions of SO symmetric stretches of other $CuSO_4$ minerals (~985-1005 $cm^{-1}$) irregularly observed when the focal spot (700 nm) hit the small particles scattered on the tip. In the middle column region above the interface, no sulfate peaks were detected. Instead, peaks corresponding to silk fibroins, such as Amide I at 1660 $cm^{-1}$ [37], became clearer. The PMN with low $CuSO_4$ ($CuSO_4$:$SF_S$=1:100) has a short porous region (<100 μm), with negligible Cu signals from SEM/EDS (FIG. 9). The pore structures irrelevant to the $CuSO_4$ crystal distribution and low Cu signals support that the pores were mainly generated by SF assembly in the mold under the influence of concentrated Cu ions and pH, rather than dissolution of $CuSO_4$ precipitates. The pores from the particle dissolution were only partially appeared at the PMN ($CuSO_4$:$SF_S$=1:100) tip end after weak acid rinse of the (FIG. 9A-B).

Figure 10:
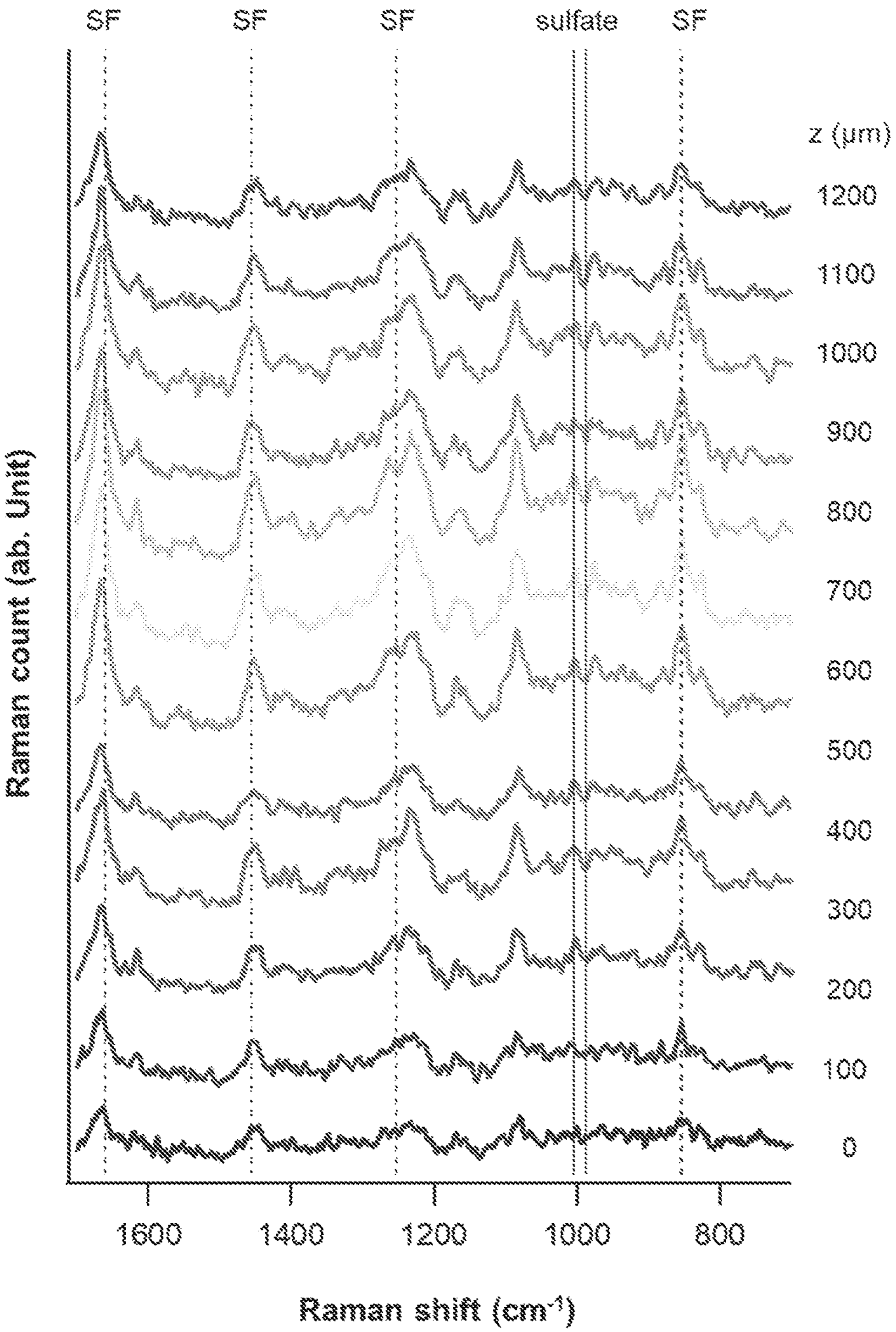
FIG. 10, Raman spectra collected from the porous microneedle ($CuSO_4$:$SF_S$=1:20) after ethanol treatment and 0.1 mM hydrochloric acid washing as a distance from the tip end. Bands corresponds to sulfate minerals and silk fibroins are indicated with solid and dotted lines.
Figure 11:
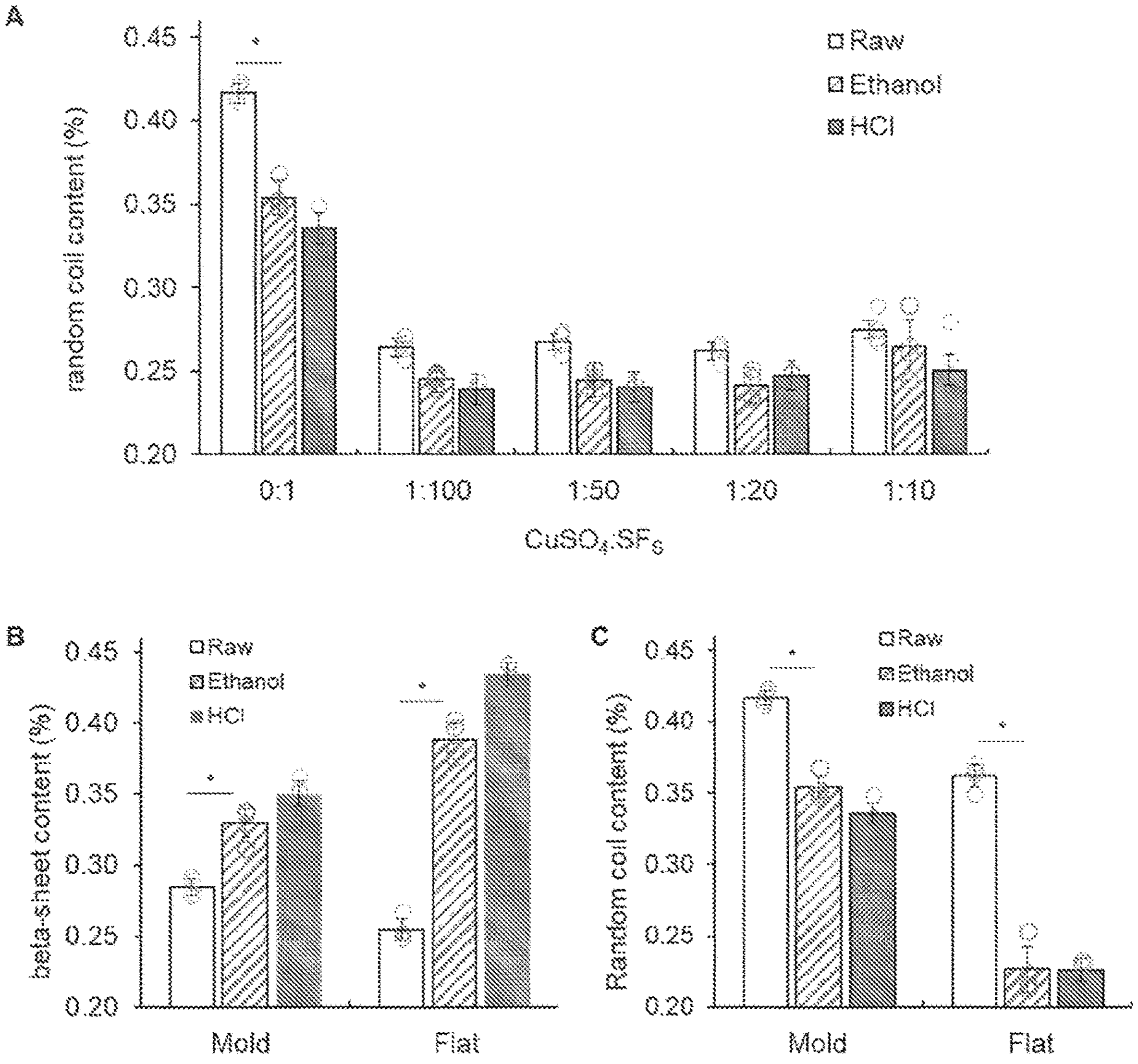
FIG. 11. FTIR analyses of $SF_S$ films. (A) Random coil contents in $SF_S$ films with $CuSO_4$ prepared in PDMS molds with a rectangular well ($1\times1\times0.3$ $cm^{-3}$). (B-C) Comparison of beta-sheet and random coil contents in pure $SF_S$ films ($CuSO_4$:$SF_S$=0:1) prepared in PDMS molds and flat PDMS surfaces. Films prepared in the flat surfaces show more drastic changes in β-sheet structures by ethanol treatment and acid washing compared to the films prepared in the mold due to the smaller sample thickness (136.7±12.5 μm vs. 51.3±9.0 μm) and faster water evaporation rate (40.4 mg $h^{-1}$ vs. 21.8 mg $h^{-1}$). Bar graphs with error bars represent means and standard deviations. Circles are individual data points. Two-way ANOVA with the Tukey HSD post-hoc tests were conducted for the statistical comparison. N=4 from independent experiments.

Cu is one of the plant micronutrients with an adequate concentration of 600 ng per gram fresh weight [38,39] and has been widely used in antimicrobial compounds for crop protections more than a century [40]. Cu is also an essential mineral present in natural foods, such as beef, and also available as a dietary supplement with 900 μg of Daily Value for adults [41]. The ethanol-treated PMN ($CuSO_4$:$SF_S$=1:20) contains ~10 μg Cu per mg of microneedle (FIG. 8F). It means that one PMN (~0.76 mg) can supply adequate Cu in 13 g of fresh plant and total Cu in 115 PMNs is equivalent to the Daily Value. Thus, we do not consider that Cu in this PMN and other HMNs prepared with lower amount of $CuSO_4$ would cause significant concern for food/agricultural and biomedical applications. Moreover, Cu was easily removed from the PMN by ~60% and ~90% after washing with deionized water and weak acid, respectively, without significant morphological change (FIG. 8F). The acid wash changed the microneedles' original blue color to transparent by the removal of $CuSO_4$ crystals, as also confirmed by SEM/EDS and Raman spectra analyses (FIG. 9B,D and FIG. 10). The weak HCl treatment slightly increased β-sheet contents in silk films because of dissolution of small portion of soluble regions (random coil dominant) (FIG. 8G and FIG. 11A). However, the treatment did not affect the secondary protein structures significantly, especially when prepared with lower amount of $CuSO_4$. Instead, the β-sheet contents were more influenced by Cu addition and consequent pH decrease, showing a maximum at $CuSO_4$:$SF_S$=1:100, which is consistent with a previous report [42]. Increased β-sheet by ethanol treatment was less effective for films with $CuSO_4$ compared to pure silk films (FIG. 8G and FIG. 11B,C).

Hollow Microneedles for Plant Applications.

Figure 12:
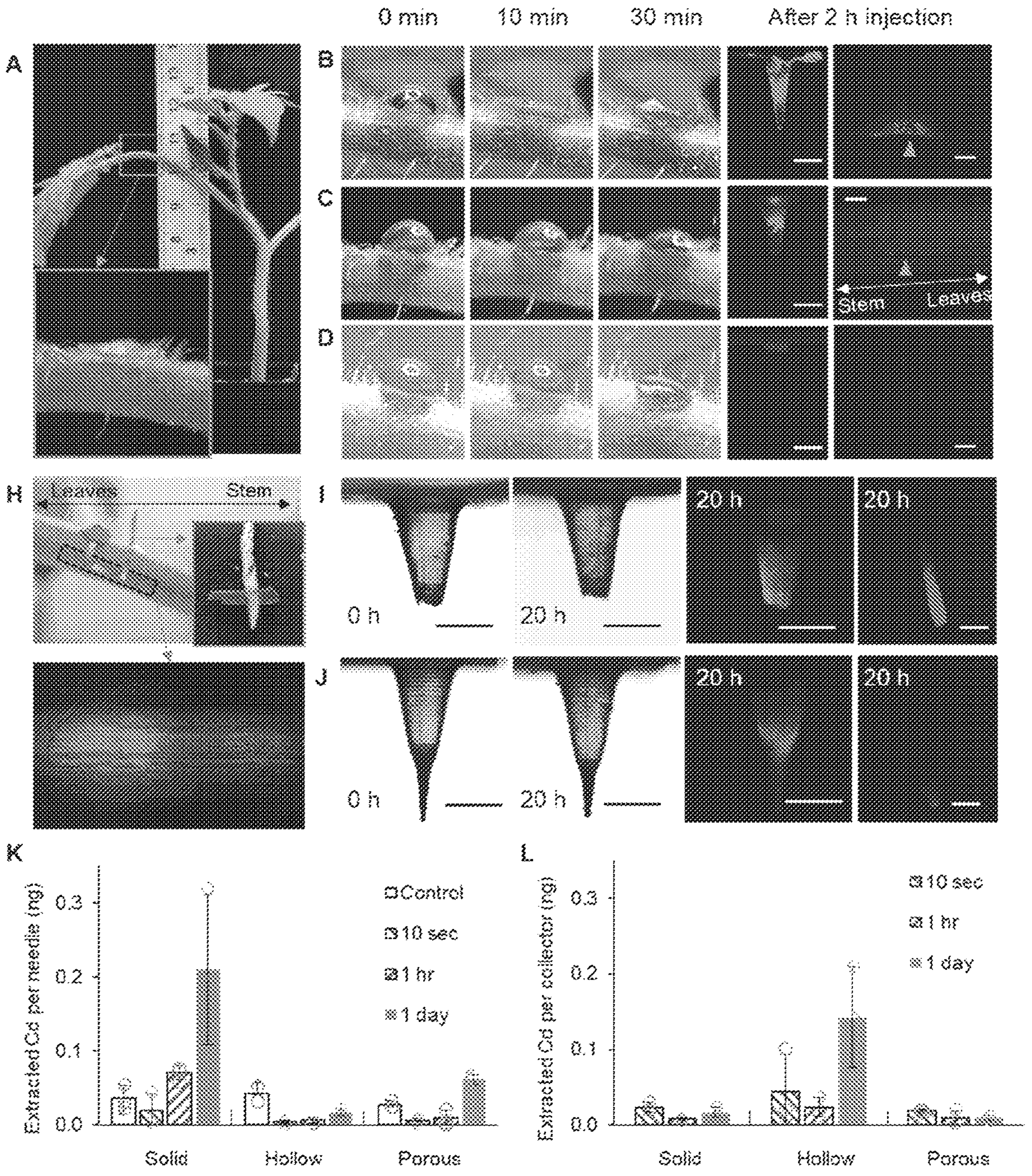
FIG. 12. Microneedle applications to tomato plants. (A) Microneedle injection into tomato petiole about 10 cm above the root. (B-D) Gravitational delivery of biomolecules to plants through the solid (B, $CuSO_4$:$SF_S$=0:1), hollow (C, $CuSO_4$:$SF_S$=1:20), and porous (D, $CuSO_4$:$SF_S$=1:20) microneedles. Photo images were collected from the microneedles injected into tomato petiole after placing 2.5 μL droplets containing 0.2% sodium fluorescein. Fluorescence microscope images of the microneedles and injection spots in the petioles were obtained after 2 h of injection. (H-J) Combination of gravitational delivery and accumulative sampling. (H) Fluorescein (2.5 μL droplets containing 0.2% sodium fluorescein) was delivered to plants through the hollow microneedle ($CuSO_4$:$SF_S$=1:50). After being transported via phloem, fluorescein was extracted from the microneedles and accumulated in tissue paper. Optical images of hollow (I, $CuSO_4$:$SF_S$=1:50) and porous (J, $CuSO_4$:$SF_S$=1:20) microneedles before and after 20 h of the sampling. Fluorescence images are microneedles and tissue paper collectors after sampling. (K-L) Cd extraction using one microneedle (K) and attached tissue paper (L) applied to a petiole of tomato plant growing in a plant medium containing 1 mg $L^{-1}$ Cd. Bar graphs with error bars represent means and standard deviations. Circles are individual data points (N=3, independent experiments).

Mechanical testing of ethanol-treated microneedles showed that the initial breaking forces of HMN were statistically higher than other two types (1.40±0.39 vs. 0.64±0.26, FIG. 8H). The tips of SMN and PMN broke by bending due to the unavoidable lateral force exerted during compression [22], which smoothly declined the force-displacement curve after the initial failure (black arrows in FIG. 8I). On the other hand, HMN broke by the step-by-step collapse of the column region, causing sudden drops and rebounds of the curves (FIG. 8I). Regardless of the breaking patterns, the measured breaking forces from all three microneedle types were more than an order of magnitude higher than forces required to penetrate of model plant tissues [22], including tomato petioles used in this study (FIG. 12).

We applied droplets containing a model biomolecule, fluorescein on the backside of these microneedles injected into tomato petioles (FIG. 12B-D), expecting the droplets to gravitationally fall into the well inside the microneedles and spread in the petioles. This approach, considered as a microneedle version of trunk injection suitable for small plants or at early stage of the growth, has a potential to overcome the limitation in small pre-loaded cargo volumes of current degradable microneedles [39]. The SMN absorbed the droplets most quickly, however, fluorescein only locally spread near the injection spot in the petiole after 2 h (FIG. 12B). Although the droplet absorption was slower, HNM obviously improved the fluorescein dispersion into the plants because its injection created a direct open channel between the penetrated petiole and inner surfaces of the microneedles [34], allowing the fluorescein diffusion directly from the droplet to the plant sap without passing through the microneedle. PNM was most inefficient for delivery, because in most cases, the droplet was dried out on the backside, not absorbed into the microneedles. $CuSO_4$ inclusion increased the β-sheet contents (FIG. 8G) that made the microneedles surface more hydrophobic. In addition, the additional β-sheet formation and $Cu^{2+}$ crosslinking can improve the binding affinities between silk fibroins, thus HMN and PMN would swell less upon the injection, inhibiting the absorption of droplet placed on the backside. In the case of HMN, the inner well became easily wet upon the injection into petioles, thus the droplet could be dispersed more easily. The surface treatment of PMN with hydrophilic polymers or plasma treatment may improve the delivery efficiency by assisting the droplet to sit inside the inner well.

Using one HMN as a source of payload supply, we injected second HMN 0.5 cm downstream from the source for the sampling purpose (FIG. 12H-I). Fluorescein from the source HMN transported through a vascular tissue, phloem, was successfully extracted by the HMN over 20 h. Moreover, we were able to accumulate additional fluorescein in a rolled-tissue paper, as an attachable collector, inserted in the well of HMN from the backside. PNM was able to extract fluorescein from the source HMN, however, it was less effective to deliver fluorescein to the tissue paper (FIG. 12J).

Figure 13:
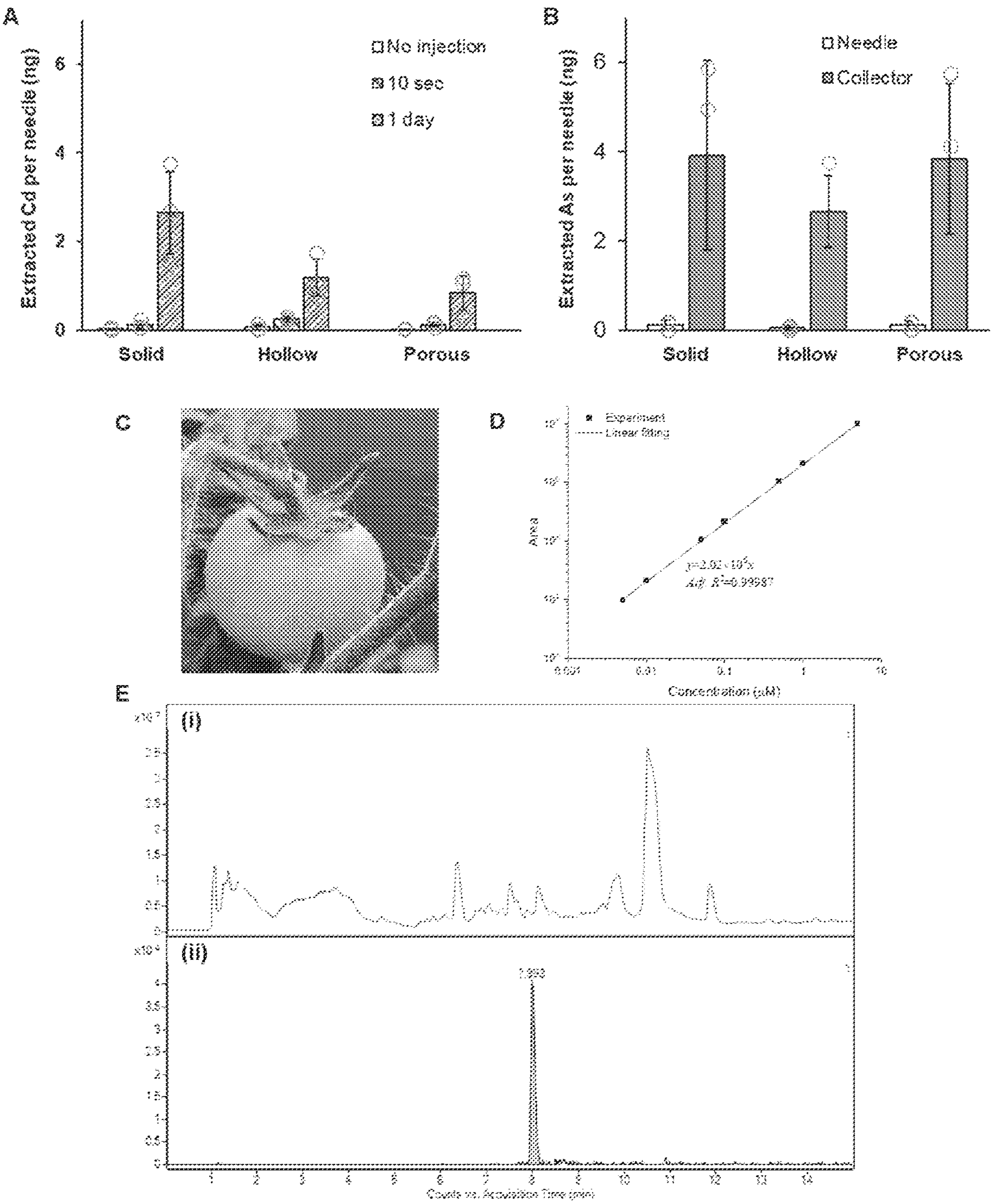
FIG. 13. (A) Cd extraction using one microneedle injected to a petiole of tomato plant growing in a plant medium containing 1 mg $L^{-1}$ Cd. As a control, porous needles injected into the plant without Cd spike extracted 0.03±0.02 ng Cd per needle. (B) As extraction using one microneedle and attached tissue paper as a collector applied to a petiole of tomato plant growing in a plant medium containing 1 mg $L^{-1}$ As for 3 days. Bar graphs with error bars represent mean and standard deviation. Circles are individual data points (N=3, independent experiments). (C) A microTom tomato fruit with a hollow microneedle injected on its pedicel. Vitamin B12 solution is delivered through the hollow microneedle to the fruit. (D) Standard curve for Vitamin B12 detection using LCMS. (E) (i) Total Ion Chromatogram of the whole fruit extract and (ii) the extracted ion chromatogram corresponding to Vitamin B12 with a retention time 7.993 minute.

These microneedles were also evaluated for sampling of Cd and As from plant sap because their bioaccumulation in agricultural products are major concerns even at lower concentrations in water sources [43]. A single SMN injection into petiole effectively extracted Cd (~0.21±0.10 ng Cd per needle equivalent to ~0.27 ng Cd per mg of needle) for a day from the tomato plant exposed to 1 mg $L^{-1}$ Cd in a plant medium (FIG. 12K). Cd captured in SMN was more than 50 time higher than the Cd accumulated in the leaves (0.005 ng per mg dry leaf). Both HMN and PMN did not extract Cd in a detectable level because of their limited swelling capacity. However, we were able to extract ~0.14±0.07 ng Cd per attached collector to HMN, proving that HMN performed as an effective channel between the plant sap and the collector. HMN and PMN extracted up to 1.8 and 1.2 ng Cd per needle, although less effective than SMN, from the tomato plants exposed to 10 mg $L^{-1}$ Cd (FIG. 13). Due to the poor detection limit, none of microneedles and attached collators extracted significant amount of arsenic (As) from the plants exposed to 1 mg $L^{-1}$ As for a day of injection. However, after 3 days of injection, the collectors attached to SMN, HMN, and PMN extracted 31.2, 47.5, and 29.6 times more As than the needles themselves (0.16, 0.07, and 0.17 ng $mg^{-1}$, respectively, FIG. 13) which were 15 times higher than As accumulated in the leaves (0.009 ng $mg^{-1}$). No significant damages in plant health, such as leaf withering, was observed during the three days of Cd and As extraction experiments except for scars left behind the injection. Altogether, the results highlight the potential of single microneedle application for the early prediction of bioaccumulation of toxic contaminants existing at low concentration in the environment.

Vitamin $B_{12}$ is crucial in many physiological activities, including DNA synthesis, red blood cell production, and neurologic function. However, the prevalence of Vitamin $B_{12}$ deficiency is pretty high, particularly in developing countries. In addition, Vitamin $B_{12}$ cannot be obtained from common vegetables, which raises a health concern for vegans. Therefore, we also selected Vitamin $B_{12}$ as a model payload and delivered it to tomato fruits via HMNs injected on stem, pedicel, and sepal (FIG. 13C-E).

Conclusions and Outlook

Monitoring toxic elements that are being bioaccumulated in agricultural products, such arsenic in rice, can enhance food safety reduce chemicals, energy, and water for growing unqualified products. Despite progress in the field, delivering large amount of payloads, such as macronutrients, and sampling targets at low concentration are still challenging. In this study, we presented a simple and straightforward strategy of fabricating degradable polymeric hollow microneedles that are stably operated in plant tissues for the continuous cargo delivery from external sources and accumulative collection. By controlling the kinetics and extents of formation of nanocrystals and the phase front silk fibroin assembly, we were able to manipulate tips into different structures, enabling target-specific application that can effectively tackle this challenge. Beyond the direct application for sampling and delivery, the structures of HMN and PMN with the large well space connected to plant tissues PERMIT coupling with electrochemical or optical sensors for in vivo signal detection [45,46].

Concentrations of metallic ions, such as $K^+$ and $Ca^{2+}$, vary significantly along with the silk glands at different spinning stages to regulate the storage condition of silk fibroins and the mechanical properties of silk fibers upon spinning [35,52]. Therefore, adding ionic salts in regenerated silk fibroin solution is an effective option to decorate the properties of silk-based materials. Typical silk fabrication processes involve water evaporation that drives the assembly of fibroins. Therefore, the added ions are concentrated and eventually nucleate salt crystals. However, little information is available regarding the influence of salt concentrations and their crystallization on the assembly of silk fibroins or vice versa, the influence of the silk fibroin assembly on salt crystal formation. The strategy of controlling microneedle structures using chemical reactions at phase front of silk assembly and inorganic nanocrystal nucleation expands microneedle application for more complex systems beyond the transdermal patches, contributing to designing new functional hybrid materials.

Example 2

Tubular structures at the nanoscale possess significant advantages in a broad range of areas, such as catalysis, sensing, microencapsulation, selective mass transport, filtration and drug delivery, to name a few. While the fields of carbon nanotubes and nanotubes made of several non-carbon materials (e.g., metals, oxides, semiconductors) have been progressing rapidly, polymeric nanotubes is much more limited. Here, we integrate a template wetting approach with multiple silk-based solutions, and present a rapidly scalable and robust technology for fabricating large arrays (up to 20×20 cm) of well-aligned 1D nanostructures made of silk proteins. Benefitting from the polymorphic nature of silk, precise control over the size, density, aspect ratio, morphology (nanotubes versus nanopillars) and polymorphs of silk nanostructures are achieved, which then allows for programmable modulation of the end materials' functions and properties (e.g., hydrophobicity, oleophilicity and gas permeability). The silk nanotube arrays fabricated present great utility as anti-fouling coatings against marine algae, in oil extraction from oil-water mixtures, and as a packaging material with improved gas barrier property.

The preparation of nanoscopic tubular objects and more importantly their organization into macroscopic (at least centimeter scale) arrays is a nontrivial task, especially for soft polymeric materials that are more appropriate to work at the biotic/abiotic interface.

Here we describe a robust approach for fabricating centimeter-scale arrays of well-aligned 1D nanostructures made of silk proteins. The process starts with the employment of commercially available nanoporous polycarbonate membranes as sacrificial templates which can be infiltrated by silk solutions, followed by materials assembly in the confined space of nanopores. Through regulating the biopolymer formulation thereby changing its surface energy, infiltration of the silk-based solution results in either wetting of the pore walls by a mesoscopic precursor liquid film or complete filling of the pore interior, generating large arrays (up to 20×20 cm) of well-aligned silk nanotubes or nanopillars, respectively, after template removal in a polycarbonate-dissolving solvent (e.g. dichloromethane). Integration of the template wetting approach with the versatility of silk materials allows for precise control over the size, density, aspect ratio, morphology (single- and multi-walled tubes, solid and porous pillars, as well as mushroom-shaped structures) and polymorphs of silk nanostructures, which serves as the basis for programmably regulating the end materials' functions and properties (hydrophobicity, oleophilicity and gas permeability). Moreover, the silk nanotube/pillar arrays can either be grown directly on an external substrate (e.g. glass) as a coating material or be fabricated as a free-standing film, offering great flexibility in their utility. Together, the proposed technology represents a paradigm shift in nanofabrication with structural biopolymers, as it enables rapidly scalable manufacturing of nanostructured biopolymer arrays with programmable morphologies, properties and functions by design, which are unattainable with previous similar endeavors (e.g. electron-beam lithography to generate silk nanostructures).

Results and Discussion

Fabrication of Nanotube/Pillar Array Through Wetting of Nanoporous Templates

Figure 14:
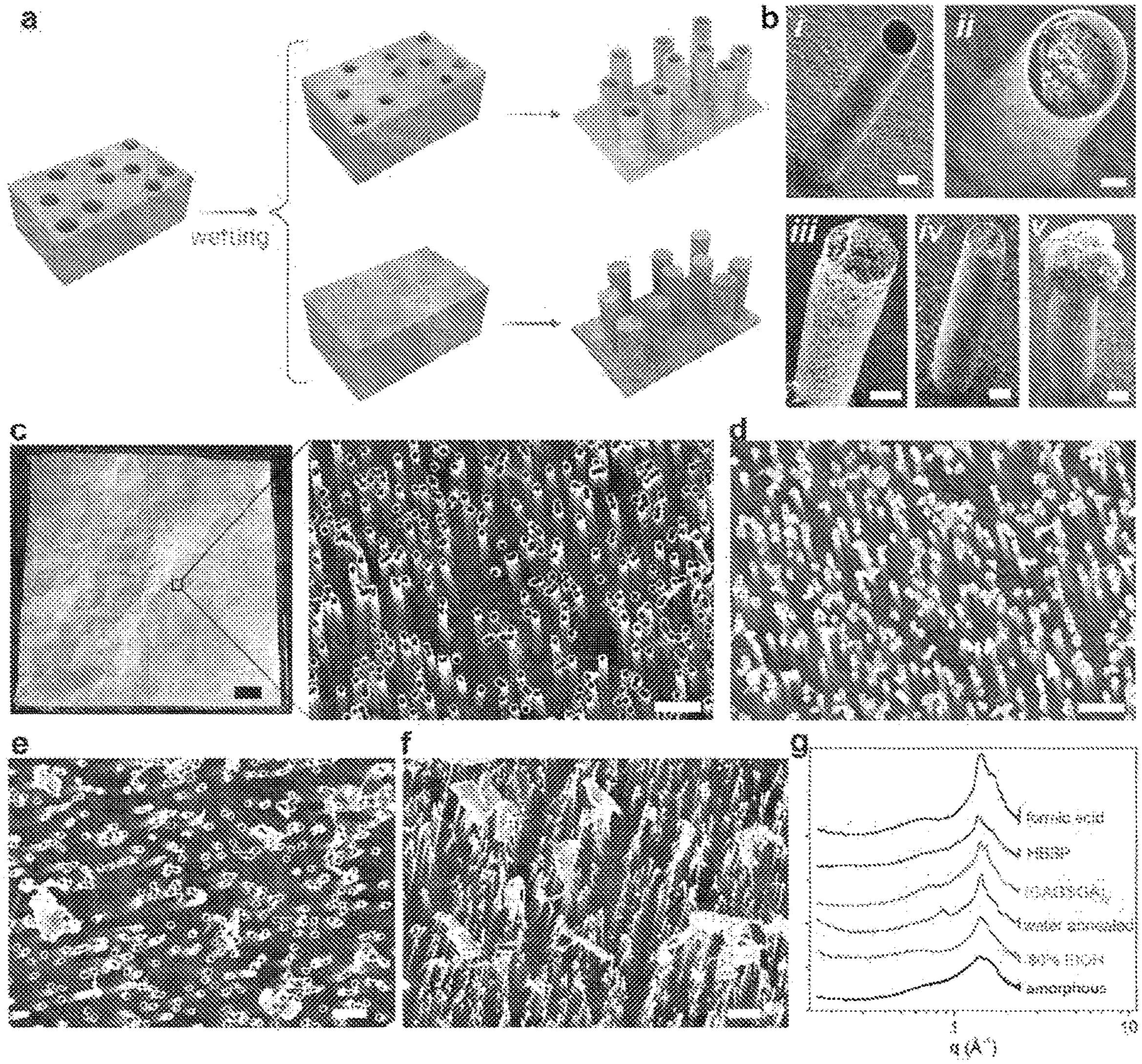
FIG. 14. Fabrication of silk nanotube/pillar array through wetting of nanoporous polycarbonate (PC) membranes. a, Schematic of the template wetting approach to generate either silk nanotube or nanopillar array through different wetting behaviors. b, SEM images of (i) silk nanotube, (ii) silk nanotube-$CaCO_3$ composite, (iii) porous nanopillar, (iv) solid nanopillar, and (v) mushroom-shaped pillar, obtained from the template wetting process shown in a. Scale bars, 500 nm. c, A 20×20 $cm^2$ self-standing silk nanotube array templated from PC membranes of 1 μm pore size and its microscopic view under SEM. Scale bars, 2 cm (left) and 5 μm (right). d, An array of silk nanopillars templated from PC membranes of 1 μm pore size. Scale bar, 5 μm. e, An array of silk nanotubes of tube diameter 400 nm. Scale bar, 2 μm. f, An array of silk nanotubes of tube diameter 100 nm obtained by critical point drying. Scale bar, 2 μm. g, WAXS spectra of silk nanotube arrays made of different silk polymorphs.
Figure 18:
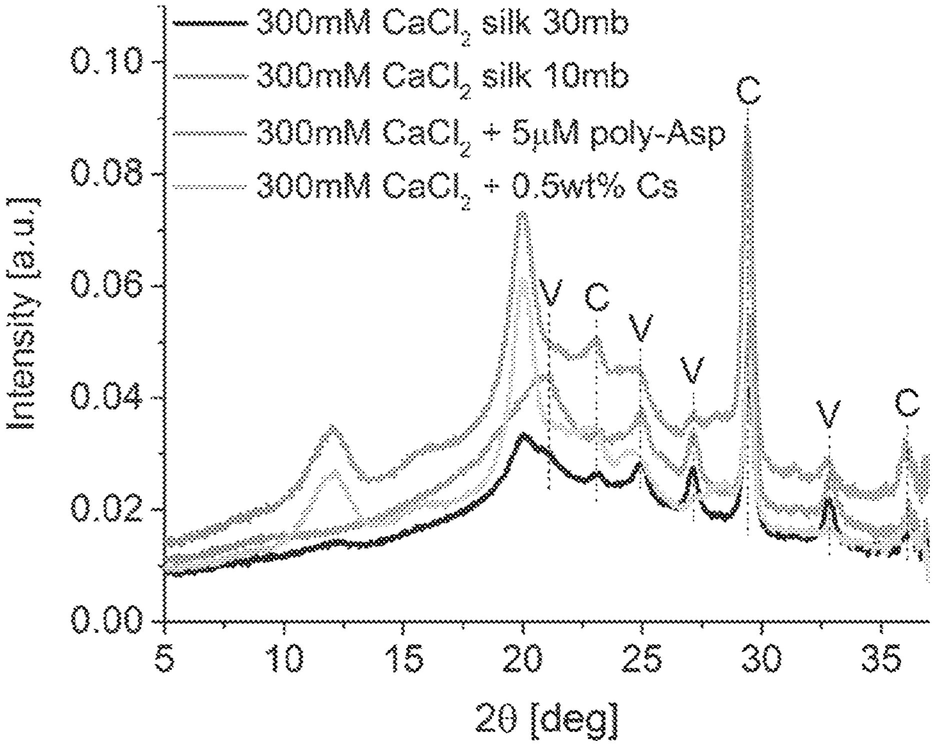
FIG. 18. WAXS spectra of $CaCO_3$ crystallized in silk nanotubes of 1 μm diameter, showing different composition of $CaCO_3$ phases (i.e. calcite and vaterite) depending on the crystallization environment: (i) $CaCl_2$) mixed with 10 minutes boiled silk (high molecular weight); (ii) $CaCl_2$ mixed with 30 minutes boiled silk (medium molecular weight); (iii) $CaCl_2$ mixed with 30 minutes boiled silk and 5 μM poly-Aspartic acid; and (iv) $CaCl_2$ mixed with 30 minutes boiled silk and 0.5 wt % Cs (Cs is a mixture of negatively charged peptides isolated from silk fibroin's non-repetitive domains through a-chymotrypsin digestion).

The general silk nanotube/pillar fabrication procedure is shown in FIG. 14*a*. Here we chose the commercially available polycarbonate (PC) membranes as our nanoporous templates for silk nanotubes/pillars fabrication. The choice of PC membranes is based on their availability in a wide range of pore sizes from several microns down to 10 nm, at a much lower cost compared to other commonly used nanoporous templates (i.e., anodic aluminum oxide and macroporous silicon) and the good wettability of their PVP-coated pore walls by silk-based solutions. As reported by previous studies, wetting of the pore walls of a nanoporous template can occur via either formation of a mesoscopic precursor liquid film or complete filling of the pore interior, depending on the surface energy of both the liquid and the pore wall.[7] Based on this principle, we designed several solution formulations to regulate the wetting and dehydration dynamics, so that different morphologies of the silk nanostructures can be achieved in the end. It was found that both silk-water suspension and silk suspended in formic acid (FA) infiltrate the PC pores through formation of a thin liquid film around the pore walls (FIG. 14*a,i*), generating tubular structures after solvent evaporation. The reason for this phenomenon is because the adhesive forces between silk solution and the pore walls (which drive the spreading) are much stronger than the cohesive forces between silk molecules away from the pore walls (i.e. in the bulk). Therefore, complete filling of the pore interior happens on a much slower time scale than precursor liquid film formation followed by solvent evaporation from that liquid film. With the silk nanotubes obtained (FIG. 14*b,i*), inorganics (e.g. $CaCO_3$) crystallization can be pursued in the confined cylindrical pores (FIG. 14*b*,ii), generating silk-$CaCO_3$ composite with the possibility to control the phase composition of $CaCO_3$ (i.e. calcite and vaterite) (FIG. 18), as silk is known to be able to interact with amorphous calcium carbonate and template their crystallization.

Figure 19:
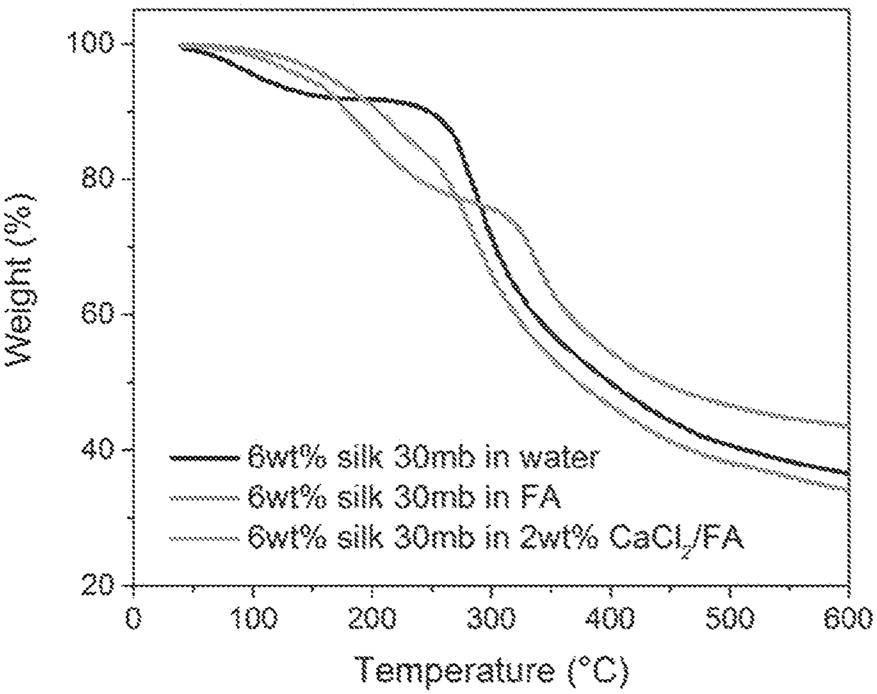
FIG. 19. Thermogravimetric analysis of silk materials dried from different solutions: (i) as-prepared regenerated silk fibroin-water suspension; (ii) silk foams lyophilized from silk-water suspension re-suspended in formic acid (FA); and (iii) degummed silk fibers suspended in FA and 2 wt % $CaCl_2$. The residual water in silk arrays dried from silk-water suspension is mainly free water, as evidenced from the significant weight loss up to around 150° C. where the weight loss starts to level off; silk arrays dried from both silk-FA suspension and silk-$CaCl_2$/FA suspension contain a decent amount of bound water, as shown by the sharp weight loss in the 150-240° C. region which corresponds to evaporation of freezing bound water. Besides, $CaCl_2$ as a highly hygroscopic compound helps to tightly retain a large amount of bound water in the dried silk arrays, further increasing the temperature required to completely remove the residual water to around 310° C.
Figure 20:
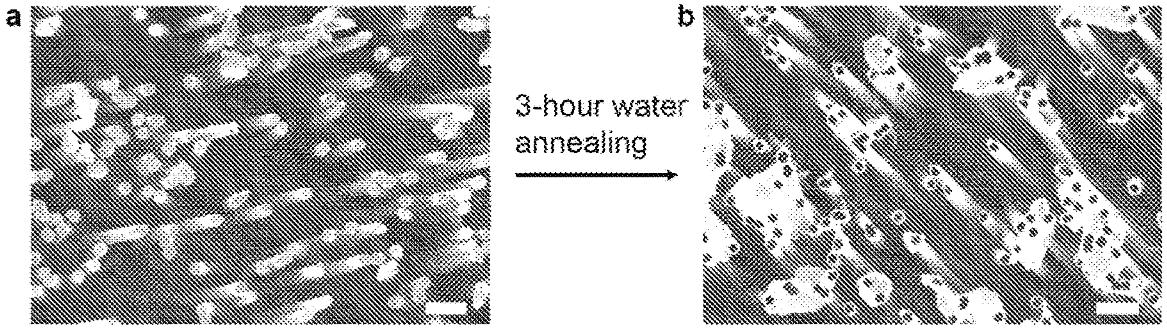
FIG. 20. Morphological transformation from pillar to tube structures. a, Silk nanopillar arrays of 600 nm pillar diameter made from wetting of PC templates by silk-$CaCl_2$/FA suspension. b, silk nanotube arrays obtained by exposing the nanopillar arrays in a (confined in PC templates) to water vapor (99% RH) for 3 hours. Scale bars, 2 μm.

In order to obtain pillar structures out of the PC templates, complete filling of the PC pore volume is required (FIG. 14*a*, ii). This can be achieved by adjusting the formulations of silk solutions to be infiltrated, which results in different morphologies of silk nanopillars in the end materials (FIG. 14*b*, iii-v). In the first method, porous PC templates were infiltrated with a freshly prepared mixture of silk proteins, horseradish peroxidase (HRP) and hydrogen peroxide ($H_2O_2$), then incubated in a humid environment (99% RH) to prevent water evaporation from the silk solution, allowing sufficient time for the silk solution to fill up the entire pore volume and at the same time undergo sol-gel transition catalyzed by HRP in the presence of $H_2O_2$ within the PC pores.[13] Successive dehydration of the silk gel-PC composite in increasing concentrations of ethanol followed by critical point drying of the sample[14] and removal of the PC template in dichloromethane (DCM) then generated porous silk pillars (FIG. 14*b*, iii). The second method to obtain silk pillars employs a completely different strategy, where the silk solution to be infiltrated comprises of silk fibers suspended in FA and $CaCl_2$.[15] The presence of sufficient amounts of $CaCl_2$ in the silk suspension was found to be the key for complete liquid filling of the PC pores and generation of silk pillar structures (FIG. 14*b*,iv-v), as the highly hygroscopic nature of $CaCl_2$ helps retain a large amount of bound water in the silk constructs (FIG. 19), which is the major contributing factor that maintains the pillar structure. What is more interesting about this silk-FA/$CaCk_2$ formulation is that it allows for generation of different nanostructures through different post-treatment of the silk/$CaCl_2$—PC composites. Besides the regular pillar structure obtained without any post-treatment (FIG. 14*b*, iv), mushroom-shaped pillars (FIG. 14*b*, v) were obtained by exposing the silk/$CaCl_2$—PC composites to vapors of a 80 v/v % EtOH/water solution for 3 hours followed by PC removal in DCM. Incubating the same silk/$CaCl_2$—PC composites in pure water vapors, however, converted the pillars to tubes (FIG. 20). To the best of our knowledge, this type of versatile control over the morphologies of nanostructures made of a single biopolymer has never been achieved before.

Figure 21:
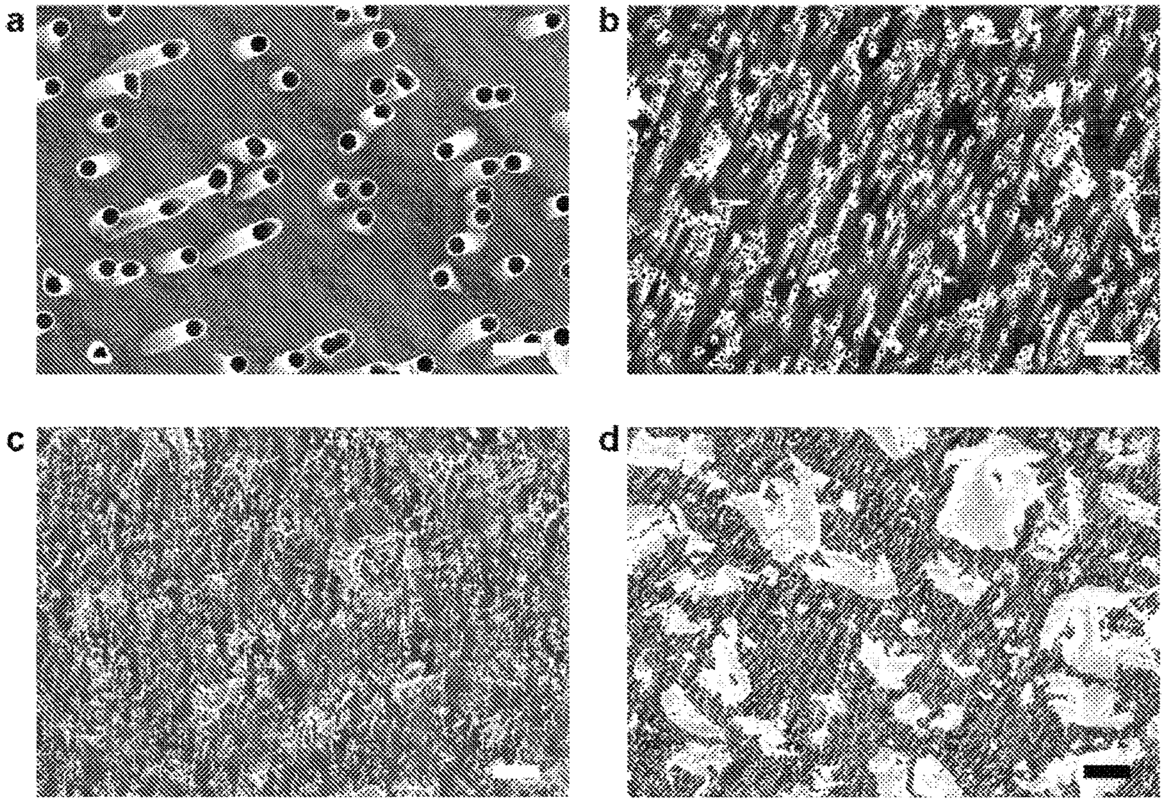
FIG. 21. Silk nanotube arrays of different tube diameter, aspect ratio and density. a, Tube diameter ϕ, aspect ratio η and density ρ being 2 μm, 5, and $2\times10^6$ pores/$cm^2$, respectively. b, ϕ, η, ρ=600 nm, 15, $3\times10^7$ pores/$cm^2$. c, ϕ, η, ρ=200 nm, 50, $3\times10^8$ pores/$cm^2$. d, ϕ, η, ρ=50 nm, 120, $6\times10^8$ pores/$cm^2$. Scale bars, 5 μm.

Another important merit of using this template-based approach is that the size of silk nanotube/pillar arrays fabricated can be extremely large, which in theory only depends on the size of the porous template available. Here, a self-standing silk nanotube array of size 20×20 $cm^2$ is demonstrated as an example (FIG. 14*c*), where the silk nanotubes are vertically well-aligned across the entire 20×20 $cm^2$ area. Large arrays of silk nanopillars can be obtained in the same way by infiltrating PC templates with the silk/$CaCl_2$—FA suspension followed by PC removal (FIG. 14*d*). By using PC templates with different pore sizes (from 2 μm down to 10 nm), silk nanotubes of corresponding diameters and aspect ratios were obtained (FIG. 14*e,f*; FIG. 21). Since the thicknesses of all PC templates used in this study are in the range of 6-10 μm while their pore sizes differ 3 orders of magnitude (i.e. from 2 μm down to 10 nm), the aspect ratios (defined by tube length divided by tube diameter) of silk nanotubes obtained range from 5 (in the case of being templated by PC membranes of 2 μm pores) to 600 (in the case of being templated by PC membranes of 10 nm pores). As the aspect ratio of silk nanotubes becomes larger (i.e. individual silk nanotubes become more slender), collapsing and/or aggregating of multiple nanotubes tend to happen more easily when the silk array is air dried after being immersed in DCM to remove the PC template. To better maintain the vertical alignment of silk nanotubes, special drying protocols such as critical point drying can be used which helps preserve the silk nanostructures from damage due to surface tension when changing from liquid to gas phases.[16] With critical point drying, vertically aligned silk nanotubes of diameter as small as 100 nm and aspect ratio as high as 60 can be obtained (FIG. 14*f*). Besides the morphology and dimensions of silk nanostructures, another parameter that we can easily regulate is the conformation of silk that the nanotubes/pillars are made of, from amorphous to different levels of crystallinity (i.e. β-sheet contents) (FIG. 14*g*). For example, annealing of the amorphous silk array (made from infiltrating a dried PC membrane with silk-water suspension) in water vapor or vapor from 80 v/v % EtOH/water can give rise to formation of silk I (type II β-turns) and silk II (antiparallel β-pleated sheets) conformations, respectively.[17] Other silk polymorphs can also be introduced through templated crystallization of silk on peptide seeds (e.g. a dodecapeptide (GAGSGA), and a coiled-coil peptide (referred to as HBSP) derived from honeybee silk AmelF3) that are known to interact with amorphous silk molecules and drive their folding and assembly into ordered conformations that resemble those of the peptide seeds. In this case, a PC membrane infiltrated with the peptide seeds solution is cast on a dried silk film, where the water in the peptide seeds solution first dissolves the silk film into silk molecules and then provides an aqueous environment for templated crystallization to occur within the PC pores.

Water Repellency and Anti-Fouling of Silk Nanotube Arrays

Figure 15:
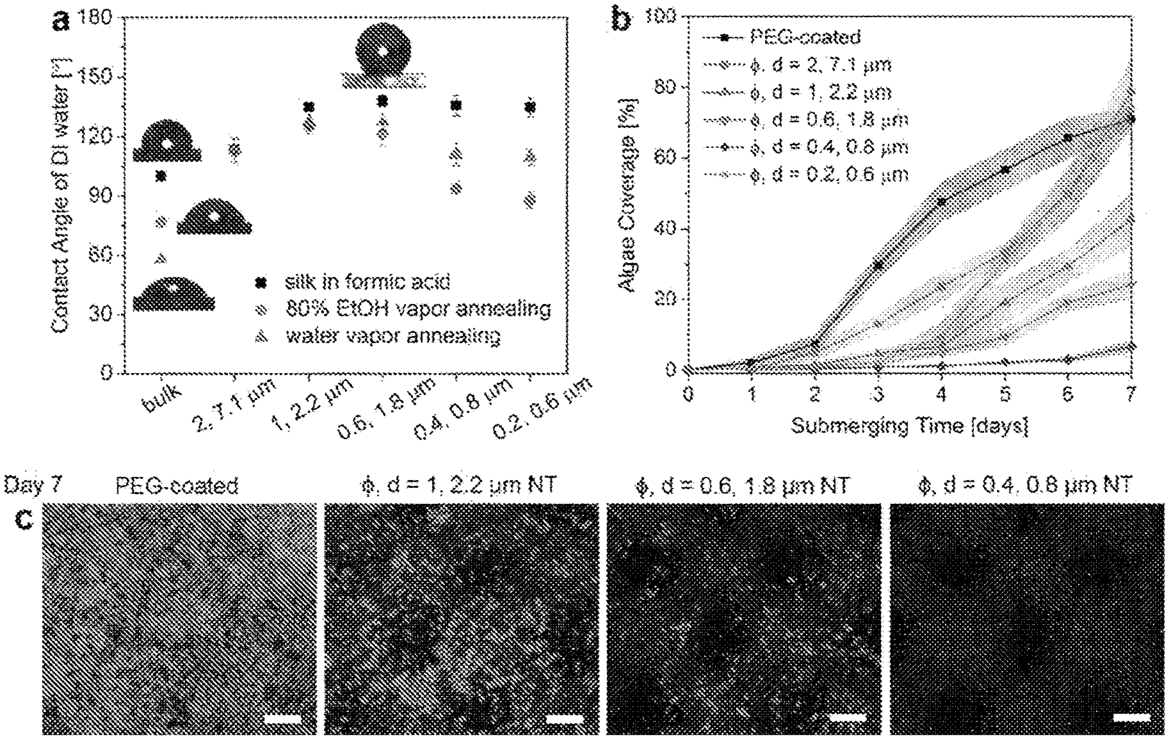
FIG. 15, Water repellency and anti-fouling of silk nanotube arrays. a, Static contact angles of water on bulk silk membranes and silk nanotube arrays of different tube diameter and inter-tube distance, made from three types of silk (i.e. silk dried from silk-FA suspension, 80% EtOH/water annealed silk, and water-annealed silk) that possess different intrinsic hydrophobicity. b, Area fraction of algae coverage on PEG-coated and silk nanotube-coated glass slides over time. c, Fluorescence microscopy images showing algae distribution and coverage on PEG-coated and silk nanotube-coated glass slides after being incubated in the algae culture for 7 days. Scale bars, 200 μm.

Inspired by the self-cleaning effects of lotus leaf, many studies have shown that micro-/nanostructured surfaces generally exhibit good water repellency, as their high surface roughness allows for air pockets entrapped between water droplets and the underlying substrate, which is well-captured by the Cassie-Baxter model.[19] Considering that the silk nanotube array obtained in this work possesses well-aligned sub-micron features and a large pore volume at the surface, it is expected that the silk nanotube array will be highly hydrophobic. To verify this assumption, contact angles (CA) of water droplets were measured on three types of nanotube arrays made of (1) silk dried from silk-FA suspension; (2) silk annealed in 80 v/v % EtOH/water vapor; and (3) silk annealed in water vapor (FIG. 15*a*). We first characterized the intrinsic hydrophobicity of bulk silk material without the effects of nanostructures, where the silk dried from a silk-FA suspension is slightly hydrophobic with a water CA of 100.0±0.4°, while both 80% EtOH-annealed and water-annealed silk are hydrophilic with a CA of 76.7±1.3° and 58.0±1.3°, respectively. This indicates that the three silk materials possess different surface energy, presumably due to the fact that the silk chains are folded and organized differently (i.e. having different polymorphs) in those three bulk films (FIG. 14*g*). Contact angles of silk nanotube arrays with different tube diameter and density (represented by distance between adjacent tubes) were then measured for all three silk materials, from which it is clear that by organizing silk into a forest of well-aligned nanotubes, the surface becomes close to superhydrophobic with CAs in the range of 134-138° in all cases of silk-FA nanotubes of tube diameter ≤1 μm. Even for the nanotube arrays made from 80% EtOH-annealed and water-annealed silk which are intrinsically hydrophilic, they show good hydrophobicity with CAs in the range of 121-127° in the case of ϕ, d=1, 2.2 and 0.6, 1.8 μm.

Figure 22:
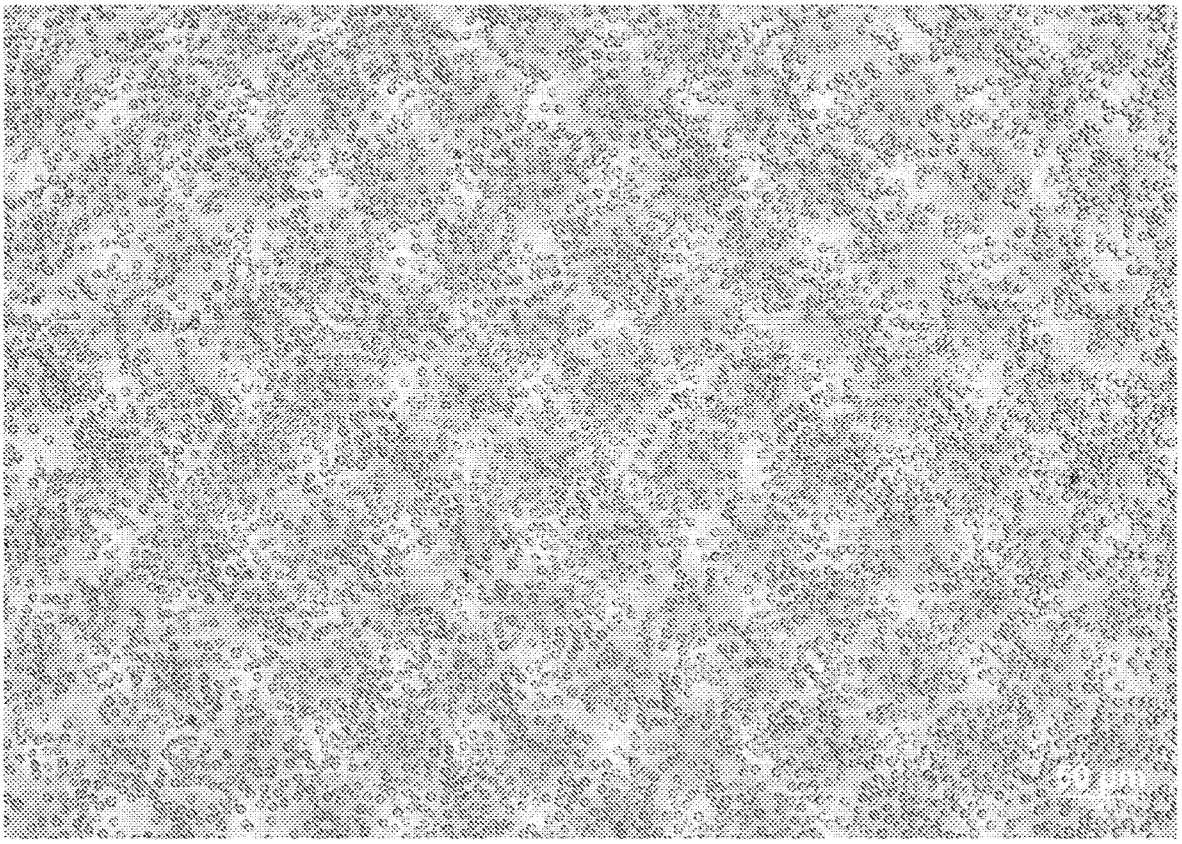
FIG. 22. Bright-field micrograph of *Porphyridium cruentum.*
Figure 23:
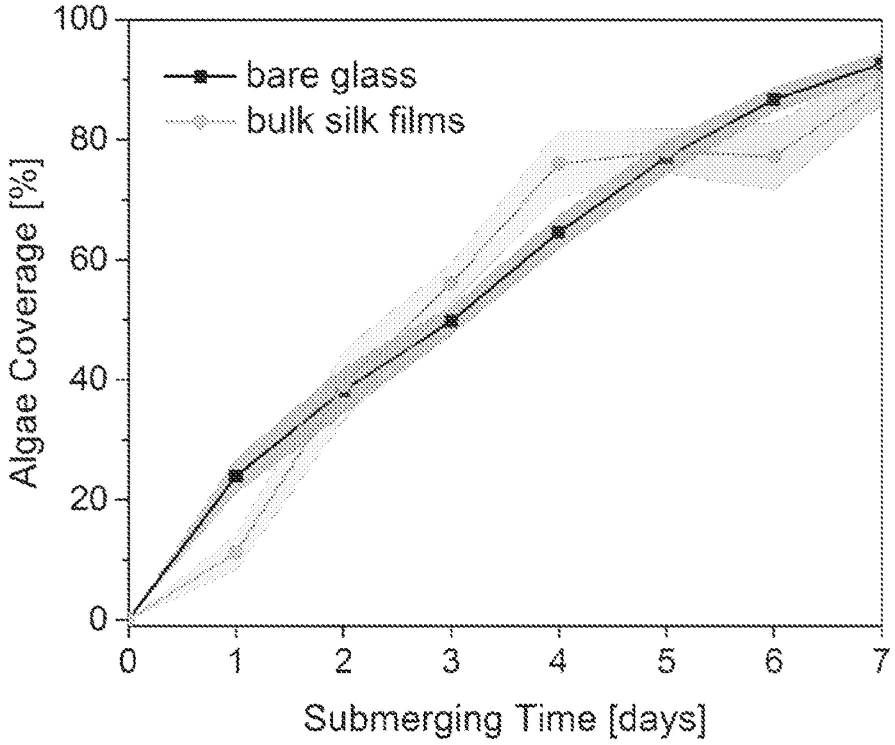
FIG. 23, Area fraction of algae coverage on bare glass and glass coated with bulk silk over time.

In light of the good hydrophobicity (i.e. water repellency) of nanotube arrays made from silk-FA suspension, we further hypothesized that they might function as an anti-fouling coating against microorganisms when submerged under water. We then tested the anti-fouling performance of our silk nanotube arrays against a species of marine algae named *Porphyridium cruentum* which has a spherical shape of around 4 μm in diameter (FIG. 22). The choice of this particular algae was based on its extremely high fouling capability on common substrates like glass within a few hours and the fact that it produces a red-fluorescent protein so that we can easily measure algae coverage over the silk nanotube array through fluorescence microscopy.[20] Here, our samples to be tested are silk nanotube-coated glass slides with different tube diameter and density; our positive control is PEG-coated glass slides bought from a commercial supplier (MicroSurfaces, Inc.), as PEG is a well-known coating material to inhibit non-specific binding from proteins and microorganisms; and our negative control is bare glass slides. We incubated the samples and controls in porphyridium culture for 7 days, and measured algae coverage every 24 hours from their fluorescence microscopy images (FIG. 15*b,c*). Compared to bare glass on which algae growth started off right away (FIG. 23), both PEG-coated and silk nanotube-coated surfaces showed a lagging period during which algae fouling remained at a very low level (FIG. 15*b*). The length of the lagging period, however, varies depending on the geometric parameters of the nanotube array. Regardless of their tube diameters and densities, all silk nanotube arrays showed less fouling than the positive control (FIG. 15*b*). Among the silk nanotube arrays tested, one of the worst performing is the array with 2 μm tube diameter and 7.1 μm inter-tube distance. This is not surprising, as the silk nanotubes are distributed too far apart with an average inter-tube distance larger than the size of individual alga, thereby the algae can easily occupy the inter-tube spaces once the liquid meniscus hanging over the nanotubes collapse. The other bad-performing nanotube array is the one with 200 nm tube diameter and 600 nm inter-tube distance. The main reason for this case we believe is that as the algae grow and attach to the surface, they exert forces to the silk nanotubes. For nanotubes with larger aspect ratios, they are more easily deformed by those disturbance forces applied by algae, which may cause the silk array to lose its original forest-like morphology, thereby leading to gradual loss of water-repellency and accelerated algae fouling at later time points. Based on these observations, we argue that there is a trade-off in nanotube design for anti-fouling performance, where one would want the nanotubes to be smaller in diameter and more densely packed, which imparts a higher hydrophobicity and longevity of water-repellency to the surface; but on the other hand, as the nanotubes become more slender, it is harder for the array to keep its nanoforest morphology against various disruptive forces that come from microorganism attachment. Agreeing with this rule of thumb, our results show that the silk nanotube array with a medium tube diameter and density (namely, 400 nm diameter and 800 nm inter-tube distance) possess the best anti-fouling performance with minimal algae fouling over the entire period of study (FIG. 15*b*). Fluorescence microscopy images of PEG-coated and silk nanotube-coated surfaces after being submerged in algae culture for 7 days are given in FIG. 15*c*, where the red areas correspond to areas covered by the algae.

Superoleophilicity and Oil Extraction from Oil-Water Emulsions

Figure 16:
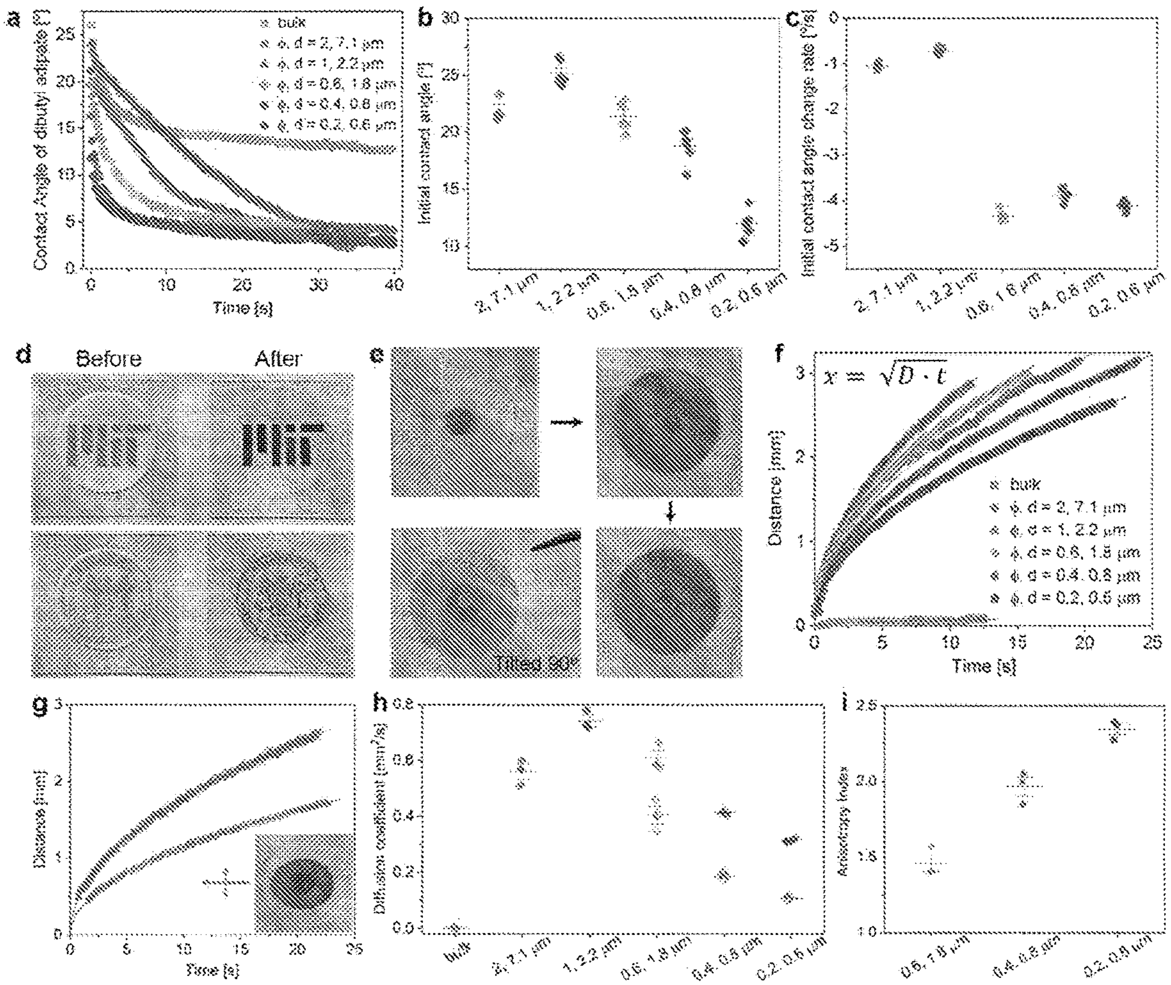
FIG. 16. Superoleophilicity and oil extraction from oil-water emulsions by silk nanotube arrays. a, Dynamic contact angles of dibutyl adipate (DA) on bulk silk membranes and silk nanotube arrays of different tube diameter and inter-tube distance. b, Initial contact angle of DA on silk nanotube arrays of different tube diameter and inter-tube distance at t=0. c, Initial contact angle change rates obtained by linear fitting of the initial data points in a. Sample number=5 for each type of silk nanotube array in b, c. d, Silk nanotube array of tube diameter 200 nm and inter-tube distance 600 nm before and after being infiltrated by an oil that has a refractive index of 1.55 which is very similar to the RI of silk. e, DA diffusion from the DA-water emulsion deposited on top of a silk nanotube array across the entire silk nanotube array. f, Plots of DA diffusion distance from the center of the DA-water emulsion as a function of time, and their fitting by equation $x=\sqrt{D\cdot t}$, where D is the diffusion coefficient. g, Anisotropic DA diffusion over a silk nanotube array of tube diameter 200 nm and inter-tube distance 600 nm. h, Diffusion coefficients extracted from the data fitting in f. i, Anisotropy index of oil diffusion (defined by $D_{max}/D_{min}$) calculated from the data in h. Sample number=3 for each type of silk nanotube array in h,i.

Besides being close to superhydrophobic, the silk nanotube arrays are also found to be superoleophilic. Here, we chose dibutyl adipate (DA) as a model oil to characterize the wettability of silk nanotube arrays by general oily compounds. The choice of DA was based on its wide usage in agriculture, food and cosmetics industry (e.g. as a solvent for pesticides/herbicides/fungicides). From contact angle measurements (FIG. 16*a*), we see that wetting of the silk nanotube arrays by DA start with a low contact angle (in the range of) 10-25°) which then drops quickly to 0 degree within 10-30 seconds. This is resulted from fast spreading and penetrating of DA across and into the silk nanotube arrays due to their porous nature. Depending on the geometric parameters of silk nanotube arrays (i.e. tube diameter and density), there shows some variances in their wettability profiles, which manifest mainly in the contact angle values at t=0 (FIG. 16*b*) and the contact angle change rates obtained by linear fitting of the initial data points (FIG. 16*c*). In particular, silk nanotube arrays with pore diameters <1 μm show higher oleophilicity than those with pore diameters ≥1 μm, as shown by their lower contact angles at t=0 and much faster contact angle decrease rates in the beginning (FIG. 16*b,c*). Complete oil penetration in the silk nanotube array was also verified by depositing a droplet of oil that has a refractive index (RI=1.55) very similar to that of silk,[22] which quickly spread all over the nanotube array and turned its original white appearance into transparent (FIG. 16*d*).

Figure 24:
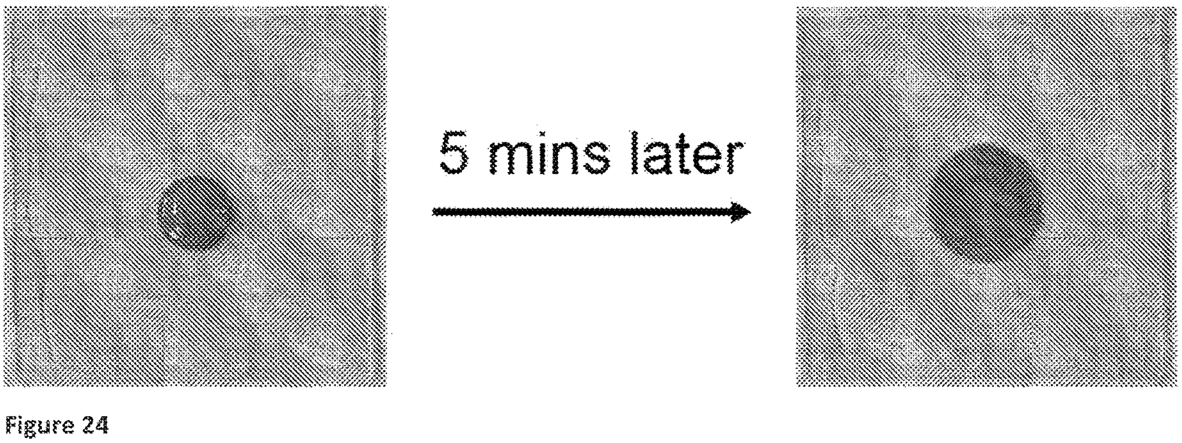
FIG. 24. Images of DA-water emulsions deposited on a bulk silk membrane, showing minimal DA diffusion/spreading over the bulk silk.
Figure 25:
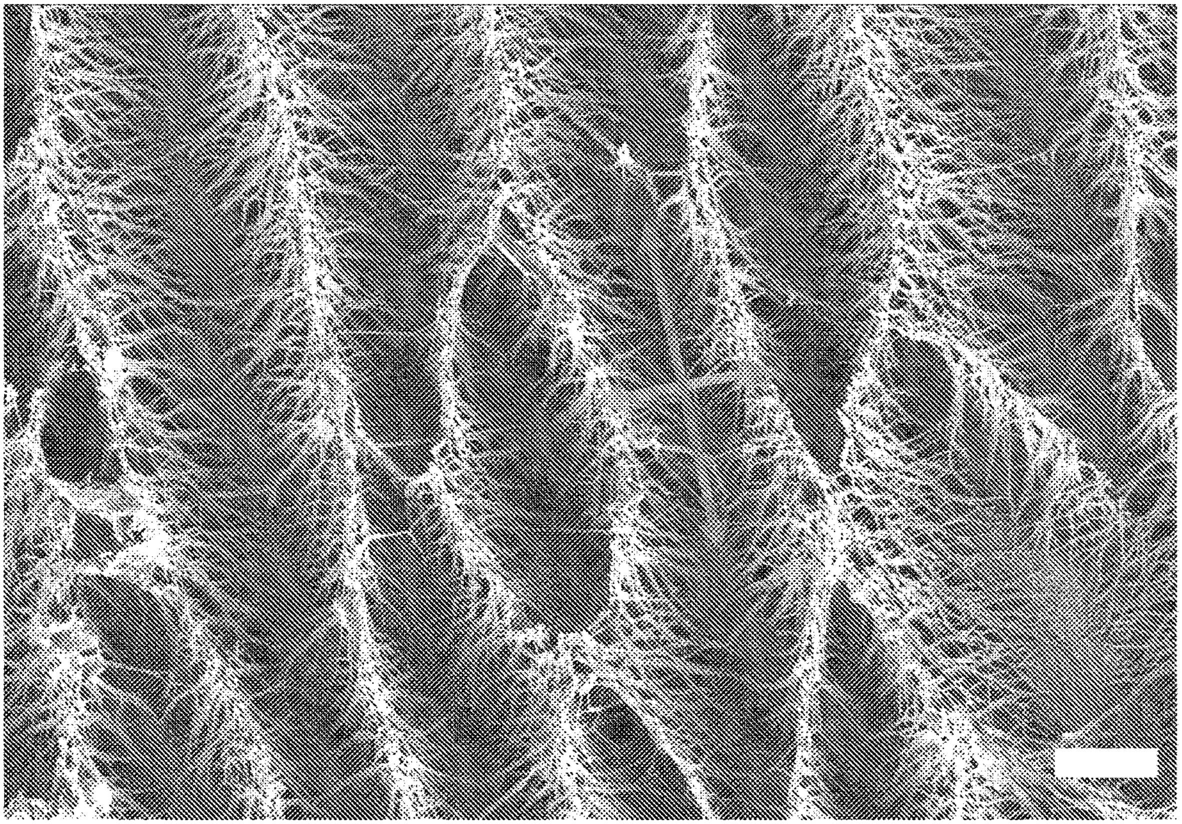
FIG. 25. SEM image of a silk nanotube array of configuration ϕ, d=0.2, 0.6 μm, showing aggregation of adjacent nanotubes at the top, resulting in formation of ridges of fused nanotubes which contributes to the anisotropic oil diffusion behavior observed in FIG. 16*g*.

Considering that the silk nanotube arrays are both highly hydrophobic and oleophilic, we then evaluated the capability of silk nanotube arrays to extract oil from oil-water mixtures. To this end, DA dyed with Sudan III was vigorously mixed with water to form a homogenous emulsion by using tip sonication. Upon adding an emulsion droplet on a silk nanotube array, the oil component spread quickly over the entire nanostructured silk array, leaving only a clear water droplet on top of the array in the end (FIG. 16*e*). Importantly, oil spreading was confined only within the nanotubular region and did not extend outside of the array, indicating that the nanotubular structure of the silk array plays a critical role in superoleophilicity and oil extraction. Indeed, when the same DA-water emulsion was deposited on bulk silk films, no extraction of DA in the bulk film was observed (FIG. 24). The silk nanotube array was also able to hold the oil in its interior without any oil dripping after tilting the substrate by 90 degree (FIG. 16*e*, iv). We then quantified the speeds of oil extraction by silk nanotube arrays with different geometric parameters, through measuring the oil spreading distances over time. Interestingly, the data was found to follow the random walk model characterized by equation $x=\sqrt{D\cdot t}$ (where D represents the diffusion coefficient).[23] As shown in FIG. 16*f*, the oil component from the oil-water emulsion diffuses within the silk nanotube arrays at different rates, depending on their tube diameters and densities. Besides, for nanotube arrays with tube diameters smaller than 1 μm, oil diffusion proceeds at different rates along different directions (FIG. 16*g*), which is believed to be resulted from the anisotropy in the microscopic morphologies of nanotube arrays. As silk nanotubes become more slender and more densely packed, they tend to aggregate at their open ends forming ridges of fused nanotubes (FIG. 25), in contrast to the well-isolated nanotubes templated from ϕ, d=2, 7.1 μm and 1, 2.2 μm PC membranes (FIG. 14*c*; FIG. 21*a*). Oil diffusion along the ridge direction is foreseeably faster than that perpendicular to the ridge direction (FIG. 25), which corresponds to the anisotropic diffusion behavior shown in FIG. 16*g*. Diffusion coefficients for each nanotube configuration were obtained by fitting the data in FIG. 16*f,g* and plotted in FIG. 16*h* for easier comparison. An anisotropy index defined by $D_{max}/D_{min}$ was also calculated for nanotube arrays that show anisotropic oil diffusion (FIG. 16*i*), from which we can see that arrays with more slender and more densely packed nanotubes exhibit a larger anisotropy index, which is not surprising based on our understanding of the origin of anisotropic diffusion.

Gas Barrier Property of Nanostructured Silk Membranes

Figure 17:
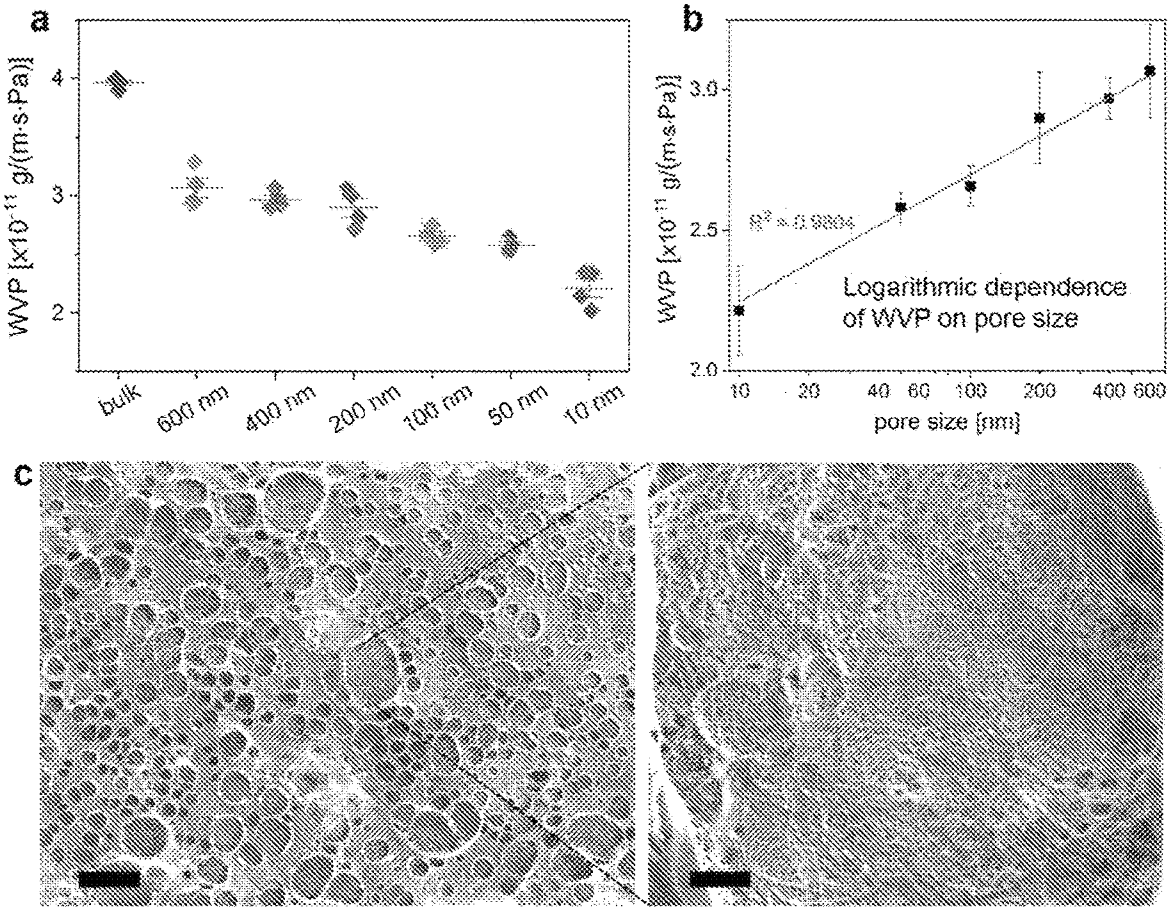
FIG. 17. Water vapor permeability (WVP) of nanostructured silk membranes. a, WVP values of bulk silk membranes and nanostructured silk membranes fabricated from PC templates of different pore sizes. Sample number=4 for each type of silk membrane. b, The same WVP values from (a) plotted against the nominal pore size of silk nanotube membranes on a log scale, showing a linear decrease of WVP with respect to pore size. c, SEM images showing the surface morphology of nanostructured silk membranes templated from PC membranes of 10 nm pores, which present a hierarchical pore structure with micron-scale larger pores and entangled silk nanowires inside the micrometer pores. Scale bars, 10 μm (left) and 1 μm (right).

Apart from the studies on how silk nanotube arrays behave when brought into contact with liquids, we were also interested to know if the silk nanotube arrays fabricated as free-standing membranes interact with gases differently. This question was also motivated by potentially using these nanostructured silk membranes as a packaging material, as previous studies have shown that food coatings made of silk fibroin present good gas barrier properties.[24] To this end, we measured the water vapor permeability (WVP) of silk membranes fabricated from PC templates of different pore sizes and densities, by following a ASTM protocol (E96/E96M) with some modifications (see Supporting Information for more details).[24,25] Interestingly, we found that nanostructured silk membranes show lower WVP compared to bulk silk membranes of the same thickness, and the WVP decreases as the nominal pore sizes of the nanostructured silk membranes decrease (FIG. 17*a*). Moreover, when plotting the nominal pore size of the silk nanotube membranes on a log scale, the decrease in WVP with respect to pore size becomes roughly a linear trend (FIG. 17*b*). In other words, there seems to be a logarithmic dependence of WVP of nanostructured silk membranes on their nominal pore size. It is also important to note that the silk membranes fabricated from PC templates of 10 nm pores show a very complicated morphology with hierarchical pore structures, i.e. having micron-scale larger pores and entangled silk nanowires inside the micrometer pores (FIG. 17*c*), which is very different from the nanostructured silk membranes fabricated from PC templates of other pore sizes (FIG. 14*e,f*, FIG. 21*b-d*). This is likely because the thickness of the precursor liquid film (which is reported to be in the range of 10-30 nm for many polymer solutions)[7] is larger than the PC pore size, thereby wetting of the 10 nm PC pores by the same silk solution occur in a different way. It is hypothesized that there might be some interaction between silk molecules and water vapor that is holding the water vapor from passing through the membrane. As nanostructured silk membranes have larger specific surface areas, they are able to retard water vapor permeation to a larger extent. More work particularly characterization on the real pore geometry (e.g. pore size distribution, pore volume and specific surface area) of the nanostructured silk membranes fabricated for WVP measurements are needed to verify this hypothesis and to decipher the reason for the WVP difference between nanostructured and bulk silk membranes.

Conclusion

To summarize, we have reported a simple and robust approach for fabricating large arrays of well-aligned 1D nanostructures made of silk proteins, by retrofitting a well-studied template wetting phenomenon. Through the use of commercially available and low-cost PC membranes with a diverse range of pore sizes and densities as sacrificial templates and by regulating the biopolymer formulation thereby changing its surface energy, wetting of the PC templates occur via either formation of a mesoscopic liquid film or complete filling of the pore interior, generating large arrays (up to 20×20 cm) of well-aligned silk nanotubes or nanopillars, respectively. Such silk nanotube/pillar arrays can either be grown directly on an external substrate as a coating material or be fabricated as a free-standing film, which are found to be both highly hydrophobic and superoleophilic. Benefiting from its high water-repellency, substrates coated with silk nanotube arrays present significantly reduced fouling by marine algae, compared to PEG-coated surfaces. Furthermore, the silk nanotube arrays can rapidly extract oil from oil-water emulsions due to its simultaneous hydrophobicity and superoleophilicity, which offers an effective solution in oil spill response. Lastly, effects of nanostructures on the gas barrier property of silk membranes are investigated, using water vapor as a model gas. The nanotubular-structured silk membranes are found to possess lower water vapor permeability (WVP) than bulk membranes, which may serve as a better material for food packaging. Together, by integrating the template wetting approach with the versatility of silk proteins, precise control over the size, density, aspect ratio, morphology and polymorphs of silk nanostructures can be achieved, which then allows for programmably regulating the functions and macroscopic properties of the end materials. We believe that the biodegradable, non-toxic and edible nature of silk proteins in combination with the capability to organize silk proteins into centimeter-scale arrays with well-aligned nanostructures will open up exciting opportunities for a broad range of applications, particularly in the AgroFood and environmental domain.

Experimental Section

Materials

All PVP-coated polycarbonate (PC) membranes used in this study were purchased from Structure Probe, Inc. (USA), except the PVP-coated PC sheets used to fabricate the 20×20 $cm^2$ silk arrays which were purchased from Sterlitech (USA), PEG-coated glass slides were purchased from MicroSurfaces, Inc. (USA). Liquid cultures of *Porphyridium cruentum* and the corresponding media kit (salts+nutrients) for algae culture were purchased from Algae Research and Supply (USA). Dibutyl adipate (99.0+%) was purchased from TCI America (USA). The refractive index oil (RI=1.550) was purchased from ENVIROPORE (USA). All other chemicals were purchased from Sigma Aldrich (USA).

Silk fibroin regeneration: Silk fibroin was extracted from *Bombyx mori* cocoons following established protocols.[26] In brief, chopped silk cocoons were degummed in a boiling 0.02 M sodium carbonate solution for 30 minutes to remove the sericin. The obtained silk fibers were then washed with Milli-Q™ water for several times followed by overnight drying. The dried silk fibers were dissolved in 9.3 M lithium bromide at 60° C. for 4 hours followed by dialysis against Milli-Q™ water for 2 days with constant changing of water. The resulting silk fibroin solution was then purified by two centrifugation cycles at 20,000×g for 30 minutes each, yielding a final silk fibroin solution of ~7 wt %. The regenerated silk fibroin solution was then stored at 4° C. until use.

Fabrication Methods

Fabrication of silk nanotube arrays: To fabricate nanotube arrays, two silk solutions of concentration 2-10 wt % were prepared: (1) silk-water suspension obtained right after silk fibroin regeneration from *Bombyx mori* cocoons; (2) silk foams lyophilized from the silk-water suspension and re-suspended in formic acid (FA) to form a silk-FA suspension. Wetting of the porous PC membranes by silk solution was simply achieved by putting a PC membrane on top of a silk solution reservoir. To coat glass slides with silk nanotube arrays, a thin layer of silk solution was first drop cast on an oxygen-plasma treated glass slide, followed by adding a PC membrane on top of the silk solution. The silk solution was then air dried with the PC membrane in place to template the top layer of silk into nanotubular structures. Finally, the whole glass slide was immersed in DCM for 1 min to dissolve away the PC membrane and then taken out and air dried, so that only the silk nanotube array was left on the glass slide. To fabricate a free-standing silk nanotube array with bulk silk as the base, the same process was repeated except that PDMS or polystyrene petri dish was used as the substrate for drop casting silk, so that the dried silk array can be easily peeled off from the substrate and then immersed in DCM to remove the PC followed by air dry to obtain a free-standing silk nanotube array.

For the amorphous silk nanotube array obtained from silk-water suspension, annealing of the dried silk-PC composites was performed by incubating them in either pure water vapor or vapor from 80 v/v % EtOH/water for 24 hours to induce conformational change of silk from amorphous to silk I or silk II structures, respectively, both of which render the silk nanotube array water-insoluble. The silk-PC composites were then immersed in DCM to remove the PC template, leaving only the annealed silk nanotube array in the end.

Fabrication of silk nanopillar arrays: To fabricate nanopillar arrays, two silk-based solutions were prepared: (1) A 2 wt % silk-water suspension was mixed with HRP (final concentration: 10 U/ml), followed by addition of $H_2O_2$ (final concentration: 1.65 mM) to initiate gelation. Immediately after mixing the three components, a PC membrane was placed on top of the solution, which was then incubated in a humid chamber for 2 hours to allow for complete gelation of silk in the PC nanopores. The silk-PC composite was then consecutively immersed in a series of ethanol/water solution with increasing ethanol concentration (i.e. 50%, 75%, 90% and 98% EtOH) for 30 minutes each, and finally immersed in pure ethanol overnight for complete dehydration before critical point drying. (2) Degummed silk fibers were dissolved in FA with 2 wt % $CaCl_2$ to a final concentration of 6 wt % silk for 12 hours under stirring. The clear silk-FA/$CaCl_2$ suspension was then aged for two weeks before use. Wetting of the porous PC membranes by silk-FA/CaCl suspension and the following air dry process were the same as described before. Annealing of the dried silk pillar-PC composites in pure water vapor for 3 hours was performed to induce pillar to tube transformation. Annealing of the dried silk pillar-PC composites in vapor from 80 v/v % EtOH/water for 3 hours was performed to induce formation of the mushroom-like pillar structure. Finally, all silk-PC composites were immersed in DCM to remove the PC template, leaving only the silk nanopillar array in the end.

Critical Point Drying (CPD): Most of the samples prepared in this study were air dried. For the samples that require CPD, they were first dehydrated by soaking them in a series of ethanol/water solution with increasing ethanol concentration as described before, and then dried in a critical point dryer (Tousimis Autosamdri-815B) following the manufacturer's recommended procedures.

Fabrication of $CaCO_3$-silk nanotube composite: $CaCO_3$ crystallization in silk nanotubes was performed following a published protocol with some modifications.[27] Calcium chloride ($CaCl_2$)) was first added to a 6 wt % silk-water suspension to a final concentration of 30 mM. A thin layer of the silk-CaCl solution was then drop cast on a coverslip, followed by placing a PC membrane on top of the silk-$CaCl_2$) solution to initiate wetting of the PC pores. Without letting the silk-$CaCl_2$ solution dry out, the coverslip was immediately placed into a weigh boat sealed by a parafilm. The weigh boat was then transferred to a closed desiccator, where another weigh boat containing 5 g of solid ammonium carbonate sealed by a parafilm was placed at the bottom. To allow for slow diffusion of the gaseous decomposition products (i.e. carbon dioxide and ammonia) of ammonium carbonate into the silk-CaCl solution, the parafilms covering both weigh boats were punched with a 20-gauge needle to generate 4 holes. $CaCO_3$ crystallization was then initiated under the action of carbon dioxide and ammonia and allowed to proceed for 48 hours in the closed desiccator, before taking the samples out and letting them dry out. The dried samples were then immersed in DCM for 1 minute to dissolve away the PC templates followed by air dry, leaving only the $CaCO_3$-silk nanotube array on the coverslip.

Preparation of Dibutyl Adipate (DA)-water emulsion: DA was first dyed with Sudan III (a water-insoluble dye) for better visual differentiation from water during oil-water separation. 1 mL of dyed DA was then added to 1 mL water and vigorously mixed through tip-sonication (Branson SFX 550 Sonifier). The 2 mL DA-water mixture was sonicated in an ice bath for 3 minutes with an amplitude of 35% (165 W output power) and pulse durations of 5 s on-time and 5 s off-time to generate a homogenized emulsion. Following sonication, the DA-water emulsion was used immediately for oil-water separation tests.

Characterization

Scanning Electron Microscopy (SEM): The morphology and microscopic view of various silk nanotube and nanopillar arrays as prepared were imaged with a Zeiss Merlin High-resolution SEM, under an acceleration voltage of 1 kV and a probe current of 80 pA.

Wide-angle X-ray Scattering (WAXS): WAXS measurements of free-standing silk nanotube/pillar membranes were performed on a SAXSLAB™ instrument in transmission mode with a Dectris Pilatus3R™ 300 K detector set at a distance of 109.1 mm from the sample and a Rigaku™ 002 microfocus X-ray source producing Cu Kat X-rays of wavelength 1.5409 Å. Each spectrum was collected for 5 minutes.

Contact Angle Measurements: Contact angle measurements were performed on a Ramé-Hart goniometer (Model 500-F1). For measurements with water, a water droplet of 3 μL was deposited on each sample through a microliter syringe (Hamilton) followed by immediate image capture, from which the static contact angle of water was measured by the DROPimage™ software (Ramé-Hart). For measurements with DA, a series of images were captured by setting up a method through the DROPimage™ software that specifies the total number of frames (set to be 501) and the time interval between adjacent frames (set to be 0.2 second). As the series of images were being captured, dynamic contact angles were measured simultaneously by the DROPimage™ software, generating a LOG file in the end that stores the contact angle measurements for all frames.

Algae Fouling Experiments: Liquid cultures of *Porphyridium cruentum* purchased from Algae Research and Supply were re-cultured in 750 mL cell culture flasks at room temperature (23° C.) with a lighting condition of 12-hours on, following the supplier's recommended algae culture protocol. Half of the total culture volume was replaced with fresh culture media every 3 days. 100 mL of freshly-cultured algae were then transferred to a petri dish (100×25 mm), followed by submerging the samples in the algae culture. The algae culture in petri dishes were also grown under the same condition, and half of the total culture volume (i.e. 50 mL) was replaced with fresh culture media every 3 days. The hydrostatic pressure on the testing samples were kept at ≈125 Pa.

Fluorescence Microscopy: Fluorescence microscopy images of algae distribution were captured by a Nikon TE2000-E inverted microscope equipped with a Texas Red™ filter cube set. All samples were gently flushed with 0.9 wt % NaCl solution to wash away loosely-bound algae and then sealed in between a glass slide and a coverslip with 0.9 wt % NaCl solution to ensure samples being hydrated and algae being alive during imaging.

Algae Coverage Quantification: Area fractions of algae coverage were quantified from the fluorescence microscopy images through ImageJ analysis.[28] A fluorescence micrograph (RGB color) was first converted to a 16-bit grayscale image, followed by setting an appropriate threshold to mask out the algae particles within the image. Fraction of the unmasked area (denoted as $A_{background}$) was measured by ImageJ, and the area fraction of algae coverage then equals $1-A_{background}$.

Water Vapor Permeability (WVP) measurements: WVP of silk membranes (both nanostructured and bulk) were measured following the test cup method described in ASTM E96/E96M with some modifications.[25,29] Briefly, a circular silk membrane (Φ=12 mm) was sandwiched between a glass vial (VWR, Catalog Number: 66011-041) filled up with anhydrous $CaCl_2$ pellets (Fisher Scientific) and a lid with a circular opening (Φ=7 mm, McMaster-Carr, Part Number: 1576N12). The silicone rubber septa that comes with the lid was punched to generate a Φ=7 mm hole in the middle and placed in between the silk membrane and the glass vial to make a better seal. After assembling the four parts (i.e. lid, silk membrane, septa, and glass via filled with desiccant, from top to bottom order) together by screwing down the lid to hand tight, several layers of parafilm were wrapped around the lid and glass vial interface to further strengthen the seal. The assembled glass vials were then placed in an airtight container that was equilibrated at 75% RH and room temperature (23° C.) by placing a bowl of saturated NaCl solution in the container. A hygrometer was also placed in the container to verify that the targeted humidity level (i.e. 75% RH) had been reached throughout the measurement period. The glass vials were weighed every 24 hours for a total period of 7 days, and the water vapor transmission rate (WVTR) was calculated by performing a linear fitting of the glass vial weight gain with respect to time. WVP for each sample was then calculated as follows:

$$WVP = \frac{WVTR \cdot d}{A \cdot S \cdot (RH_2 - RH_1)}$$

where d is the thickness of the silk membrane, A is the permeation area (i.e. the area of the circular opening in the lid and septa), Sis the saturation vapor pressure of water at 23° C., $RH_1$ and $RH_2$ are the relative humidity inside the glass vials and in the container, respectively (i.e., $RH_1$=0% and $RH_2$=75%).

Thermogravimetric analysis (TGA): Quantification of residual water contents in silk arrays dried from different formulations were performed on a TA instruments Discovery TGA. For each measurement, ~4 mg of samples were first equilibrated at 40° C. for 1 minute and then heated up to 600° C. with a 10° C./min ramp rate.

It should be understood that the subject matter defined in the appended claims is not necessarily limited to the specific implementations described above. The specific implementations described above are disclosed as examples only.

REFERENCES

Reznikov, N.; Shahar, R.; Weiner, S. Bone Hierarchical Structure in Three Dimensions. In *Acta Biomaterialia;* 2014. https://doi.org/10.1016/j.actbio.2014.05.024.

Tritschler, U.; Cölfen, H. Self-Assembled Hierarchically Structured Organic-Inorganic Composite Systems. *Bioinspir. Biomim.* 2016, 11 (3), 35002.

Boskey, A. L. Mineralization of Bones and Teeth. Elements 2007. https://doi.org/10.2113/GSELEMENTS.3.6.385.

Shenhar, R.; Norsten, T. B.; Rotello, V. M. Polymer-Mediated Nanoparticle Assembly: Structural Control and Applications. *Advanced Materials.* 2005. https://doi.org/10.1002/adma.200401291.

Cigler, P.; Lytton-Jean, A. K. R.; Anderson, D. G.; Finn, M. G.; Park, S. Y. DNA-Controlled Assembly of a NaTl Lattice Structure from Gold Nanoparticles and Protein Nanoparticles. *Nat. Mater.* 2010. https://doi.org/10.1038/nmat2877.

Macfarlane, R. J.; Lee, B.; Jones, M. R.; Harris, N.; Schatz, G. C.; Mirkin, C. A. Nanoparticle Superlattice Engineering with DNA. *Science* (80-.). 2011. https://doi.org/10.1126/science.1210493.

Pyles, H.; Zhang, S.; De Yoreo, J. J.; Baker, D. Controlling Protein Assembly on Inorganic Crystals through Designed Protein Interfaces. *Nature* 2019. https://doi.org/10.1038/s41586-019-1361-6.

Webb, P.; Benton, T. G.; Beddington, J.; Flynn, D.; Kelly, N. M.; Thomas, S. M. The Urgency of Food System Transformation Is Now Irrefutable. *Nat. Food* 2020, 1 (10), 584-585.

Zvinavashe, A. T.; Laurent, J.; Mhada, M.; Sun, H.; Fouda, H. M. E.; Kim, D.; Mouhib, S.; Kouisni, L.; Marelli, B. Programmable Design of Seed Coating Function Induces Water-Stress Tolerance in Semi-Arid Regions. *Nat. Food* 2021. https://doi.org/10.1038/s43016-021-00315-8.

Nano for Agriculture, Not the Opposite. *Nat. Nanotechnol.* 2020, 15 (9), 725. https://doi.org/10.1038/s41565-020-0766-6.

Zhao, L.; Lu, L.; Wang, A.; Zhang, H.; Huang, M.; Wa, H.; Xing, B.; Wang, Z.; Ji, R. Nano-Biotechnology in Agriculture: Use of Nanomaterials to Promote Plant Growth and Stress Tolerance. *J. Agric. Food Chem.* 2020, 68 (7), 1935-1947. https://doi.org/10.1021/acs.jafc.9b06615.

Crippa, M.; Solazzo, E.; Guizzardi, D.; Monforti-Ferrario, F.; Tubiello, F. N.; Leip, A. Food Systems Are Responsible for a Third of Global Anthropogenic GHG Emissions. *Nat. Food* 2021, 2 (3), 198-209.

Flörke, M.; Schneider, C.; McDonald, R. I. Water Competition between Cities and Agriculture Driven by Climate Change and Urban Growth. *Nat. Sustain.* 2018, 1 (1), 51-58. https://doi.org/10.1038/s41893-017-0006-8.

Law, K. L.; Narayan, R. Reducing Environmental Plastic Pollution by Designing Polymer Materials for Managed End-of-Life. *Nat. Rev. Mater.* 2021, 1-13.

Zheng, J.; Suh, S. Strategies to Reduce the Global Carbon Footprint of Plastics. *Nat. Clim. Chang.* 2019, 9 (5), 374-378.

Babity, S.; Laszlo, E.; Brambilla, D. Polymer-Based Microneedles for Decentralized Diagnostics and Monitoring: Concepts, Potentials, and Challenges. *Chem. Mater.* 2021.

Sivasankarapillai, V. S.; Das, S. S.; Sabir, F.; Sundaramahalingam, M. A.; Colmenares, J. C.; Prasannakumar, S.; Rajan, M.; Rahdar, A.; Kyzas, G. Z. Progress in Natural Polymer Engineered Biomaterials for Transdermal Drug Delivery Systems. *Mater. Today Chem.* 2021, 19, 100382. https://doi.org/https://doi.org/10.1016/j.mtchem.2020.100382.

Samant, P. P.; Niedzwiecki, M. M.; Raviele, N.; Tran, V.; Mena-Lapaix, J.; Walker, D. I.; Felner, E. I.; Jones, D. P.; Miller, G. W.; Prausnitz, M. R. Sampling Interstitial Fluid from Human Skin Using a Microneedle Patch. Sci. Transl. Med. 2020, 12 (571).

Fiorello, I.; Tricinci, O.; Naselli, G. A.; Mondini, A.; Filippeschi, C.; Tramacere, F.; Mishra, A. K.; Mazzolai, B. Climbing Plant-Inspired Micropatterned Devices for Reversible Attachment. Adv. Funct. Mater. 2020, 30 (38), 2003380. https://doi.org/https://doi.org/10.1002/adfm.202003380

Kundu, A.; Nogueira Campos, M. G.; Santra, S.; Rajaraman, S. Precision Vascular Delivery of Agrochemicals with Micromilled Microncedles (MMMNs). *Sci. Rep.* 2019, 9 (1), 14008. https://doi.org/10.1038/s41598-019-50386-8.

Kim, D.; Cao, Y.; Mariappan, D.; Bono Jr, M. S.; Hart, A. J.; Marelli, B. A Microneedle Technology for Sampling and Sensing Bacteria in the Food Supply Chain. *Adv. Funct. Mater.* 2020, 2005370.

Cao, Y.; Lim, E.; Xu, M.; Weng, J.-K.; Marelli, B. Precision Delivery of Multiscale Payloads to Tissue-Specific Targets in Plants. *Adv. Sci.* 2020, n/a (n/a), 1903551. https://doi.org/10.1002/advs.201903551.

Kusama, S.; Sato, K.; Matsui, Y.; Kimura, N.; Abc, H.; Yoshida, S.; Nishizawa, M. Transdermal Electroosmotic Flow Generated by a Porous Microneedle Array Patch. *Nat. Commun.* 2021, 12 (1), 658. https://doi.org/10.1038/s41467-021-20948-4.

Cheung, K.; Das, D. B. Microneedles for Drug Delivery: Trends and Progress. *Drug Deliv.* 2016, 23 (7), 2338-2354.

Rockwood, D. N.; Preda, R. C.; Yücel, T.; Wang, X.; Lovett, M. L.; Kaplan, D. L. Materials Fabrication from *Bombyx Mori* Silk Fibroin. *Nat. Protoc.* 2011. https://doi.org/10.1038/nprot.2011.379.

Haynes, W. M. *CRC Handbook of Chemistry and Physics; CRC press,* 2014.

Jun, Y.-S.; Kim, D.; Neil, C. Heterogeneous Nucleation and Growth of Nanoparticles at Environmental Interfaces. *Acc. Chem. Res.* 2016, 49 (9), 1681-1690. https://doi.org/10.1021/acs.accounts.6b00208.

(Li, Y.; Diddens, C.; Segers, T.; Wijshoff, H.; Versluis, M.; Lohse, D. Evaporating Droplets on Oil-Wetted Surfaces: Suppression of the Coffee-Stain Effect. *Proc. Natl. Acad. Sci.* 2020, 117 (29), 16756-16763.

Deegan, R. D.; Bakajin, O.; Dupont, T. F.; Huber, G.; Nagel, S. R.; Witten, T. A. Capillary Flow as the Cause of Ring Stains from Dried Liquid Drops. *Nature* 1997, 389 (6653), 827-829.

Marelli, B.; Ghezzi, C. E.; Alessandrino, A.; Barralet, J. E.; Freddi, G.; Nazhat, S. N. Silk Fibroin Derived Polypeptide-Induced Biomineralization of Collagen. *Biomaterials* 2012. https://doi.org/10.1016/j.biomaterials.2011.09.039.

De Yoreo, J. J. Principles of Crystal Nucleation and Growth. *Rev. Mineral. Geochemistry* 2003. https://doi.org/10.2113/0540057.

Jin, H. J.; Kaplan, D. L. Mechanism of Silk Processing in Insects and Spiders. *Nature* 2003. https://doi.org/10.1038/nature01809.

Hu, X.; Kaplan, D.; Cebe, P. Determining Beta-Sheet Crystallinity in Fibrous Proteins by Thermal Analysis and Infrared Spectroscopy. *Macromolecules* 2006. https://doi.org/10.1021/ma0610109.

Samant, P. P.; Prausnitz, M. R. Mechanisms of Sampling Interstitial Fluid from Skin Using a Microneedle Patch. *Proc. Natl. Acad. Sci.* 2018, 115 (18), 4583-4588.

Koeppel, A.; Laity, P. R.; Holland, C. The Influence of Metal Ions on Native Silk Rheology. *Acta Biomater.* 2020, 117, 204-212.

Frost, R. L.; Williams, P. A.; Martens, W.; Leverett, P.; Kloprogge, J. T. Raman Spectroscopy of Basic Copper (II) and Some Complex Copper (II) Sulfate Minerals: Implications for Hydrogen Bonding. *Am. Mineral.* 2004, 89 (7), 1130-1137.

Monti, P.; Taddei, P.; Freddi, G.; Asakura, T.; Tsukada, M. Raman Spectroscopic Characterization of *Bombyx Mori* Silk Fibroin: Raman Spectrum of Silk I. *J. Raman Spectrosc.* 2001, 32 (2), 103-107.

Epstein, E. Bloom. A. 2005. Mineral Nutrition of Plants: Principles and Perspectives. Sinauer Associates, Sunderland, Massachusetts.

Jensen, R. R.; Brake, S. S.; Wolf, S. F.; Bekker, M. F.; Hardin, P. J.; Jackson, M. W. Chemical Element Concentrations in Black Locust (*Robinia Pseudoacacia* L.) and Green Ash (*Fraxinus Pennsylvanica* Marsh.) Leaves at the Reclaimed Green Valley Coal Mine, Indiana, USA. *Environ. Earth Sci.* 2010, 60 (7), 1391-1405.

Lamichhanc, J. R.; Osdaghi, E.; Behlau, F.; Köhl, J.; Jones, J. B.; Aubertot, J.-N. Thirteen Decades of Antimicrobial Copper Compounds Applied in Agriculture. A Review. *Agron. Sustain. Dev.* 2018, 38 (3), 28. https://doi.org/10.1007/s13593-018-0503-9.

Health, N. I. of. Copper, Fact Sheet for Health Professionals https://ods.od.nih.gov/factsheets/Copper-HealthProfessional/.

Zhou, P.; Xie, X.; Knight, D. P.; Zong, X.-H.; Deng, F.; Yao, W.-H. Effects of PH and Calcium Ions on the Conformational Transitions in Silk Fibroin Using 2D Raman Correlation Spectroscopy and 13C Solid-State NMR. *Biochemistry* 2004, 43 (35), 11302-11311. https://doi.org/10.1021/bi049344i.

Gao, P.; Huang, J.; Wang, Y.; Li, L.; Sun, Y.; Zhang, T.; Peng, F. Effects of Nearly Four Decades of Long-Term Fertilization on the Availability, Fraction and Environmental Risk of Cadmium and Arsenic in Red Soils. *J. Environ. Manage.* 2021, 295, 113097.

McBride, S. A.; Dash, S.; Khan, S.; Varanasi, K. K. Evaporative Crystallization of Spirals. *Langmuir* 2019. https://doi.org/10.1021/acs.langmuir.9b01002.

Li, H.; Wang, C.; Wang, X.; Hou, P.; Luo, B.; Song, P.; Pan, D.; Li, A.; Chen, L. Disposable Stainless Steel-Based Electrochemical Microsensor for in Vivo Determination of Indole-3-Acetic Acid in Soybean Seedlings. *Biosens. Bioelectron.* 2019, 126, 193-199.

Huang, C. H.; Singh, G. P.; Park, S. H.; Chua, N.-H.; Ram, R. J.; Park, B. S. Early Diagnosis and Management of Nitrogen Deficiency in Plants Utilizing Raman Spectroscopy. *Front. Plant Sci.* 2020, 11, 663.

Zhu, Z.; Ling, S.; Yeo, J.; Zhao, S.; Tozzi, L.; Buchler, M. J.; Omenetto, F.; Li, C.; Kaplan, D. L. High-Strength, Durable All-Silk Fibroin Hydrogels with Versatile Processability toward Multifunctional Applications. *Adv. Funct. Mater.* 2018. https://doi.org/10.1002/adfm.201704757.

Marelli, B.; Patel, N.; Duggan, T.; Perotto, G.; Shirman, E.; Li, C.; Kaplan, D. L.; Omenetto, F. G. Programming Function into Mechanical Forms by Directed Assembly of Silk Bulk Materials. *Proc. Natl. Acad. Sci.* 2017. https://doi.org/10.1073/pnas.1612063114.

Zvinavashe, A. T.; Lim, E.; Sun, H.; Marelli, B. A Bioinspired Approach to Engineer Seed Microenvironment to Boost Germination and Mitigate Soil Salinity. *Proc. Natl. Acad. Sci.* 2019, 116 (51), 25555-25561. https://doi.org/10.1073/PNAS.1915902116.

Melke, J.; Midha, S.; Ghosh, S., Ito, K.; Hofmann, S. Silk Fibroin as Biomaterial for Bone Tissue Engineering. *Acta Biomaterialia.* 2016. https://doi.org/10.1016/j.actbio.2015.09.005.

Ruggeri, E.; Kim, D.; Cao, Y.; Fare, S.; De Nardo, L.; Marelli, B. A Multilayered Edible Coating to Extend Produce Shelf Life. *ACS Sustain. Chem. Eng.* 8 (38), 14312-14321. https://doi.org/10.1021/acssuschemeng.0c03365.

Zhou, L.; Chen, X.; Shao, Z.; Huang, Y.; Knight, D. P. Effect of Metallic Ions on Silk Formation in the Mulberry Silkworm, *Bombyx* m Ori. *J. Phys. Chem. B* 2005, 109 (35), 16937-16945.

S. Iijima, *Nature* 1991, 354, 56.

J. M. Schnorr, T. M. Swager, *Chem. Mater.* 2011, 23, 646.

Y. Sun, Y. Xia, *Adv. Mater.* 2004, 16, 264.

H. Liang, S. Liu, S. Yu, *Adv. Mater.* 2010, 22, 3925.

J. Goldberger, R. He, Y. Zhang, S. Lee, H. Yan, H.-J. Choi, P. Yang, *Nature* 2003, 422, 599.

M. Steinhart, J. H. Wendorff, A. Greiner, R. B. Wehrspohn, K. Nielsch, J. Schilling, J. Choi, U. Gosele, *Science* (80-.). 2002, 296, 1997.

M. Steinhart, R. B. Wehrspohn, U. Gösele, J. H. Wendorff, *Angew. Chemie Int. Ed.* 2004, 43, 1334.

L. Adler-Abramovich, D. Aronov, P. Beker, M. Yevnin, S. Stempler, L. Buzhansky, G. Rosenman, E. Gazit, *Nat. Nanotechnol.* 2009, 4, 849.

T. Shimizu, M. Masuda, H. Minamikawa, *Chem. Rev.* 2005, 105, 1401.

Y. Zhou, T. Shimizu, *Chem. Mater.* 2008, 20, 625.

I. W. Hamley, *Angew. Chemie Int. Ed.* 2014, 53, 6866.

C. Cheng, Z. Z. Shao, F. Vollrath, *Adv. Funct. Mater.* 2008, 18, 2172.

B. P. Partlow, C. W. Hanna, J. Rnjak-Kovacina, J. E. Moreau, M. B. Applegate, K. A. Burke, B. Marelli, A. N. Mitropoulos, F. G. Omenetto, D. L. Kaplan, *Adv. Funct. Mater.* 2014, 24, 4615.

P. Tseng, B. Napier, S. W. Zhao, A. N. Mitropoulos, M. B. Applegate, B. Marelli, D. L. Kaplan, F. G. Omenetto, *Nat. Nanotechnol.* 2017, 12, 474.

F. Zhang, X. You, H. Dou, Z. Liu, B. Zuo, X. Zhang, *ACS Appl. Mater. Interfaces* 2015, 7, 3352.

M. B. Bryning, D. E. Milkie, M. F. Islam, L. A. Hough, J. M. Kikkawa, A. G. Yodh, *Adv. Mater.* 2007, 19, 661.

H. Jin, J. Park, V. Karageorgiou, U. Kim, R. Valluzzi, P. Cebe, D. L. Kaplan, *Adv. Funct. Mater.* 2005, 15, 1241.

H. Sun, B. Marelli, *Nat. Commun.* 2020, 11, 1.

A. B. D. Cassie, Sjt. Baxter, *Trans. Faraday Soc.* 1944, 40, 546.

A. Marcati, A. V. Ursu, C. Laroche, N. Soanen, L. Marchal, S. Jubeau, G. Djelveh, P. Michaud, *Algal Res.* 2014, 5, 258.

S. Krishnan, C. J. Weinman, C. K. Ober, *J. Mater. Chem.* 2008, 18, 3405.

S. T. Parker, P. Domachuk, J. Amsden, J. Bressner, J. A. Lewis, D. L. Kaplan, F. G. Omenetto, *Adv. Mater.* 2009, 21, 2411.

B. Marelli, M. A. Brenckle, D. L. Kaplan, F. G. Omenetto, *Sci. Rep.* 2016, 6, DOI ARTN 2526310.1038/srep25263.

E. Ruggeri, D. Kim, Y. Cao, S. Farè, L. De Nardo, B. Marelli, *ACS Sustain. Chem. Eng.* 2020, 8, 14312.

D. N. Rockwood, R. C. Preda, T. Yücel, X. Wang, M. L. Lovett, D. L. Kaplan, *Nat. Protoc.* 2011, 6, 1612.

A. S. Schenk, E. J. Albarracin, Y.-Y. Kim, J. Ihli, F. C. Meldrum, *Chem. Commun.* 2014, 50, 4729.

J. Wang, S. Lec, A. R. Bielinski, K. A. Meyer, A, Dhyani, A. M. Ortiz-Ortiz, A. Tuteja, N. P. Dasgupta, *Adv. Mater. Interfaces* 2020, 7, 2000672.

A. ASTM, *Annu. B. ASTM Stand. Am. Soc. Test. Mater. West Conshohocken, PA, USA* 2016, 719.

What is claimed is:

1. A microneedle comprising:
(a) silk fibroin, and
(b) one or more inorganic ions selected from NaCl and $CuSO_4$, wherein the microneedle comprises a hollow base and a penetrating tip.

2. The microneedle of claim 1, wherein the microneedle comprises an open channel from the hollow base to the penetrating tip.

3. The microneedle of claim 1, wherein the penetrating tip is porous.

4. The microneedle of claim 2, comprising at least one active agent selected from the group consisting of vitamins, proteins, peptides, antigens, immunogens, vaccines, antibodies or portions thereof, antibody-like molecules, enzymes, nucleic acids, siRNA, shRNA, aptamers, viruses, bacteria, small molecules, cells, hormones, antibiotics, therapeutic agents, diagnostic agents, and any combinations thereof, wherein the delivery molecule is present in the open channel of the microneedle.

5. The microneedle of claim 4, wherein the active agent is a vitamin.

6. The microneedle of claim 5, wherein the vitamin is Vitamin $B_{12}$.

7. The microneedle of claim 1, wherein the silk fibroin comprises larger silk fibroin ($SF_L$) which has an average molecular weight of about 270 kDa, and/or smaller silk fibroin ($SF_S$) which has an average molecular weight of about 200 kDa.

8. The microneedle of claim 7, wherein the silk fibroin comprises larger silk fibroin ($SF_L$).

9. The microneedle of claim 7, wherein the silk fibroin comprises smaller silk fibroin ($SF_S$).

10. The microneedle of claim 1, wherein the inorganic ion comprises NaCl.

11. The microneedle of claim 1, wherein the inorganic comprises $CuSO_4$.

12. The microneedle of claim 1, wherein the silk fibroin is present at about 95-99% w/w dry weight of the microneedle, and the one or more inorganic ions are present at about 1-5% w/w dry weight of the microneedle.

13. The microneedle of claim 2, wherein the silk fibroin is present at about 95% w/w dry weight of the microneedle, and the inorganic ion is present at about 5% w/w dry weight of the microneedle.

14. The microneedle of claim 3, wherein the silk fibroin is present at about 98-99% w/w dry weight of the microneedle, and the inorganic ion is present at about 1-2% w/w dry weight of the microneedle.

15. The microneedle of claim 12, wherein the silk fibroin is $SF_S$, and the one or more inorganic ions comprises $CuSO_4$.

16. The microneedle of claim 1, wherein the microneedle has a base diameter of about 600 μm.

17. The microneedle of claim 1, wherein the microneedle has a length of about 1600 μm.

18. A microneedle array, comprising a plurality of the microneedle of claim 1 arranged on a surface.

19. The microneedle array of claim 17, wherein the surface comprises an extension of the plurality of microneedles.

* * * * *

SEQUENCE LISTING

```
Sequence total quantity: 18
SEQ ID NO: 1            moltype = AA  length = 6
FEATURE                 Location/Qualifiers
REGION                  1..6
                        note = Synthetic
VARIANT                 1..6
                        note = Can be repeated 5-15 times
source                  1..6
                        mol_type = protein
                        organism = synthetic construct
SEQUENCE: 1
GAGAGS                                                              6

SEQ ID NO: 2            moltype = AA  length = 4
FEATURE                 Location/Qualifiers
REGION                  1..4
                        note = Synthetic
source                  1..4
                        mol_type = protein
                        organism = synthetic construct
SEQUENCE: 2
GAAS                                                                4
```

```
SEQ ID NO: 3            moltype =   length =
SEQUENCE: 3
000

SEQ ID NO: 4            moltype =   length =
SEQUENCE: 4
000

SEQ ID NO: 5            moltype = AA  length = 6
FEATURE                 Location/Qualifiers
REGION                  1..6
                        note = Synthetic
source                  1..6
                        mol_type = protein
                        organism = synthetic construct
SEQUENCE: 5
GLGGLG                                                                      6

SEQ ID NO: 6            moltype = AA  length = 6
FEATURE                 Location/Qualifiers
REGION                  1..6
                        note = Synthetic
VARIANT                 2
                        note = X is L, I, V, or P
VARIANT                 5
                        note = X is L, I, V, or P
source                  1..6
                        mol_type = protein
                        organism = synthetic construct
SEQUENCE: 6
GXGGXG                                                                      6

SEQ ID NO: 7            moltype = AA  length = 6
FEATURE                 Location/Qualifiers
REGION                  1..6
                        note = Synthetic
VARIANT                 1..6
                        note = can be repeated 1 to 10 times
VARIANT                 3..5
                        note = can be repeated 1 to 4 times
VARIANT                 5
                        note = X is Y, V, S, or A
source                  1..6
                        mol_type = protein
                        organism = synthetic construct
SEQUENCE: 7
GPGGXY                                                                      6

SEQ ID NO: 8            moltype = AA  length = 5
FEATURE                 Location/Qualifiers
REGION                  1..5
                        note = Synthetic
VARIANT                 5
                        note = can be repeated 1-10 times
source                  1..5
                        mol_type = protein
                        organism = synthetic construct
SEQUENCE: 8
GRGGA                                                                       5

SEQ ID NO: 9            moltype = AA  length = 7
FEATURE                 Location/Qualifiers
REGION                  1..7
                        note = Synthetic
VARIANT                 4
                        note = can be repeated 6-7 times
source                  1..7
                        mol_type = protein
                        organism = synthetic construct
SEQUENCE: 9
GAGAGGA                                                                     7

SEQ ID NO: 10           moltype = AA  length = 8
FEATURE                 Location/Qualifiers
REGION                  1..8
                        note = Synthetic
VARIANT                 3
                        note = X is Q, Y, L, A, S, or R
```

```
VARIANT                 5
                        note = X is Q, Y, L, A, S, or R
VARIANT                 7..8
                        note = X is Q, Y, L, A, S, or R
source                  1..8
                        mol_type = protein
                        organism = synthetic construct
SEQUENCE: 10
GGXGXGXX                                                                8

SEQ ID NO: 11           moltype = AA  length = 16
FEATURE                 Location/Qualifiers
REGION                  1..16
                        note = Synthetic
source                  1..16
                        mol_type = protein
                        organism = synthetic construct
SEQUENCE: 11
TGSSGFGPYV NGGYSG                                                       16

SEQ ID NO: 12           moltype = AA  length = 8
FEATURE                 Location/Qualifiers
REGION                  1..8
                        note = Synthetic
source                  1..8
                        mol_type = protein
                        organism = synthetic construct
SEQUENCE: 12
YEYAWSSE                                                                8

SEQ ID NO: 13           moltype = AA  length = 7
FEATURE                 Location/Qualifiers
REGION                  1..7
                        note = Synthetic
source                  1..7
                        mol_type = protein
                        organism = synthetic construct
SEQUENCE: 13
SDFGTGS                                                                 7

SEQ ID NO: 14           moltype = AA  length = 7
FEATURE                 Location/Qualifiers
REGION                  1..7
                        note = Synthetic
source                  1..7
                        mol_type = protein
                        organism = synthetic construct
SEQUENCE: 14
RRAGYDR                                                                 7

SEQ ID NO: 15           moltype = AA  length = 8
FEATURE                 Location/Qualifiers
REGION                  1..8
                        note = Synthetic
source                  1..8
                        mol_type = protein
                        organism = synthetic construct
SEQUENCE: 15
EVIVIDDR                                                                8

SEQ ID NO: 16           moltype = AA  length = 18
FEATURE                 Location/Qualifiers
REGION                  1..18
                        note = Synthetic
source                  1..18
                        mol_type = protein
                        organism = synthetic construct
SEQUENCE: 16
TTIIEDLDIT IDGADGPI                                                     18

SEQ ID NO: 17           moltype = AA  length = 8
FEATURE                 Location/Qualifiers
REGION                  1..8
                        note = Synthetic
source                  1..8
                        mol_type = protein
                        organism = synthetic construct
SEQUENCE: 17
TISEELTI                                                                8
```

-continued

```
SEQ ID NO: 18          moltype =   length =
SEQUENCE: 18
000
```